(12) United States Patent
Needham et al.

(10) Patent No.: US 6,296,870 B1
(45) Date of Patent: *Oct. 2, 2001

(54) LIPOSOMES CONTAINING ACTIVE AGENTS

(75) Inventors: David Needham; Ranjit S. Sarpal, both of Durham, NC (US)

(73) Assignee: Duke University, Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/017,984

(22) Filed: Feb. 3, 1998

Related U.S. Application Data

(63) Continuation-in-part of application No. 08/795,100, filed on Feb. 6, 1997, now Pat. No. 5,827,533.

(51) Int. Cl.[7] .......................... A61K 9/127; A61K 9/133
(52) U.S. Cl. ................... 424/450; 424/1.21; 424/9.321; 424/9.51; 424/94.3; 935/54
(58) Field of Search ..................... 424/450, 417, 424/1.21, 9.321, 9.51, 94.3; 935/54; 428/402.2

(56) References Cited

U.S. PATENT DOCUMENTS

| | | | |
|---|---|---|---|
| 4,489,056 | 12/1984 | Himmelstein et al. | 424/22 |
| 4,544,545 | 10/1985 | Ryan et al. | 424/450 |
| 4,551,288 | 11/1985 | Kelly | 264/4.6 |
| 4,737,323 | 4/1988 | Martin et al. | 424/450 |
| 4,752,425 | 6/1988 | Martin et al. | 264/4.6 |
| 4,756,910 | 7/1988 | Yagi et al. | 424/450 |
| 4,762,915 | 8/1988 | Kung et al. | 530/405 |
| 4,828,837 * | 5/1989 | Uster | 424/450 |
| 4,837,028 | 6/1989 | Allen | 424/45 |
| 4,839,111 | 6/1989 | Huang | 264/4.6 |
| 4,876,094 | 10/1989 | Beaton et al. | 442/491 |
| 4,900,556 | 2/1990 | Wheatley et al. | 424/450 |
| 4,906,476 * | 3/1990 | Radhakrishan | 424/450 |
| 4,906,477 | 3/1990 | Kurono et al. | 424/450 |
| 4,920,016 | 4/1990 | Allen et al. | 424/450 |
| 4,921,644 * | 5/1990 | Lau | 264/4.1 |
| 4,921,706 * | 5/1990 | Robers | 44/450 |
| 4,921,757 | 5/1990 | Wheatley et al. | 428/402.2 |
| 5,013,556 * | 5/1991 | Woodle | 424/450 |
| 5,023,086 | 6/1991 | Wallach | 424/450 |
| 5,094,854 | 3/1992 | Ogawa et al. | 424/423 |
| 5,160,669 | 11/1992 | Wallach et al. | 264/4.3 |
| 5,213,804 | 5/1993 | Martin et al. | 424/450 |
| 5,225,212 | 7/1993 | Martin et al. | 424/450 |

(List continued on next page.)

FOREIGN PATENT DOCUMENTS

| | | | |
|---|---|---|---|
| WO 91/05546 | 5/1991 | (WO) | A61K/9/127 |
| WO 92/03123 | 3/1992 | (WO) | A61K/9/127 |
| WO 92/22249 | 12/1992 | (WO) | A61B/8/14 |

(List continued on next page.)

OTHER PUBLICATIONS

Database WPI, Section Ch, Week 9633 Derwent publications limited, London Class B05, AN 96–329429 XP002065766 and JP 08 151 333 A (Kamioka R) Jun. 11, 1996.

(List continued on next page.)

Primary Examiner—Gollamudi S. Kishore
(74) Attorney, Agent, or Firm—Myers Bigel Sibley & Sajovec, P.A.

(57) ABSTRACT

Liposomes formulations are designed to maximize the amount of poorly water-soluble active agent that can be carried by the liposome. Liposomes containing active agent in the lipid bilayer of the liposome, and/or entrapped within the liposome interior space in a micellar preparation are described. Methods of making such liposomes are presented.

10 Claims, 27 Drawing Sheets

U.S. PATENT DOCUMENTS

| | | |
|---|---|---|
| 5,356,633 | 10/1994 | Woodle et al. ............... 424/450 |
| 5,395,619 | 3/1995 | Zalipsky et al. ............... 424/450 |
| 5,415,869 | 5/1995 | Straubinger et al. ............... 424/450 |
| 5,478,860 | 12/1995 | Wheeler et al. ............... 514/449 |
| 5,527,528 | 6/1996 | Allen et al. ............... 424/178.1 |
| 5,534,241 | 7/1996 | Torchilin et al. ............... 424/9.321 |
| 5,534,499 | 7/1996 | Ansell ............... 514/25 |
| 5,552,156 | 9/1996 | Burke ............... 424/450 |
| 5,561,062 | 10/1996 | Varanelli et al. ............... 435/238 |
| 5,622,498 | 4/1997 | Brizzolara et al. ............... 433/80 |
| 5,628,936 | 5/1997 | Wallach ............... 264/4.1 |
| 5,643,600 | 7/1997 | Mathur ............... 424/450 |
| 5,665,380 | 9/1997 | Wallach et al. ............... 424/450 |
| 5,683,715 * | 11/1997 | Boni ............... 424/450 |
| 5,755,788 | 5/1998 | Strauss ............... 623/11 |

FOREIGN PATENT DOCUMENTS

| | | | |
|---|---|---|---|
| WO 93/19738 | 10/1993 | (WO) | ............... A61K/9/127 |
| WO 93/20800 | 10/1993 | (WO) | . |
| WO 94/13265 | 6/1994 | (WO) | ............... A61K/9/127 |
| WO 94/21235 | 9/1994 | (WO) | ............... A61K/9/127 |
| WO 94/26251 | 11/1994 | (WO) | ............... A61K/9/127 |
| WO 95/08986 | 4/1995 | (WO) | ............... A61K/9/127 |
| WO 96/14057 | 5/1996 | (WO) | ............... A61K/9/127 |
| WO 96/25147 | 8/1996 | (WO) | ............... A61K/9/127 |

OTHER PUBLICATIONS

Kenworthy et al.; Range and Magnitude of the Steric Pressure Between Bilayers Containing Phospholipids with Covalently Attached Poly(ethylene glycol), *Biophysical Journal*, 68:1921–1936 (1995).

Kenworthy et al.; Structure and Phase Behavior of Lipid Suspensions Containing phospholipids with Covalently Attached Poly(ethylene glycol); *Biophysical Journal*, 68:1903–1920 (1995).

Mark W. Dewhirst and David Needham; Extravasation of Stealth® Liposomes Into Tumors: Direct Measurement of Accumulation and Vascular Permeability Using a Skin Flap Window Chamber; *Stealth® Liposomes*; Chapter 12:127–137 (1995).

Hayat Alkan–Onyuksel et al.; A Mixed Micellar Formulation Suitable for the Parenteral Administration of Taxol; *Pharmaceutical Research*; 11(2):206–212 (1994).

D. Needham et al.; Repulsive Interactions and Mechanical Stability of Polymer–Grafted Lipid Membranes; *Biochimica et Biophysica Acta*; 1108:40–48 (1992).

Needham, et al.; The Mechanochemistry of Lipid Vesicles Examined by Micropipet Manipulation Techniques, In: *Vesicles* (M. Rosoff, ed.), Chapter 9, pp. 374–439 (1996).

Noppl–Simson and Needham, Avidin–Biotin Interactions at Vesicle Surfaces: Adsorption and Binding, Cross–Bridge Formation, and Lateral Interactions, *Biophysical Journal* 70:1391.

Sharma and Straubinger, Novel Taxol Formulations: Preparation and Characterization of Taxol–Containing Lipsomes, *Pharm. Research*, 11:889–896 (1994).

Needham, et al., Exchange of Monooleoylphosphatidycholine as Monomer and Micelle with Membranes Containing Grafted Polyethyleneglycol, 73:2615 (1997).

Devlin, B.P. et al., *A Kinetic Study of the Polyelectrolyte–Induced Reorganization of Lipid Bilayers, Am, Chem, Soc. Div. Polym. Chem.* vol. 28, No. 2, (1987), pp. 50–51.

Hristova, K., et al., *Effect of Bilayer Composition On the Phase Behavior Liposomal Suspensions Containing Poly-(ethylene glycol) Lipids, Macromolecules*, vol. 28, No. 23 (1995) pp. 7693–7699.

International Search Report for corresponding International application No. PCT/US99/12964.

* cited by examiner 1  2  3  4

LIPOSOMES CONTAINING ACTIVE AGENTS

RELATED APPLICATIONS

This application is a Continuation-in-Part of application Ser. No. 08/795,100 filed Feb. 6, 1997, now U.S. Pat. No. 5,827,533, the contents of which are hereby incorporated herein in their entirety.

This invention was made with government support under National Institutes of Health grant #GM40162. The Government has certain rights to this invention.

FIELD OF THE INVENTION

The present invention relates to liposomes containing active agents such as therapeutic drugs, where the liposome membrane is formulated to provide a liposome with increased carrying capacity for poorly water-soluble active agents. Alternatively or in addition, the active agent may be contained within, or adsorbed onto, the liposome bilayer. The active agent may be aggregated with a lipid surfactant and carried within the liposome's internal space; the liposome membrane is formulated to resist the disruptive effects of the active agent-surfactant aggregate.

BACKGROUND OF THE INVENTION

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVs) are typically larger than 0.05 μm. Oligolamellar large vesicles and multilamellar vesicles have multiple, usually concentric, membrane layers and are typically larger than 0.1 μm. Liposomes with several non-concentric membranes, i.e., several smaller vesicles contained within a larger vesicle, are termed multivesicular vesicles.

Conventional liposomes are formulated to carry drugs or other active agents either contained within the aqueous interior space (water-soluble drugs) or partitioned into the lipid bilayer (water-insoluble drugs). As used herein, active agents "entrapped" within liposomes are those which are in the interior space of the liposome, compared to those which are partitioned into the lipid bilayer and contained in the vesicle membrane itself. Active agents which have short half-lives in the bloodstream are particularly suited to delivery via liposomes. Many anti-neoplastic agents, for example, are known to have a short half-life in the bloodstream such that their parenteral use is not feasible. However, the use of liposomes for site-specific delivery of active agents via the bloodstream is severely limited by the rapid clearance of liposomes from the blood by cells of the reticuloendothelial system (RES).

The action of many drugs involves their direct interaction with hydrophobic sites within a cell, or their ability to pass through the cell membrane into cytoplasmic and nuclear compartments. These hydrophobic interactions are due to regions on the molecule that are poorly solvated by water, such that the overall aqueous solubility of the drug is compromised. One such drug is TAXOL®, which has a water solubility of about 1 micromolar. The solubility of TAXOL® can be somewhat increased by chemical modification, but it is not clear how such modifications affect the function of the drug.

The efficacy of many drugs is limited by their inability to reach the intended therapeutic site. In many cases only a small fraction of the administered dose of a drug (even if water soluble) reaches the therapeutic site; most of the drug is distributed throughout the body. This distribution into healthy organs and tissues often limits dosage. Drug formulations and drug delivery methods that suspend significant amounts of a therapeutic compound in an aqueous medium, that are stabilized against dissolution in the body, and that provide for site specific delivery are therefore desirable.

The formulation of drugs with poor water solubility has traditionally focused on the use of emulsions and other association colloids, such as micelles, that dissolve the drug and therefore increase its concentration in aqueous media. However, these emulsions (and particularly micellar suspensions) are not necessarily stable and targetable to specific anatomic sites. When placed in contact with plasma or whole blood, a repartitioning of drug from a micelle or emulsion into cells and macromolecular components occurs, and the drug solubilizing system no longer retains the drug.

A liposome consists of a lipid membrane surrounding an aqueous interior, and thus has the capacity to carry both water-soluble and water-insoluble drugs in its interior and its membrane, respectively. The liposome membrane, however, represents only a small part of the total volume of the total liposome construct; the capacity of a liposome to carry and release a poorly water-soluble drug in a dispersible form is limited by the small volume of the liposome membrane. The present invention optimizes the lipid composition of liposome bilayers, so that the lipid membrane can carry increased amounts of drug. The present invention also provides methods to optimize the ability of the aqueous interior to carry drug. The present invention, in particular, provides a liposome designed to carry large amounts of TAXOL®.

It is accordingly desirable to devise liposome formulations capable of delivering therapeutic amounts of active agent via parenteral administration, and resulting in an extended half-life of active agent in the blood stream.

SUMMARY OF THE INVENTION

It is therefore a general object of the present invention to provide a liposome composition and method for administering a therapeutically effective amount of a compound for an extended period in the bloodstream.

A first object of the present invention is a liposome containing an active agent, where the liposome bilayer membrane contains vesicle-forming lipid derivatized with hydrophilic polymer. The active agent is aggregated with a lipid surfactant and entrapped within the liposome. The liposome membrane contains polymer-derivatized lipid in an amount sufficient to inhibit fusion of the membrane with the active agent/surfactant aggregate entrapped therein.

A further object of the present invention is a liposome containing an active agent, where the liposome bilayer membrane contains vesicle-forming lipid derivatized with polyethylene glycol. the active agent is aggregated with a lipid surfactant and entrapped within the liposome. The liposome membrane contains polyethylene glycol in an amount sufficient to inhibit fusion of the membrane with the active agent/surfactant aggregate entrapped therein.

A further object of the present invention is a liposome containing a micellar preparation of paclitaxel, where the liposome bilayer membrane contains from 1 mole percent to 22 mole percent vesicle-forming lipid derivatized with polyethylene glycol of molecular weight 750 daltons.

A further object of the present invention is a method for preparing an active agent for intravenous administration, by entrapping an active agent aggregated with lipid surfactant in a liposome, where the lipid bilayer membrane of the liposome contains vesicle-forming lipids derivatized with a hydrophilic polymer. the polymer-derivatized lipid is contained in the liposome membrane in an amount sufficient to inhibit fusion of the membrane with the active agent-lipid aggregate contained therein.

A further object of the present invention is a liposome containing an active agent, where the liposome bilayer membrane contains cholesterol. The active agent is aggregated with a lipid surfactant and entrapped within the liposome. The liposome membrane contains cholesterol in an amount sufficient to inhibit fusion of the membrane with the active agent/surfactant aggregate entrapped therein.

A further object of the present invention is a liposome containing an active agent, where the liposome lipid bilayer membrane contains protective molecules extending from the surface of the lipid bilayer. The active agent is aggregated with a lipid surfactant and entrapped within the liposome, and the liposome membrane contains protective molecules in an amount sufficient to inhibit fusion of the liposome membrane with the active agent-lipid surfactant aggregate therein.

A further aspect of the present invention is a liposome containing an active agent, where the lipid bilayer of the liposome comprises phospholipid, an active agent that is poorly water soluble, and surfactant with a low Critical Micelle Concentration (CMC). The surfactant is contained in the lipid bilayer in an amount sufficient to increase the amount of active agent associated with the lipid bilayer, compared to that amount of active agent that would associate with the lipid bilayer in the absence of surfactant.

A further aspect of the present invention is a liposome having lipid bilayer comprising phospholipid, surfactant with a low Critical Micelle Concentration (CMC), and cholesterol, and having a micellar preparation of an active agent within the interior space of the liposome. The cholesterol is contained in the lipid bilayer in an amount sufficient to increase the stability of the micelle-containing liposome compared to that which would be observed in the absence of cholesterol.

A further aspect of the present invention is a liposome containing paclitaxel, where the liposome bilayer comprises phospholipid, lysophosphatidylcholine, and cholesterol in a mole ratio of about 8:4:3, and where a micellar preparation of paclitaxel is contained within the interior of the liposome.

A further aspect of the present invention is a method of making a liposome containing a micellar preparation of an active agent within the liposome interior. The method comprises first preparing a phospholipid film containing cholesterol and a surfactant having a low Critical Micelle Concentration (CMC). The lipid film is then hydrated with a micellar preparation of an active agent. The phospholipid film contains cholesterol in an amount sufficient to increase the stability of the liposome, compared to that which would be observed in the absence of cholesterol.

A further aspect of the present invention is a method of making a liposome containing paclitaxel in the lipid bilayer, and containing a micellar preparation of paclitaxel in the liposome interior space. The method includes first preparing a phospholipid film containing paclitaxel, cholesterol and a surfactant having a low Critical Micelle Concentration. The phospholipid film is then hydrated with a micellar preparation of paclitaxel. The phospholipid film contains cholesterol in an amount sufficient to increase the stability of the liposome compared to that which would be observed in the absence of cholesterol.

The foregoing and other objects and aspects of the present invention are explained in detail in the specification set forth below.

DETAILED DESCRIPTION OF THE INVENTION

Figure 1A:
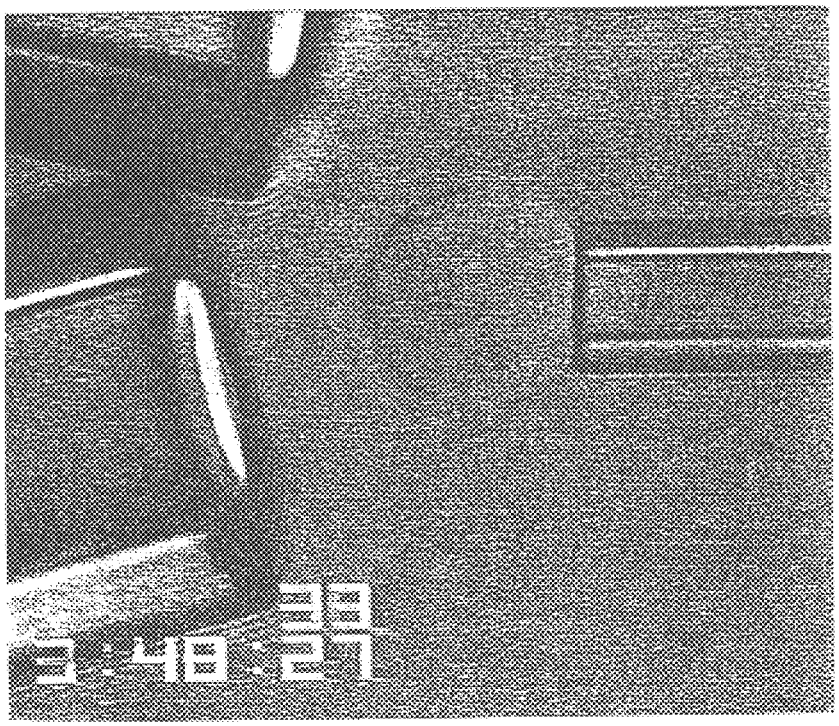
FIG. 1A is a videomicrograph of a holding pipet holding a test vesicle, and a flow pipet delivering monooleyolphosphatidylcholine (MOPC)-free bathing solution at a controlled flow rate to the exterior of the test vesicle. The vesicle projection length ($L_p$) inside the holding pipet can be measured.

In conventional therapeutic liposome preparations, the active agent is either sequestered within the aqueous interior compartment of the liposome (water-soluble active agents) or is associated with the liposome bilayer membrane (water-insoluble agents). However, partitioning of water-insoluble (lipophilic) drugs into the membrane bilayer of a liposome compromises the physical properties of the membrane to the extent that, in some cases the encapsulating membrane does not retain the drug. Thus, in lipid-based encapsulating systems it would be desirable to protect the encapsulating liposome membrane from deleterious interactions with the active agent, drug or drug suspension contained therein.

Micelles and emulsions containing active agents are more mobile than liposome preparations, but micelles are stable only as long as they are in equilibrium with the surfactant monomer from which the micelle is formed, i.e., in the absence of equilibrating monomer, micelles simply break up into water-soluble monomers and the micelles dissolve. Similarly, in the absence of equilibrating monomer, emulsion droplets coalesce into larger and larger droplets as surfactant is lost. Thus, once a micelle preparation is diluted, for example by intravenous administration, micelles 'dissolve' and disperse in the surrounding aqueous media, releasing their contents in the blood stream in a matter of seconds. Emulsion preparations are similarly unstable. Other mechanisms of destruction, such as lipoprotein uptake of the micellized or emulsified drug contribute to the rapid depletion of such drug preparations in the blood stream. Where rapid administration of an active agent is desired, emulsions and micelle preparations are useful, but such preparations are not useful where delayed or extended administration is desired.

Thus the amount of lipophilic or amphipathic active agent that can be partitioned into a liposome membrane is limited due to the resulting membrane instability and the inherent solubility of the surfactant monomer in aqueous media and in lipoprotein particles. However, certain uses of liposomes require high concentrations of active agent in the liposomal carrier, i.e., for delivery of therapeutic agents to anatomical sites via the bloodstream, or for diagnostic imaging studies. In addition, the liposome must be able to retain the active agent for an extended time period if the desired effects are to be obtained.

A further issue in the intravenous use of liposomes is the rapid clearance of liposomes from the bloodstream by cells of the reticuloendothelial system (RES), located primarily in the liver and spleen. It is known that smaller liposome size favors longer liposome lifetime in the bloodstream (See, e.g. U.S. Pat. No. 5,225,212 to Martin et al; all patents referenced herein are intended to be incorporated herein in their entirety) . However, the intravesicular volume is limited in smaller liposomes, such that they may not be practical delivery systems for therapeutically effective amounts of active agents.

Liposome preparations have been devised which avoid rapid RES uptake and which thus have an increased half-life in the bloodstream. STEALTH® liposomes (Liposome Technology Inc., Menlo Park, Calif.) include polyethyleneglycol (PEG)-grafted lipids at about 5 mol % in the lipid bilayer. See, e.g., Allen, *UCLA Symposium on Molecular and Cellular Biology*, 89:405 (1989); Allen et al., *Biochim. Biophys. Acta* 1066:29 (1991); Klibanov et al., *FEBS Letters* 268:235 (1990); Needham et al., *Biochim. Biophys. Acta* 1108:40 (1992); Papahadjopoulos et al., *Proc. Natl. Acad. Sci. USA* 88:11460 (1991); Wu et al., *Cancer Research* 53:3765 (1993); Klibanov and Huang, *J. Liposome Research* 2:321 (1992); Lasic and Martin, Stealth Liposomes, In: Pharmacology and Toxicology, CRC Press, Boca Raton, Fla., (1995). See also U.S. Pat. No. 5,225,212 to Martin et al.; U.S. Pat. No. 5,395,619 to Zalipsky et al; regarding liposomes containing polymer grafted lipids in the vesicle membrane. The presence of polymers on the exterior liposome surface decreases the uptake of liposomes by the organs of the RES.

The present inventors have devised liposomes able to contain, within the liposome interior, active agents associated with lipid surfactants (e.g., micelles containing active agents). Thus liposomes of the present invention can be formulated to contain substantially water insoluble or partially water insoluble active agents for extended periods, without loss of membrane stability. The liposome membranes are constructed to resist the disruptive effects of the surfactant contained therein. In liposomes according to the present invention, the active agent is in a solubilized form, such as a micellar formulation of the active agent or an emulsion containing the active agent; the solubilized active agent is carried within a liposome whose membrane contains protective molecules which inhibit or prevent fusion of the liposome membrane and the surfactant aggregates within the liposome. For example, a liposome membrane which contains a percentage of lipids derivatized with a hydrophilic (i.e., water-soluble) polymer is able to stably contain a micellar preparation of active agent. As used herein, a lipid derivatized with a polymer refers to a lipid which is covalently joined at its polar group to a water-soluble polymer. The polymer component of the lipid bilayer protects the encapsulating liposome membrane from deleterious interactions with the solubilized active agent therein, as well as protecting the liposome from uptake by the RES, and thus the circulation time of the liposomes in the bloodstream is extended. Additionally, containment of a solubilized form of active agent within a liposome of the present invention allows more active agent to be delivered by a single liposome than could be achieved by a conventional liposome containing active agent partitioned into the vesicle membrane itself.

In one series of experiments, the present inventors studied the influence of grafted PEG(750) as PEG-lipids on monooleoylphosphatidylcholine (MOPC) monomer exchange and micelle fusion with lipid bilayer vesicle membranes. The experimental results show that PEG(750)-lipid has a strong inhibitory effect such that micelle-membrane fusion decreases with increasing surface density of grafted PEG(750). At approximately 20 mol % PEG-lipid (corresponding to complete coverage of the membrane surface by PEG(750) "mushroom" structures as described below), micelle/membrane fusion is essentially prevented. The experimental data of the present inventors are well described by a model in which micelle-membrane fusion is considered a first order reaction process. The modeling of micelle-membrane fusion in the presence of grafted PEG (750), and the consideration of geometry characteristics of both PEG(750) "mushroom" and MOPC micelle, show that micelles must be in intimate contact with the headgroups of the membrane lipids in order for the fusion process to occur. Thermodynamic analysis and stationary equilibrium Both suggest that the solution properties of surfactant in the aqueous and bilayer phases are not ideal, and that the surfactant molecules are slightly aggregated on average as trimers in the aqueous phase below the CMC. There may also be aggregation of surfactant molecules in the vesicle bilayer when exposed to surfactant concentrations above the CMC and this would be a first indication of defect formation that ultimately results in vesicle membrane breakdown and dissolution of the vesicle.

Thus the present inventors have found that polymers (such as polyethylene glycol (PEG)) grafted to lipids provide a strong steric repulsion against surface-surface and surface-macromolecule interactions. The present inventors studied the exchange of monooleoylphosphatidylcholine (MOPC) with vesicle membranes containing 750 dalton molecular weight surface-grafted PEG (incorporated as PEG-lipid) and have devised a simple energetic model for micelle uptake. In the experiments described herein, micropipet manipulation was used to support a single lipid vesicle and expose it to a flow of MOPC solution followed by a flow of MOPC-free bathing solution. MOPC uptake was detected by measuring increases in the projection length of the vesicle in the holding micropipet, which, at constant vesicle volume, is a direct measure of the vesicle area change (see FIGS. 1A and 1B; Examples 1 and 4). Control vesicles without grafted PEG showed saturable uptakes of approximately 5 mol % at MOPC concentrations of 3 micromolar (critical micelle concentration (CMC) of MOPC), while at 100 micromolar MOPC the control vesicles rapidly took up larger amounts (approximately 15 mol % of MOPC) and invariably broke up after only a few seconds. However, with increasing surface concentrations of PEG(750)-lipid in the vesicle membrane, the amount of MOPC taken up by the vesicle bilayer when exposed to 100 $\mu$M MOPC was reduced.

The present inventors found that the presence of lipid-grafted polymers (such as PEG(750)) in a vesicle membrane (e.g., in the lipid bilayer of a liposome) inhibits the partitioning of micelles into the lipid membrane. Additionally, the present inventors determined that the presence of even up to 20 mol % PEG-lipid in a vesicle membrane does not affect the exchange of lipid monomers both into and out of the membrane. While not wishing to be held to a particular theory, the present inventors hypothesize that micelle-membrane fusion is a first order rate reaction, and the activation energy for micelle access and uptake by the lipid bilayer is increased in polymer-containing liposomes due to the work required to create polymer-free areas at the membrane surface. The present inventors have shown that micelles must be in intimate (headgroup-headgroup) contact with the membrane for the fusion process to occur.

When lipid bilayer vesicles are placed in surfactant solutions, both surfactant monomers and micelles can interact with the bilayer to change the mass and composition of the bilayer within seconds (Evans et al., In Bile Acids in Gasteroenterology Basic and Clinical Advances, Hoffman et al. (Eds.) Kluwer Academic Publishers, Doderecht, Boston and London, pp. 59–68 (1994); Needham and Zhelev, *Ann. Biomed. Egr.* 23:287 (1995); Zhelev, *Biophys J.* 71:257 (1996)). These changes in composition have direct consequences on bilayer structure and material properties. Evans et. al (1994) used micropipet manipulation techniques to directly measure uptake, bilayer elastic area expansion, and rupture strength of single vesicles following transfer to solutions of bile acid. Reduction in bilayer strength was apparent at concentrations of bile acid well below the levels necessary for complete solubilization. Increase in vesicle area correlated with uptake of bile acid into both halves of the lipid bilayer. Measurements of elasticity showed a pronounced softening even at low concentrations of bile acid in the 1–2 mM range, well below the critical micelle concentration (CMC) of approximately 12 mM.

In contrast to this solubilizing power of the high CMC bile acids, the exchange of surfactants such as lysolecithin does not cause lipid bilayer failure at the CMC (where the amount of lysolecithin in the membrane reaches saturation at approximately a few mol %) (Needham and Zhelev, *Ann. Biomed. Egr.* 23:287 (1995)). Bilayers remain cohesive structures at the CMC, which, for lysolecithin is in the micromolar range or approximately ten thousand times lower than the CMC for bile acids. Uptake of lysolecithin appears to be initially limited to the outer, exposed monolayer of the vesicle bilayer, and not until the bilayer is exposed to higher concentrations of lysolecithin (approximately 10 micromolar and above) for longer times does the uptake exceed monolayer capacity, resulting in the transfer of lysolipid across the bilayer midplane and eventual rupture of the membrane. Membrane concentrations of approximately 30 mol % for a single vesicle can be achieved; this approaches the solubility limit of lipid bilayers in lysolipid solution (VanEchteld et al., Biochim. Biophys. Acta 649:211 (1981)).

The present inventors have found that with a low CMC surfactant such as a lysolipid, both monomer and micelles are involved in the molecular exchange ant eventual disruption of lipid vesicle bilayers, and have determined that micelle interactions with lipid bilayer surfaces are inhibited when the lipid bilayer contains a grafted water-soluble polymer, such as polyethylene glycol. As used herein, a low CMC surfactant refers to surfactants with CMCs of about 1 millimolar or less (i.e., CMCs of about 1,000 micromolar or less). Preferred are surfactants with CMCs of about 0.1 millimolar (100 micromolar) or less, or even about 0.01 millimolar (10 micromolar) or less. Exemplary low CMC surfactants suitable for use in the present invention are lysolipids such as lysolecithin.

An issue addressed by the present inventors' work is the role played by the aggregation of surfactant solutions in the exchange process, where surfactant concentrations are either below or above the critical micelle concentration. Uptake measurements showed the expected discontinuity at the CMC, i.e., the point at which large micellar aggregates of surfactant form. However, deviations from the behavior predicted for a simple two component system (monomer and micelle) point to the presence of oligomeric species intermediate between the single monomer and conventional micelle. It is shown that where lipid bilayer surfaces contain a polymer, the polymer acts to prevent not only large "conventional" micelles but also smaller "oligomeric" aggregates (dependant on the surface density of the polymer layer) from interacting with the lipid bilayer.

Modeling of such polymer grafted lipid layers indicates that, depending on molecular weight of the polymer and its surface density, at least two distinguishable regimes ("mushrooms" and "brushes") can be identified for the grafted polymer (see deGennes, Macromolecules 13:1069 (1980)). The mushroom conformation exists at low polymer density when the distance between grafting points is larger than the size of the region occupied by a single chain (the Flory radius) In this case, the conformation of an individual polymer chain is independent of the presence of other polymers (deGennes, Macromolecules 13:1069 (1980)). When the surface density is high, the chains are in a brush conformation and the extended chain conformation is determined mainly by the interactions with the neighboring chains (Carignano and Szleifer, J. Chem Phys. 100:3210; Chakrabarti and Toral, Macromolecules 23:2016 (1990); deGennes, Macromolecules 13:1069 (1980); Wijmans et al., Macromolecules 25:2657 (1992)).

The present inventors studied experimentally the exchange of monooleoyl-phosphatidylcholine (SOPC) with vesicle membranes containing surface-grafted PEG(750)-lipid, and determined that the transport of lysolipid monomers and micelles to the surface of a lipid bilayer depends on the molecular weight and surface density of the polymeric steric barrier at the bilayer interface, and that such transport can be inhibited. MOPC monomer uptake and micelle-membrane "fusion" are coupled with the rapid desorption of MOPC monomers (Needham and Zhelev, Ann. Biomed. Egr. 23:287 (1995)). This relation between uptake and desorption establishes a stationary concentration of MOPC in the membrane. The stationary MOPC concentration provides a direct assay for the dependence of MOPC exchange with the bilayer on the presence of grafted polymer (see Examples below).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG (750)). Polymers may also be defined by the number of monomers therein; a preferred embodiment of the present invention utilizes polymers of at least about three monomers, such PEG polymers consisting of three monomers (approximately 150 daltons).

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

A variety of coupling methods for preparing a vesicle-forming lipid derivatized with a biocompatible, hydrophilic polymer such as polyethylene glycol are known in the art. See, e.g., U.S. Pat. No. 5,213,804 to Martin et al; U.S. Pat. No. 5,013,556 to Woodle et al) (all US patents referenced herein are intended to be incorporated in their entirety herein).

Vesicle-forming Lipids

Vesicle forming lipids suitable for-use in the present invention are preferably those having two hydrocarbon chains, typically acyl chains, and a polar head group, such as the phospholipids. Phospholipids include phosphatidylcholine, phosphatidylethanolamine, phosphatidic acid, phosphotidylglycerol, phosphatidylinositol, and sphingolipids such as sphingomyelin. Also included in this class are the glycolipids such as cerebrosides and gangliosides. Such lipids are available commercially or may be prepared using methods known in the art.

Cholesterol, derivatives of cholesterol (such as cholesterol sulfate and cholesterol hemisuccinate), and related sterols are also vesicle-forming lipids which may be used in the present invention. Additionally, cholesterol may be added to a liposome made up primarily of another lipid. Cholesterol may also be derivatized with the polymer.

"Vesicle-forming lipid" as used herein generally means any amphipathic lipid having hydrophobic and polar head group moieties, and which can form spontaneously into bilayer vesicles in water (as exemplified by phospholipids), or lipids which are stably incorporated into lipid bilayers in combination with other lipids such as phospholipids. When formed into vesicles, the hydrophobic moiety of a vesicle-forming lipid is in contact with the interior hydrophobic region of the bilayer membrane, and the polar head group moiety is oriented toward the polar surface of the membrane.

Percentages of Polymer-grafted Lipids in Liposomes

The present inventors have determined that the transport of surfactant monomers and micelles to the surface of a lipid bilayer is affected by the presence of polymer chains attached to lipids within the bilayer; these findings allow the preparation of liposomes capable of containing micellar or emulsified preparations of active agents. In such liposomes, the lipid bilayer contains polymer-grafted lipids in an amount sufficient to inhibit fusion of the membrane with the lipid-active agent aggregates (micelles or emulsions) contained therein; inhibition of fusion is measured by comparison to liposomes which do not contain any polymer-grafted lipids.

Where the grafted polymer is PEG(750) and the active agent-containing micelles are made up of MOPC lipid (or other micelle forming surfactant), micelle/membrane fusion begins to be inhibited when the surface concentration of grafted PEG(750) is 1 mol % or above. At surface concentrations of 20 mol % grafted PEG(750), micelle/membrane fusion is essentially completely inhibited (compared to liposomes without grafted PEG(750)), while monomeric species of MOPC lipids are still able to pass through the polymer layer and interact with the membrane surface (i.e., exchange of MOPC lipid monomers is not inhibited). At 20 mol % grafted PEG(750), the polymer is in a 'mushroom' configuration of sufficient density to prevent headgroup-headgroup interaction between a micelle and the lipid bilayer membrane, as described below.

In liposomes according to the present invention, the lipid bilayer contains a percentage of polymer-grafted lipids sufficient to inhibit micelle/membrane fusion. The percentage of polymer-grafted lipid required to inhibit micelle/membrane fusion will vary depending on the specific Polymer used and its molecular weight, and the lipid composition of the micelles contained within the liposome. It will further be apparent to those skilled in the art that the percentage of polymer can be varied to affect the stability of liposomes in vivo, with increasing amounts of polymer used to provide increasing liposome half-life. Thus liposomes according to the present invention may contain a minimum amount of polymer-grafted lipids sufficient to reduce (but not prevent) fusion of the membrane with micelles contained within the liposome (e.g., 1 mol % of PEG(750) where micelles are MOPC or other low-CMC surfactants), to an amount sufficient to essentially completely inhibit such micelle/membrane fusion (e.g., ≧20 mol % PEG(750)). The specific proportions of polymer will vary depending on the polymer utilized; the composition contained within the liposome, and the desired stability (or half-life) of the liposome. One skilled in the art will be able to determine desirable proportions using techniques described herein and available in the art.

Stated in another way, liposomes of the present invention contain micellar or emulsified preparations of active agents, and contain polymer-grafted lipids in the liposome bilayer in an amount sufficient to inhibit fusion of the membrane with the lipid-active agent aggregates contained therein; inhibition is measured by comparison to that which would occur in the absence of polymer. This inhibition of micelle/membrane fusion is evidenced by increased stability (half-life) of the liposome; the liposome resists degradation due to the lipids (micelles or emulsion) contained within, as well as that due to micelles in the exterior environment.

As used herein, in liposomes containing polymer-grafted lipids in the vesicle bilayer, polymer chains are in a "mushroom" regime or configuration when the shape of an individual polymer chain is not affected by the presence of other polymer chains; the polymer configuration is similar to that of a single chain in solution. In a "mushroom" regime, the polymer occupies a region next to the liposome membrane which can be determined by the Flory radius. When the lipid bilayer is essentially completely covered by polymers in the mushroom regime, the liposome is referred to as "saturated" or as containing a "saturating amount" of polymer-grafted lipid.

Micelle Structure

The present inventors have found that the addition of molecules such as polymers to the membrane bilayer of a liposome inhibits fusion of micelles with the liposome bilayer. Similarly, micelles that are to be contained within liposomes may be formulated to inhibit micelle/membrane fusion, by binding inhibitory molecules to the surface of the micelles. Such molecules include binding pairs (such as receptor/ligand pairs as discussed above); molecules of active agents such as therapeutic drugs; polymers such as PEG; proteins or polypeptides; and gangliosides. The molecules may be associated with the micelles by any suitable method, including by electrostatic charge, hydrogen bonds, van der Waals forces, amphipathic-hydrophobic chain interactions; and combinations thereof.

The micelle is a versatile component of the present invention, as it acts to solubilize or associate molecules and macromolecules that are either very soluble or insoluble. The micelle is an association colloid that displays regions of decreasing water solubility going from the outside of the structure to the inside. Identifying such regions is important to the capacity of micelles to solubilize a range of other solute molecules. These regions are summarized in FIG. 18.

Figure 18:
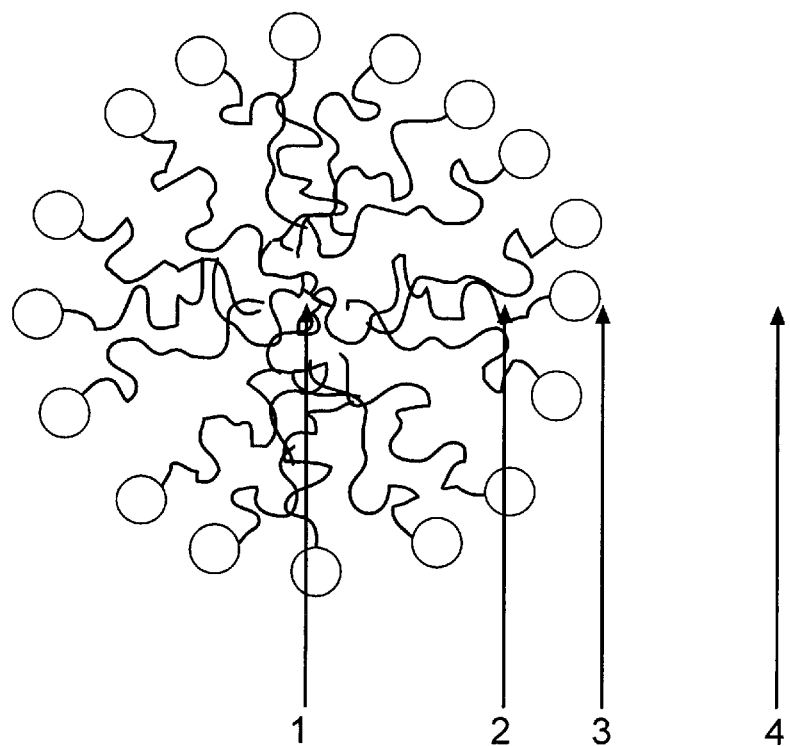
FIG. 18 depicts the four regions of a micelle, where (1) is the central core, (2) is the outer hydrocarbon chain area, (3) is the headgroup area, and (4) is the hydration layer/bulk solvent.

In the central core of a micelle, what might appear to be a liquid state for the hydrocarbon chains at the micelle center are actually appreciably different from bulk liquid hydrocarbons. Spectroscopic methods involving relaxation, such as fluorescence depolarization and electron spin resonance show that the hydrocarbon chains are unable to tumble and on the average remain oriented perpendicular to the micelle surface. Tanford, *The hydrophobic effect: Formation of micelles and biological membranes,* John Wiley and Sons, New York, N.Y. (1980). The liquid hydrocarbon state is characterized by fluctuations in molecular conformation and the presence of gauche bonds. However, because of the orientaional restriction, kinks in the chain are more likely to be formed by two gauche bonds in opposite directions rather than isolated gauche bonds. This leaves the overall direction of the chains unchanged as shown in FIG. 18.

Micelles can solubilize otherwise insoluble organic material by incorporating it within this hydrophobic interior. In the present active agent delivery system, the central core region of a micelle can dissolve otherwise totally water-insoluble active agents. Additionally, a cosolvent may be utilized, converting the simple micelle into a micro-emulsion or emulsion where the central core is made up of not just the lipid chains but also a second oily component along with the active agent.

Figure 17A:
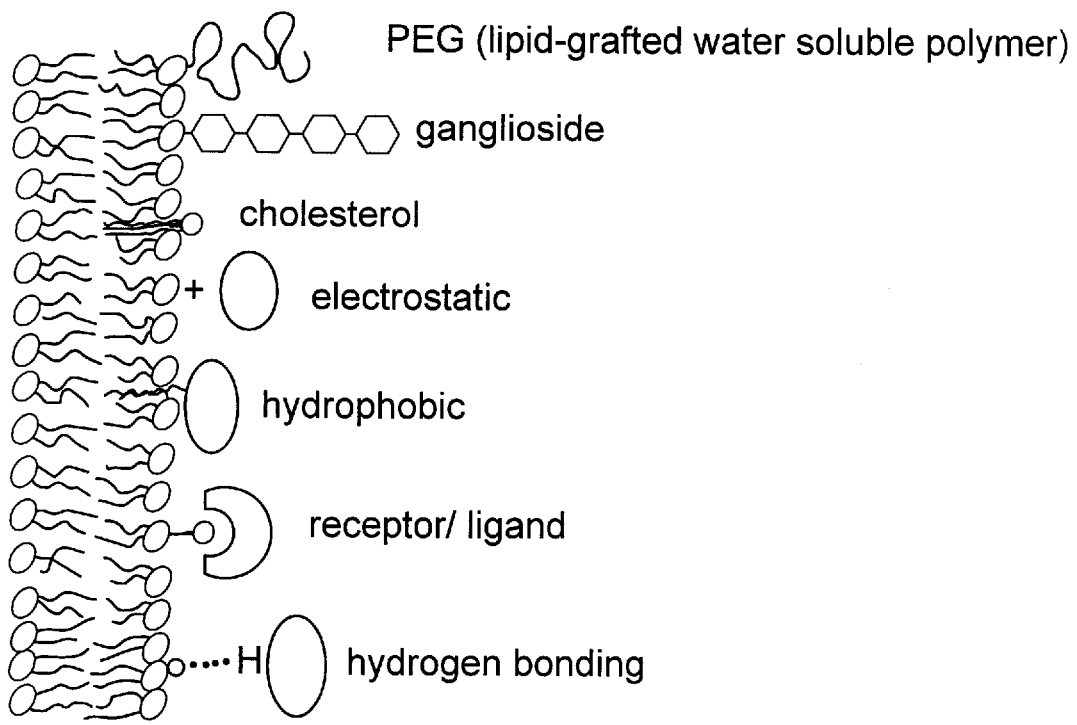
FIG. 17A depicts various lipid bilayer protection mechanisms, including the grafting of PEG or other water-soluble polymers to the lipids of the bilayer; gangliosides; cholesterol; other large macromolecules attached to the bilayer by electrostatic, hydrophobic, or receptor-ligand interactions.
Figure 17B:
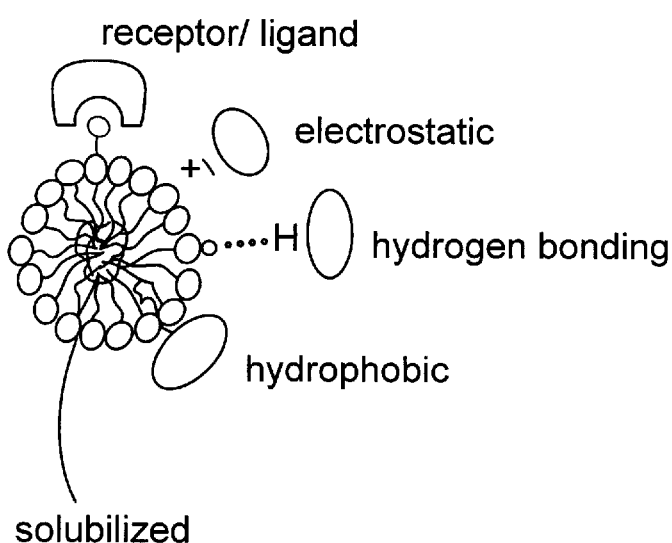
FIG. 17B depicts mechanisms by which an active agent can be bound to or within a micelle, including receptor-ligand binding, and electrostatic, hydrogen bonding, and hydrophobic interactions.

In the outer hydrocarbon chains, the last three or four carbon atoms are more nearly all-trans, and so are less liquid-like. This region is still fairly hydrophobic but will contain some water. It therefore represents a transitionary region between purely hydrophobic and purely water soluble regions. Molecules that enter this region must be fairly compatible with both the lipid chains and the solvated headgroup region and therefore are likely to be themselves amphipathic; amphiphilic active agents are likely to partition into this region of the micelle. Also, it is envisioned that by attaching a hydrophobic acyl chain to a given active agent molecule, the active agent could be anchored in the micelle as shown in FIG. 17b. The present inventors' studies with TAXOL® indicates that this is the region to which the TAXOL® molecules apparently bind. TAXOL® has a solubility of approximately 25 micromolar and so, although not completely water soluble, it is relatively water insoluble. The association of TAXOL® with a simple MOPC micelle increased the solubility of TAXOL® in direct proportion to the amount of lipid in suspension at a ratio of 1 mole TAXOL® per mole MOPC (data not shown). From spectroscopic absorption studies (data not shown) it appears that TAXOL® is in a similar water-soluble environment to that when it is alone in water solution, as opposed to some fairly hydrophobic internal micelle site. The molecule is in fact not soluble at all in alkanes such as hexane or tetradecane. A slight shift in the frequency of the absorption points to a micelle surface site for solubilization. Other non-polar agents such as Pt-Rhodamine complexes (known to be cytotoxic to tumors) may also be solubilized at this hydrophobic/hydrophilic boundary for use in chemotherapy.

With regard to the headgroup region of the micelle, the variability in chemical composition means that a range of surface characteristics for the micelle can be utilized, including charged, neutral and polymer-covered, so that the micelle can therefore anchor or associate a range of active agents that express counter structures (i.e., structures that have adhesive interactions with the micelle chemical moieties).

In ionic micelles, the headgroup region resembles a concentrated solution of electrolyte made up of localized headgroup charges and bound counter-ions forming a Stern layer. Therefore, active agents with charges opposite to that designed into the micelle will bind to the surface; both mono-charged and multi-charged molecules will bind. Multivalent molecules may aggregate the micelles and cross-link the micelle suspension, although this can be controlled and isolated to the interior of the liposome, e.g., by changing the internal pH once the active agent has been encapsulated. Precipitation of the active agent-micelle complex may add stability to the delivery vehicle, and may help prevent active agent leakage.

In non-ionic micelles, the headgroup region resembles a concentrated aqueous solution of solute (characterized by high osmotic pressure and water of hydration). A non-ionic, e.g. sugar, headgroup region would be fairly hydrated and, apart from a simple van der waals interaction, may not exert much of an attractive interaction with active agents. However, on interaction at this molecular surface of the micelle would involve hydrogen bonds. Some active agents of interest are oligonucleotides that act at their targeted site by hydrogen binding to the nucleotides of DNA or ENA. A range of drug molecules with hydrogen bond accepting or donating groups on them could thus be bound to complementary hydrogen bond donors and acceptors that comprise or are attached to the micelle forming lipids themselves.

If the headgroup contains a polymeric species (e.g., PEG lipid), then this region is characteristic of a bulk polymer solution. Therefore, any active agent that can be associated with a particular polymer, through one of several interaction mechanisms, could be incorporated in this polymer solution region, assuming the polymer was covalently or even electrostatically associated with the molecules that make up the micelle or the micelle surface. For example, charged polymers would be expected to bind oppositely charged active agents onto this shell; hydrogen bond donors will bind to hydrogen bond acceptors such as PEG (tannic acid precipitates PEG). Many active agent—polymer interactions will be possible; depending on the active agent, the appropriate polymer can be designed into the present active agent delivery system.

Figure 19:
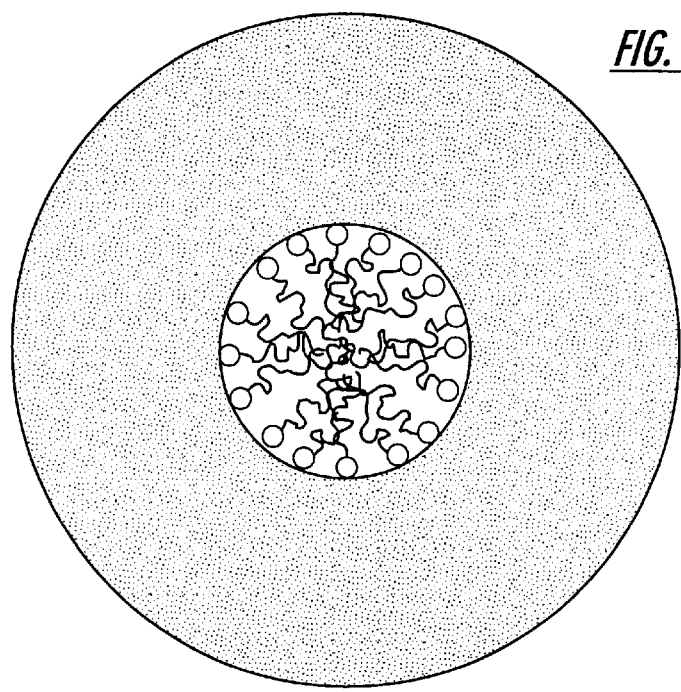
FIG. 19 is a schematic of a PEG-lipid micelle, where the shaded region represents a PEG-rich layer around the micelle created by PEG grafted onto the lipids of the micelle.

FIG. 19 shows a schematic of a PEG-lipid micelle (drawn approximately to scale). The hydrodynamic radius measured by dynamic light scattering, for micelles made from lipid-$PEG_{1900}$ is approximately 85Å to 100Å (Needham, (1992)). If the lipid acyl chains and phospholipid headgroup that comprise the core of the micelle take up 25Å of the total radius, then the polymer extends approximately 60–75Å out from this core, which is in close agreement with the polymer extension obtained for the same molecule in bilayers from x-ray diffraction experiments. (Needham, (1992)). These results indicate an extended, "brush-like" conformation for this non-adsorbing, but grafted, polymer.

For a charged micelles, the diffuse double layer extends beyond the Stern layer and occupies a region or aqueous solution around the micelle. Because amphiphilic molecules themselves are not fully extended they can "flex" in this rather fluid-like structure and cause a certain degree of surface roughness. Unlike lipid bilayers that form much "tighter" surfaces, water does in fact penetrate into the micelle hydrocarbon region. If we assume that water penetrates only a quarter of the way along the radius, we see that almost 60% of the micelle volume can be hydrated. Thus by providing a relatively "wet" surface, water soluble compounds may be (loosely) associated with the micelle.

Shape Considerations of Micelles and Bilayers

The micelles utilized in the present invention can be spherical or non-spherical (ellipsoid or even tubular). The association of active agents with the micelle forming surfactants may in some cases transform the shape of the original solubilizing micelle (as discussed below). That these different geometries exist s can be appreciated by considering the geometric requirements that aggregation number places on shape. Micelles formed by simple amphiphiles (e.g., $C_{12}$) are often small with an aggregation number of about 100 (molecules per micelle). Even these micelles are too large to be accommodated within a spherical geometry, given that the radius is limited by the extension length of the hydrocarbon chains. To increase volume with one dimension fixed, the micelles must take up an ellipsoidal shape. This aspect of micellar and other structures is discussed below.

Despite the strong driving force from the hydrophobic effect for surfactant molecules to aggregate into micelles, there is a limit to the size that can be achieved by packing the molecules into spherical or ellipsoidal geometries. This limit comes about because the surface to volume ratio always decreases as the volume increases; the surface area per hydrocarbon chain must decrease as the micelle size (volume) increases. For fixed molecular volume, a surfactant molecule can occupy a range of areas by changing its extended length, compressing or extending its (springy) hydrocarbon chain. At the fully extended length, the molecule has a minimum area at the interface; when this limiting area per molecule is reached, micelle size is restricted. Molecular shape thus plays a role in the formation of bilayers and inverted micelles as well as 'normal' micelles.

Since the association of active agents with the micelle-forming surfactants may make transformations in the shape of the original solubilizing micelle, it is necessary to describe the shape of a micelle and its transition to a bilayer or an inverted micelle structure. A sequence of shape and aggregation transitions can be identified between micelle, bilayer and inverted micelle structure, originating from the shape of the individual molecule; this approach uses simple steric and shape considerations to predict the aggregated state of surfactant molecules in aqueous solution (Israelachvili, 1985). Single-chain surfactants and double-chain lipids can self-assemble into a variety of structures in aqueous solution. A balance of forces determines the particular equilibrium configuration which can be changed by changes in environmental conditions such as the temperature, ph, and electrolyte or lipid concentration. In the present invention, this shape hypothesis may be extended to include any changes in molecular shape that may occur upon drug binding or association with the individual surfactant molecules, that transforms them from, for example, a wedge shape to a cylindrical shape, and therefore induces a transformation from a micelle to a tubular micelle and even to a bilayer.

In this treatment, a balance between attractive (hydrophobic—tending to reduce area per molecule) and repulsive (inter-headgroup—tending to increase area per molecule) interactions determines an optimum area per headgroup ($a_o$) at which the total interfacial free energy per molecule ($\mu^o N$) in an aggregate is a minimum. The energy varies parabolically (and elastically) about a minimum at a certain headgroup area. The most favored structure (micelle, bilayer or inverted micelle) depends on this minimum area, the incompressible volume of the hydrocarbon chains and the maximum effective length (the critical chain length $l_c$) that the hydrocarbon chains can assume.

For lipids of the optimal area $a_o$, hydrocarbon volume v and critical chain length $l_c$, the value of the dimensionless parameter, $v/a_o l_c$, will determine whether the lipids assemble into spherical micelles ($v/a_o l_c < 1/3$); non-spherical micelles ($1/3 < v/a_o l_c < 1/2$); vesicles or bilayers ($1/2 < v/a_o l_c < 1$); or inverted micelles ($v/a_o l_c < 1$). Each of these structures corresponds to the minimum sized aggregate in which the lipids have minimum free energy, i.e., $a = a_o$.

In spherical micelles, $a_o$ must be sufficiently large and the hydrocarbon volume must be sufficiently small such that the radius of the micelle will not exceed the critical chain length $l_c$; thus for a micelle of radius R, the mean aggregation number M is:

$$M = \frac{4\pi R^2}{a_o} = \frac{4\pi R^3}{3v}$$

namely,

R=3v/$a_o$ so that, only if $R \leq l_c$, i.e., $v/a_o l_c \leq 1/3$ will the amphiphiles pack into a spherical micelle. For example, the parameters for SDS in water are: $l_c$=17Å, $a_o$=62Å$^2$, v=350Å$^3$ and SDS forms a relatively spherical micelle, $v/a_o l_c \approx 1/3$.

Figure 10:
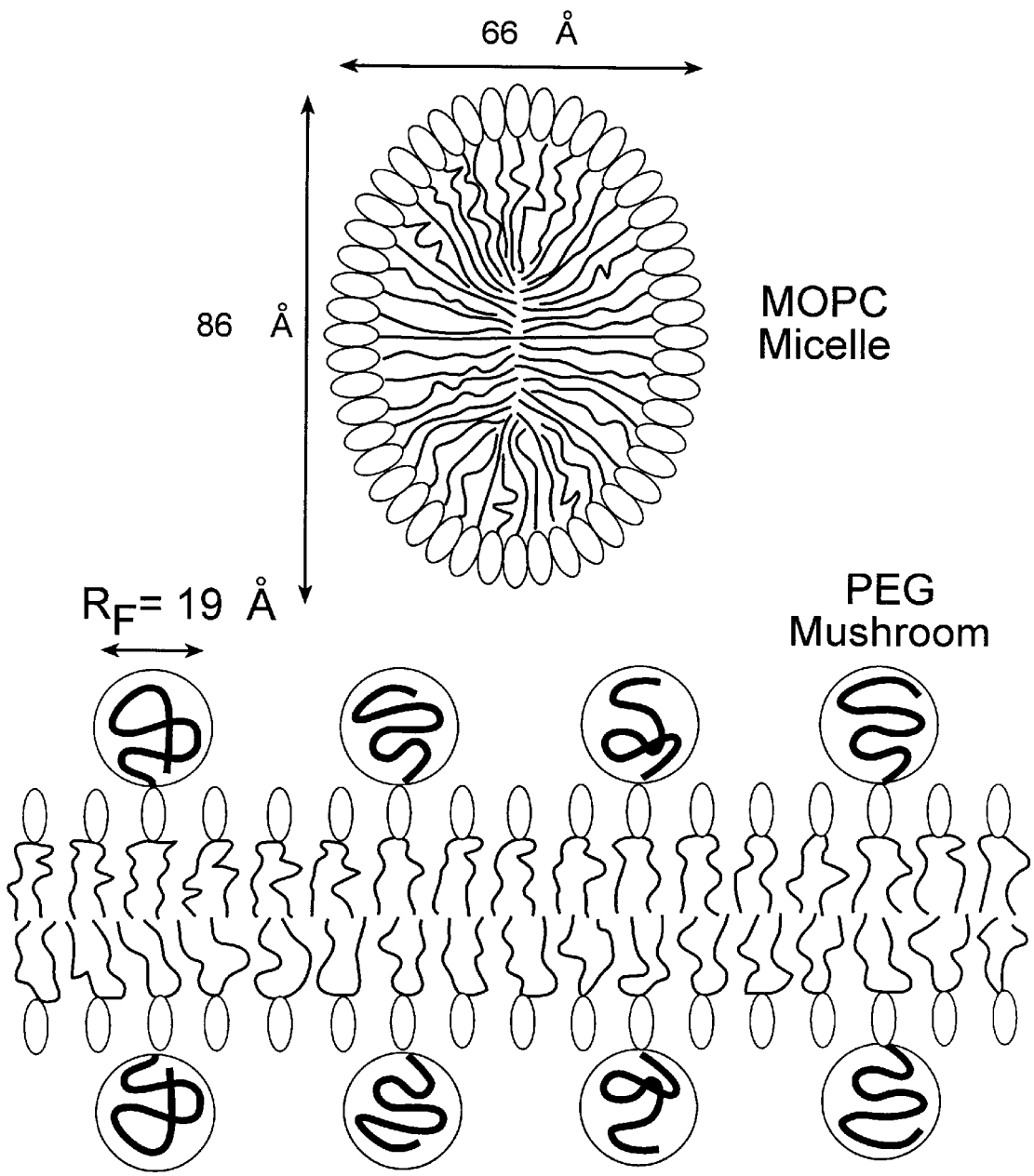
FIG. 10 is a scale drawing of a MOPC micelle at the surface of a PEG-grafted bilayer (PEG-lipid density of approximately 5 mol %), with micelle dimensions (66Å× 86Å) calculated as described herein and size of each PEG "mushroom" ($R_F$=19Å) calculated from the Flory radius as described herein.

Similarly, non-spherical micelles exist if the $v/a_o l_c$ ratio is between 0.33 and 0.5. For MOPC, the parameters are $l_c$=33Å, $a_o$=44Å$^2$; MOPC forms an elliptical micelles as shown in FIG. 10. These slight changes in molecular shape (projected area of acyl chain and chain length) might also come about if there is a strong association between the MOPC molecule and a relatively rigid hydrophobic, but still amphipathic, active agent. Thus active agent incorporation into a spherical micelle might change it into an ellipse or even a cylinder or disc. An example of mixed micelle is the combination of a small surfactant (high cmc) such as glycocholate, and a larger two chain surfactant such as a phospholipid (very low cmc). At certain ratios these two molecules will combine to form the mixed micelle, in which the high cmc surfactant that prefers to pack as a spherical surface occupies the edges of a low cmc lipid that prefers to be flat.

In the present invention, three aspects of the bilayer component that forms the vesicle membrane require consideration: molecular shape and bilayer structure; capacity of the bilayer to dissolve active agents; and additional mechanisms for protecting the bilayer from disruption by micelles.

Molecular shape and bilayer structure: when the shape discussion (above) is extended to the use of relatively cylindrical molecules, then for many phospholipids the value of $v/a_o l_c$ must lie close to 1 and it is found that the lipids do form bilayers and cannot pack into small micellar structures because their double hydrocarbon chains are too bulky to fit into this spherical geometry while maintaining surface area at its optimum value. Bilayer-forming lipids have a slightly truncated-conical or cylindrical shape. The two hydrocarbon chains per molecule project almost the same area at the interface as the phospho-headgroup. For example, for egg lecithin, $a_o$=72Å$^2$, v=1063Å$^3$ and $l_c$=17.5Å, so that $v/a_o l_c$=0.84. Interestingly, the grafting of a PEG polymer onto a double chained lipid stabilized the micellar structure presumably by increasing the effective headgroup area. Consequently, there is a limiting concentration of PEG-lipids that can be accommodated in a bilayer phase before phase separation occurs.

As in the micelle, all unfavorable water-hydrocarbon contact is prevented by the oriented packing of the surfactants into bilayers, except that simple lamellar sheets would present edges of hydrocarbon exposure. This forbidden exposure is eliminated by the lamellar sheet forming a spherical vesicle.

The limits to lipid bilayer curvature determine the minimum radius of the liposome and again this depends on molecular shape, which the presence of bilayer soluble active agents can change. For a bilayer to curve into a small vesicle, the lipids in the outer monolayer must be able to pack, on average, as truncated cones which requires that $v/a_o l_c < 1$. The smallest radium $R_c$ that a vesicle may form without forcing the headgroup area in the external monolayer to exceed $a_o$, or the lipid chain to exceed $l_c$, is given by:

$$R_c \approx \frac{l_c}{(1 - l_c/a_o l_c)}$$

For example, for egg lecithin, $R_c \approx 11$ nm (which corresponds to 3000 molecules per liposome). Thus structures of a minimum size to permeate the leaky vasculature of solid tumors can be prepared.

Lipid bilayers have the capacity to dissolve active agents, and is an excellent sink for the uptake of insoluble and partially insoluble molecules. This partitioning, though, is limited to relatively small molecules that can "fit" into the highly anisotropic structure of the bilayer, either by filling up the midplane, and/or by intercalating between the acyl chains. Thus liposomes can act as active agent delivery systems for water insoluble or poorly soluble agents by carrying them, not in the aqueous interior, but in the bilayer itself. Attachment of molecules of active agent to the surface of a liposome (as described above for micelles) would utilize water soluble active agents that have a colloidal or receptor-ligand interaction with the bilayer. However, the available volume and surface area of a liposome bilayer is relatively small compared to a micelle-filled interior as described herein, as so active agent capacity may be insufficient for most purposes. Nevertheless the liposome bilayer provides a volume in which active agents can be carried, and presents a range of binding and attachment opportunities for creating a "protected surface" as discussed below.

Several mechanisms are proposed herein to protect liposome bilayers from the disruptive effects of micelle contact. The present inventors have shown that the inclusion in the bilayer of polymer-grafted lipids protects the liposome from membrane disruptive effects of micelles contained within. Additional methods of attaching protective molecules to a liposome bilayer surface to provide protection are depicted in FIG. 17a, including the grafting of PEG or other water soluble polymers to lipids of the bilayer; incorporation of cholesterol in the bilayer; and attachment of other large macromolecules to the lipid bilayer via electrostatic, hydrophobic, or receptor-ligand interactions. Such macromolecules include proteins, polymers, and even the desired active agent itself.

Protected Membranes

Given the energetic and kinetic model of micelle/membrane fusion described herein, protective molecules other than polymers can also be used to formulate liposome membranes capable of containing active agents aggregated with lipid surfactants. In other words, protective molecules which extend beyond or above the surface of the liposome membrane would interfere with and inhibit micelle/membrane fusion in the same general manner as PEG, as discussed above. Where a liposome contained micellar preparations of an active agent, for example, protective molecules on the interior of the liposome membrane would inhibit micelle/membrane fusion and contribute to the stability of the liposome.

Gangliosides attached to the membrane surfaces would provide barriers to micelle fusion; for example, short gangliosides containing about four sugar moieties would provide barriers to micelle/membrane fusion. Other molecules of approximately the same size as micelles contained within a liposome could also be utilized to block micelle/membrane binding. Such molecules include, for example, globular proteins such as albumin, and filamentous proteins or peptides. Such molecules could, for example, be attached to the membrane by hydrostatic forces or, if a molecule with an amphipathic "tail" is used, the amphipathic tail could be used to attach the molecule to the membrane. Additionally, one member of a binding pair of molecules could be attached to the liposome membrane so that, when the liposome is exposed to the other member of the binding pair, the conjoined binding pair molecules provide a barrier to membrane/micelle fusion (e.g., a receptor molecule may be attached to the liposome membrane which, by itself, may not inhibit membrane/micelle fusion, but when associated with its ligand the combined receptor-ligand complex is able to inhibit membrane/micelle fusion). Molecules suitable for use as barriers to membrane/micelle fusion may also act as active agents, including as therapeutic agents.

Drugs and Active Agents

Active agents suitable for use in the present invention include therapeutic drugs and pharmacologically active agents, nutritional molecules, cosmetic agents, diagnostic agents and contrast agents for imaging. As used herein, active agent includes pharmacologically acceptable salts of active agents. Suitable compounds are lipophilic or amphipathic molecules (i.e., water insoluble or substantially water insoluble molecules) which can be prepared as micellar formulations or as emulsions. Suitable therapeutic agents include, for example, antineoplastics, antitumor agents, antibiotics, antifungals, antivirals, anthelminthic, and antiparasitic compounds.

In treating tumors or neoplastic growths, suitable compounds may include anthracycline antibiotics (such as doxorubicin, daunorubicin, carinomycin, N-acetyladriamycin, rubidazone, 5-imidodaunomycin, and N-acetyldaunomycin, and epirubicin) and plant alkaloids (such as vincristine, vinblastine, etoposide, ellinticine and camptothecin). Other suitable agents include paclitaxel (TAXOL®; a diterpenes isolated from the bark of the yew tree and representative of a new class of therapeutic agents having a taxane ring structure) and docetaxol (taxotere); mitotane, cisplatin, and phenesterine.

Anti-inflammatory therapeutic agents suitable for use in the present invention include steroids and non-steroidal anti-inflammatory compounds, such as prednisone, methylprednisolone, paramethazone, 11-fludrocortisol, triamciniolone, betamethasone and dexamethasone, ibuprofen, piroxicam, beclomethasone; methotrexate, azaribine, etretinate, anthralin, psoralins; salicylates such as aspirin; and immunosuppresant agents such as cyclosporine. Antiinflammatory corticosteroids and the antiinflammatory and immunosuppressive agent cyclosporine are both highly lipophilic and are suited for use in the present invention.

Additional pharmacologic agents suitable for use in liposomes of the present invention include anesthetics (such as methoxyflurane, isoflurane, enflurane, halothane, and benzocaine); antiulceratives (such as cimetidine); antiseizure medications such as barbituates; azothioprine (an immunosuppressant and antirheumatic agent); and muscle relaxants (such as dantrolene and diazepam).

Methods of preparing lipophilic drug derivatives which are suitable for liposome or micelle formulation are known in the art (see e.g., U.S. Pat. No. 5,534,499 to Ansell, describing covalent attachment of therapeutic agents to a fatty acid chain of a phospholipid). A micellar formulation of taxol is described in Alkan-Onkyuksel et al., *Pharmaceutical Research*, 11:206 (1994).

Imaging agents suitable for use in the present liposome preparations include ultrasound contrast agents, radiocontrast agents (such as radioisotopes or compounds containing radioisotopes, including iodo-octanes, halocarbons, and renografin), or magnetic contrast agents (such as lipid soluble paramagnetic compounds). Amphipathic chelating agents which can be physically incorporated into lipid membranes are known in the art for use in contrast agents. See, e.g., Grant et al., *Magn. Res. Med.* 11:236 (1989); Kabalka et al., *Magn. Res. Med.* 8:89 (1988). However, to provide a useful image, liposomes containing a high molar content of the chelating agent may be required; where the chelating agent is incorporated into the liposome bilayer, unstable lipid bilayers may result. Liposomes according to the present invention may be prepared containing micellized chelating agents; such liposomes provide concentrated chelating agent in a stable liposome. Amphipathic polychelating compounds suitable for binding to micelles are known in the art (U.S. Pat. No. 5,534,241 to Torchilin et al.).

Nutritional agents suitable for incorporation into liposomes of the present invention include amino acids, sugars, proteins, carbohydrates, fat-soluble vitamins, or fat. Combinations of nutritional agents are also suitable.

Preparation of Micelles Containing Active Agents

Active agents contained within liposomes of the present invention are in solubilized form. Aggregates of surfactant and active agent (such as emulsions or micelles containing the active agent of interest) are entrapped within the interior space of liposomes according to the present invention. The surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

As used herein, active agents "aggregated" with lipid surfactant refers to active agents which have been solubilized with a lipid surfactant, and includes both emulsions of active agents and micellar preparations of active agents. As used herein a "micellar form" or "micellar preparation" of an active agent refers to active-agent containing micelles. See, e.g., Alkan-Onyuksel et al., *Pharmaceutical Research* 11:206 (1994) (describing micellar formulation of TAXOL®). The active agent may be associated with a micelle either on the micelle surface or within the micelle interior, depending on the water-solubility of the active agent.

The mixtures of surfactant and active agent may further contain a co-surfactant or a volatile dispersing agent (for example, dimethyl sulphoxide (DMSO)), and may be suspended in an aqueous medium such as water or saline solution.

Administration and Size of Liposomes

In a first aspect of the present invention, liposomes are delivered into the bloodstream. An additional aspect comprises subcutaneous administration of liposomes according to the present invention (see, e.g., published PCT application WO 94/26251).

Where treatment of a tumor or neoplasm is desired, effective delivery of a liposome-encapsulated active agent via the bloodstream requires that the liposome be able to penetrate the continuous (but "leaky") endothelial layer and underlying basement membrane surrounding the vessels supplying blood to a tumor. Liposomes of smaller sizes have been found to be more effective at extravasation into tumors through the endothelial cell barrier and underlying basement membrane which separates a capillary from tumor cells. See, e.g., U.S. Pat. No. 5,213,804 to Martin et al. However, the limited drug-carrying capacity of conventional liposome preparations limits their effectiveness for such purposes.

As used herein, "solid tumors" are those growing in an anatomical site other than the bloodstream (in contrast to blood-borne tumors such as leukemias). Solid tumors require the formation of small blood vessels and capillaries to nourish the growing tumor tissue.

In accordance with the present invention, the anti-tumor or anti-neoplastic agent of choice is entrapped within a liposome according to the present invention; the liposomes are formulated to be of a size known to penetrate the endothelial and basement membrane barriers. The resulting liposomal formulation can be administered parenterally to a subject in need of such treatment, preferably by intravenous administration. Tumors characterized by an acute increase in permeability of the vasculature in the region of tumor growth are particularly suited for treatment by the present methods. The liposomes will eventually degrade due to lipase action at the tumor site, or can be made permeable by, for example, thermal or ultrasonic radiation. The active agent is then released in a bioavailable, transportable solubilized form.

Where site-specific treatment of inflammation is desired, effective liposome delivery of an active agent requires that the liposome have a long blood half-life, and be capable of penetrating the continuous endothelial cell layer and underlying basement membrane surrounding blood vessels adjacent to the site of inflammation. Liposomes of smaller sizes have been found to be more effective at extravasation through the endothelial cell barrier and into associated inflamed regions. See, e.g., U.S. Pat. No. 5,356,633 to Woodle et al. However, the limited drug-carrying capacity of conventional small liposome preparations has limited their effectiveness for such purposes.

In accordance with the present invention, the anti-inflammatory agent of choice is entrapped within a liposome according to the present invention; the liposomes are formulated to be of a size known to penetrate the endothelial and basement membrane barriers. The resulting liposomal formulation can be administered parenterally to a subject in need of such treatment, preferably by intravenous administration. Inflamed regions characterized by an acute increase in permeability of the vasculature in the region of inflammation are particularly suited for treatment by the present methods.

It will further be appreciated that the long-circulation time of liposomes according to the present invention allow delivery of anti-infective agents to sites of infection, via the bloodstream. The use of liposomes containing a vesicle-forming lipid derivatized with a hydrophilic polymer, and having sizes ranging between 0.07 and 0.2 microns, to deliver therapeutic agents to sites of infection is described in published PCT patent application WO 93/19738. In accordance with the present invention, the anti-infective agent of choice is prepared in a solubilized form and entrapped within a liposome according to the present invention, and the resulting liposomal formulation can be administered parenterally to a subject in need of such treatment, preferably by intravenous administration.

The size of liposomes in a preparation may depend upon the active agent contained therein and/or the intended target. Liposomes of between 0.05 to 0.3 microns have been reported as suitable for tumor administration (U.S. Pat. No. 5,527,528 to Allen et al.) Sizing of liposomes according to the present invention may be carried out according to methods known in the art, and taking into account the active agent contained therein and the effects desired (see, e.g., U.S. Pat. No. 5,225,212 to Martin et al; U.S. Pat. No. 5,527,528 to Allen et al). A preferred embodiment of the present invention is a liposome of less than 10 microns in diameter, or a liposome preparation containing a plurality liposomes of less than 10 microns in diameter. In a further preferred embodiment of the present invention, liposomes are from about 0.05 microns or about 0.1 microns in diameter, to about 0.3 microns or about 0.4 microns in diameter. Liposome preparations may contain liposomes of different sizes.

Liposome Preparation

Liposomes according to the present invention may be prepared by any of a variety of techniques that are known in the art. See, e.g., U.S. Pat. No. 4,235,871; Published PCT applications WO 96/14057; New RRC, *Liposomes: A practical approach,* IRL Press, Oxford (1990), pages 33–104; Lasic DD, *Liposomes from physics to applications,* Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Use of Polymer Gel Beads

In a further embodiment of the present invention, the preparation of active agent and surfactant is loaded into a micrometer or nanometer sized polymer gel bead, which is then encapsulated by a lipid bilayer containing polymer-grafted lipids as described above. The protective lipid bilayer prevents immediate dispersion of the micelle formulation. Cationic molecules will preferentially load into anionic polymer gel matrices and vice versa. A certain proportion of low CMC, micelle-compatible, ionic surfactants (along with lysophosphatidylcholine, polymer-derivatized lipid, or other amphipathic solubilizing agents) will confer on the active agent-containing micelle a net charge that is opposite to the gel charge. See Philippova et al., *Macromolecules* 29:2822 (1996). A preparation of active agent that associated with a gel is said to be "carried by" or "contained within" the gel.

Additional Controlled Delivery Techniques

The derivatized lipid components of liposomes according to the present invention may additionally include a labile lipid-polymer linkage, such as a peptide, ester, or disulfide linkage, which can he cleaved under selective physiological conditions, such as in the presence of peptidase or esterase enzymes or reducing agents. Use of such linkages to couple polymers to phospholipids allows the attainment of high blood levels of such liposomes for several hours after administration, followed by cleavage of the reversible linkages and removal of the polymer from the exterior liposome bilayer. The polymer-less liposomes are then subject to rapid uptake by the RES system. See, e.g.., U.S. Pat. No. 5,356,633 to Woodle et al).

Additionally, liposomes according to the present invention may contain non-polymer molecules bound to the exterior of the liposome, such as haptens, enzymes, antibodies or antibody fragments, cytokines and hormones (see, e.g., U.S. Pat. No. 5,527,528 to Allen et al), and other small proteins, polypeptides, or non-protein molecules which confer a particular enzymatic or surface recognition feature to the liposome. See published PCT application WO 94/21235. Surface molecules which preferentially target the liposome to specific organs or cell types are referred to herein as "targetting molecules" and include, for example, antibodies which target the liposome to tumor cells bearing specific antigens. Techniques for coupling surface molecules to liposomes are known in the art (see, e.g., U.S. Pat. No. 4,762,915 to Kung et al).

Thermal Sensitivity

Thermal or pH release characteristics can be built into liposomes by incorporating thermal sensitive or pH sensitive lipids as a component of the lipid bilayer (e.g., dipalmitoyl-phosphatidylcholine:distearyl phosphatidylcholine (DPPC:DSPC) based mixtures. Use of thermal or pH sensitive lipids allows controlled degradation of the lipid vesicle membrane.

A further aspect of the present invention is the use of temperature sensitive hydrophilic polymers attached to a vesicle-forming lipids as part of the liposome membrane bilayer, to provide controlled release of the active agent contained within the liposome. Such liposomes incorporate a hydrophilic polymer with a cloud temperature ($t_{p+}$) of approximately 40° C. The cloud temperature is the temperature at which the water solubility of the polymer is reduced and, for free polymer, is indicated in a solution of the polymer by clouding of the solution. When a liposome according to the present invention comprises a polymer with a cloud temperature within physiologic range (i.e., within the range of temperatures that can be withstood by living cells), subjecting the liposome to the cloud temperature causes the polymer to undergo the precipitation reaction and its barrier properties (i.e., the ability to prevent micelle/membrane fusion) are compromised, leading to membrane instability and release of the liposome contents. Localized hyperthermic treatments at the desired site of active agent administration trigger liposome degradation and active agent release at the desired site.

The cloud temperature can show some dependence on polymer molecular weight, but approaches a limiting value as molecular weight (M) approaches infinity; this temperature is termed the ideal, Flory, or theta temperature. Polyethylene glycol has a theta temperature of about 96° C., out of physiologic range. A copolymer of polyethylene glycol and polypropylene oxide (PEG/PO 67/33 copolymer) has a cloud temperature of about 48° C. One skilled in the art could alter the PEG/PO mixture and molecular weight to achieve a $t_{p+}$ of about 40° C. Polyvinylacetate-polyvinylalcohol (PVAC-VAL) copolymers have $t_{p+}$ temperatures ranging from more than 90° C. to less than 0° C. A PVAC-VAL 23/77 mixture would be expected to have a cloud temperature of about 40° C. The water soluble polymer polyvinylmethyloxazolidone (PVMO) has a cloud point at about 40° C., and when derivatized onto a vesicle-forming lipid would provide a simple polymer lipid system that undergoes transition in the physiologic hyperthermic range.

Membranes Containing Cholesterol

In another embodiment of the present invention, in liposomes entrapping active agents aggregated with a lipid surfactant, the liposome membrane is Protected against the disruptive effects of the surfactant contained therein by the inclusion of cholesterol in the liposome membrane. Cholesterol is a bilayer-compatible sterol that is found in many naturally-occuring biological membranes. The protective effect of cholesterol is demonstrated in Example 7, below.

The present inventors have determined that the inclusion of even small amounts of cholesterol (from 3 mol % up to saturation at approximately 60 mol %) in lipid bilayers confers a "protective" effect to high (1 mM) concentrations of MOPC; in comparison, PEG coatings failed to protect against dissolution at 500 micromolar MOPC (data not shown).

Although not wishing to be held to a particular theory of action, this unexpected property of cholesterol-containing membranes is thought by the present inventors to occur through a different mechanism than that for membrane bilayers containing polymer grafted lipids, since cholesterol does not exert any steric barrier at the surface of the bilayer. Previous studies have indicated that the inclusion of cholesterol increases the mechanical stability of lipid membranes, for example, increasing the mechanical strength of a thin 2 molecule-thick bilayer to that equal to an equivalent thickness of polyethylene (Needham and Zhelev, In: Vesicles, M. Rosoff (Ed.), Marcel Dekker Inc., New York (1996), pp. 373–444). Such results suggest that cholesterol simply increases the bilayer cohesion (reduces surface density and makes the bilayer interface tighter) and so prevents micelles from being taken up by the bilayer. Such a mechanism would exhibit a concentration effect: as more cholesterol was added to the membrane fewer micelles would fuse to it because more of the membrane would be condensed. In other words, it would be expected that uptake by the membrane would be dependent on the area fraction occupied by cholesterol. The present results contradict such an interpretation, as 3 mol % cholesterol is not sufficient to change the elastic modulus of the membrane by any significant amount, to provide a global stiffening phenomenon. Yet the present results show that 3 mol % cholesterol in a liposome membrane is as effective as 60 mol % in preventing micelle/membrane fusion, thus there is no area dependence. The presently demonstrated effect of cholesterol on bilayer membranes is a "critical" phenomenon, in which micelle-membrane fusion is inhibited at (and above) a particular critical concentration of cholesterol. Liposomes according to the present invention may contain from about 2 mol %, 3 mole %, 5 mole % or even 10 mole % of cholesterol, up to about 15 mole %, 20 mole %, 40 mole % or even 60 mole % of cholesterol.

While not wishing to be held to a single theory regarding the effects of cholesterol on lipid bilayer membranes, a proposed mechanism of fusion is provided herein. First, thermodynamic concepts (that do not rely on mechanistic interpretations) must be considered. At the CMC the chemical potential of monomer in micelle and in solution is equal; they are in equilibrium. The introduction of a bilayer perturbs this equilibrium by presenting a fresh phase in which monomer partitioning can occur. Presumably this is at a lower energy or it would not occur; an activation energy for the process could involve some intermediate transition state complex or barrier provided by a polymer such as PEG.

Figure 11A:
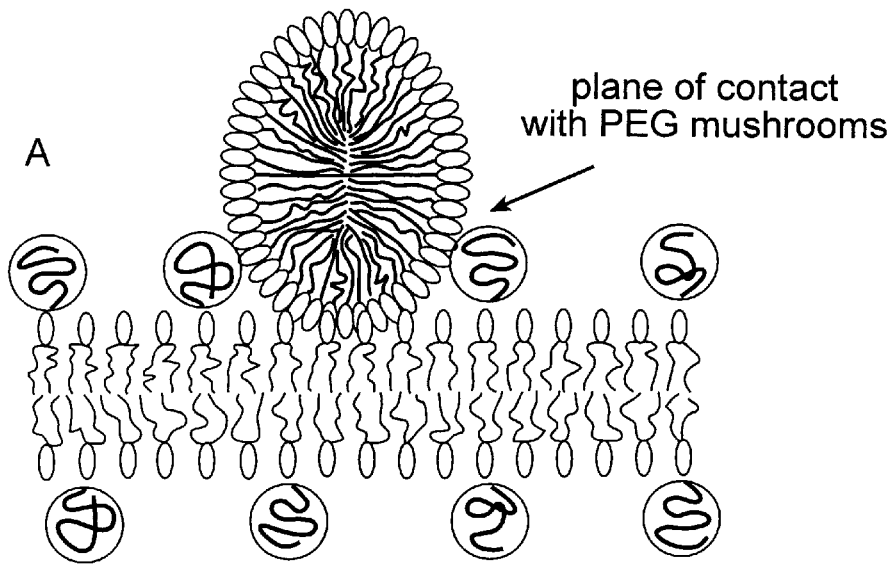
FIG. 11A is a schematic showing a MOPC micelle at a lipid bilayer interface, where the lipid bilayer contains a low surface concentration of grafted PEG which just allows the micelle to come into intimate contact with the bilayer interface (i.e., headgroup intermixing). The micelle plane of contact with the PEG "mushrooms" is indicated by an arrow.
Figure 11B:
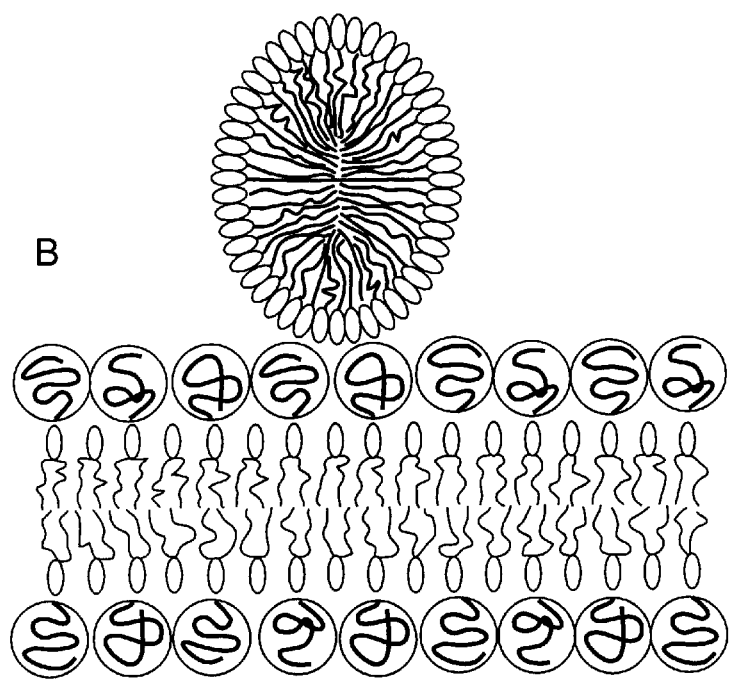
FIG. 11B is a schematic showing a MOPC micelle at a lipid bilayer interface, where the lipid bilayer contains a high surface concentration of grafted PEG (approximately 20 mol %), which completely excludes the micelle from the bilayer surface.

Mechanistically, this would look different for bare and polymer-covered surfaces. In a polymer covered lipid bilayer, the activation energy is (as has been described above) the work required to denude the bilayer surface of polymer and is derived to the surface pressure that the polymer creates at the interface (FIGS. 11A and 11B). The micelle meets this activation energy at approximately 25Å from the bilayer surface, i.e., when it encounters the extended polymer interface.

Figure 15A:
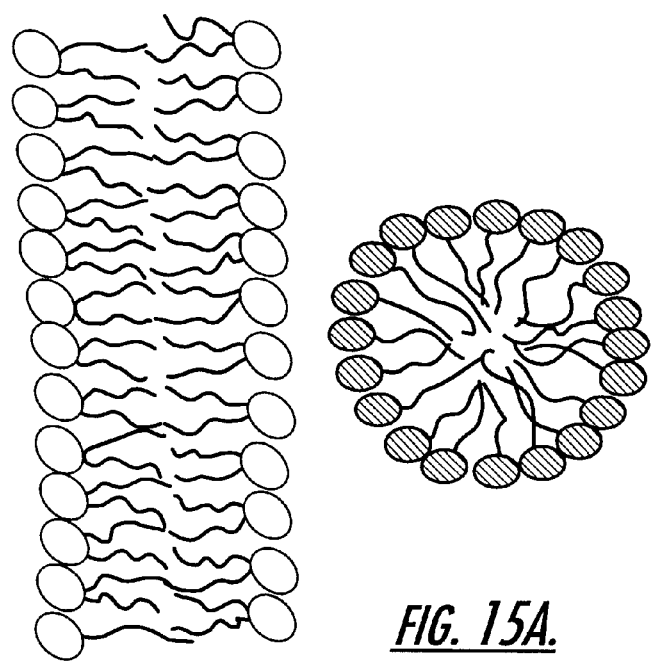
FIG. 15A depicts a micelle approaching a bare membrane, where micelle lipid headgroups are shaded and membrane bilayer lipid headgroups are unshaded.
Figure 15B:
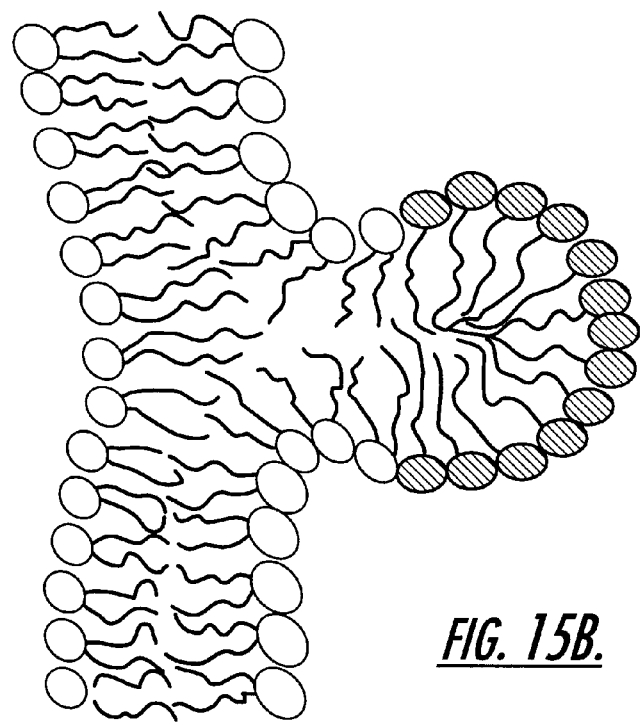
FIG. 15B depicts the transition state complex for a micelle "fusing" with a lipid bilayer. This fusion of two stable structures is energetically favorable but requires the surmounting of an activation energy barrier, which is proposed to be due to the formation of a transition state complex in which the normally convex micelle and the normally flat bilayer must form a concave stalk. Phospholipids are depicted as forming a stalk by splaying their acyl chains and creating a concave curature in which, temporarily, the headgroup to acyl chain ratio is reduced.

Even for the "bare" lipid bilayer surface, we expect that there will be some activation energy barrier for the formation of the transition state complex, where the bilayer lipids and micelle lipids mix. Clearly this activation energy barrier must not be too large compared to the available thermal energy ($k_BT$, 2.5 kJ/mol), since micelles readily fuse with the membrane. FIG. 15 shows a; sketch of the transition state complex for a micelle approaching a bare membrane. The micelle is like a small liquid drop, and therefore curvature of the lipid interfaces involved in the transition state complex is expected, and suggests a complex involving the formation of some transitionary bridge or "stalk". The curvature that is required to make such a fusion "stalk" is in the wrong direction for lysolipids to accomodate—their large headgroup/acyl chain area ratio makes them prefer to opposite convex curvature (as in the micelle surface). Thus, for the fusion transition state complex to form, lipids from the bilayer must make the "stalk". Now, as shown herein, the exposure of a bilayer vesicle to a lysolipid solution leads to the rapid uptake of monomer, i.e., even though micelles can be excluded by some mechanism, by the time the micelle reaches the bare membrane, the bilayer will not be simply composed of just the original phospholipids but will also contain approximately 5 mol % MOPC. Before we can discuss how cholesterol may reduce the tendency of a micelle to fuse with the bilayer (i.e., make the formation of a transition state complex more unlikely), the kinds of interactions that cholesterol has with phospholipids (and with their acyl chains in particular) must be considered.

Cholesterol has a very strong and specific interaction with phospholipids (and phospholipid acyl chains in particular). Changes in the chemical structure of cholesterol results in the loss of the specific condensing and strengthening effect that cholesterol imparts to lipid bilayers, whether the changes are at the "interfacial-anchoring" —OH or are the addition of keto oxygens (as in ketocholestanol, see Simon et al., Biophys. J. 61:786 (1992)) or $CH_3s$ to the ring structure. Thus cholesterol would appear to interact strongly by positioning its planar ring structure in direct contact with the lipid acyl chains such that the most adjacent chain is relatively planar and in a largely all trans state. For cholesterol to interact with a normal di-chain phospholipid, it would perturb one chain more than another, so that the two molecules form a purported short-lived complex. The lysolipids only have one chain, and thus cholesterol is proposed to interact preferentially with lysolipid (as the lysolipid is taken up by the membrane) to form an association complex with this molecule. In any event, cholesterol tends to stiffen local acyl chains (of both phospholipid and lysolipid) making them less able to form a curved interface, and therefor would be expected to oppose the formation of any transition state "stalk" structure.

Following from the above discussion, a membrane composed of 3 mol % cholesterol and having taken up 5 mol % lysolipid from surrounding solution would contain approximately 3 mol % of the two molecule (cholesterol-lysolipid) complex; i.e., in the membrane, 1 molecule in every 30 or so would be stiff and resist curvature. Thus if 100 molecules of lipid from the membrane are required to form the fusion stalk defect then three of the 100 molecules will oppose the required curvature. This seems a small number in relation to the number of normal dichain lipids, but the dichain lipids themselves are not inclined to form the concave curvature either, and so a slight perturbation caused by a few stiff cholesterol molecules is proposed to be enough to affect membrane fusion, and explains the observed threshold effect for cholesterol contained in membranes.

The surprising results obtained by the present inventors show that the inclusion of relatively small amounts of cholesterol in a liposome membrane (amounts too small to create any global stiffening of the membrane) are sufficient to inhibit fusion of micelles with the liposome membrane. It is proposed by the present inventors that the cholesterol perturbs a transition state complex that facilitates micelle/membrane fusion (and ultimately membrane dissolution). These results further indicate that any other molecule that enhances convex curvature (i.e., the normal curvature of a lipid bilayer membrane) and opposes concave curvature (i.e., curvature opposite that found in lipid bilayer membranes) would, like cholesterol, inhibit micelle membrane fusion when the molecule is contained in the lipid bilayer membrane at or above the threshold amount. Suitable molecules would include additional micelle forming surfactants, lipids or polymers, such as short diblock copolymers of polypropylene oxide-polyethylene oxide (PPO-PEO).

Optimization of Drug Carrying Capacity of Liposomes

As discussed above, surfactant micelles are able to suspend (co-dissolve) molecules with poor water solubility, but micelles rapidly break up in the blood stream due to the transfer of micelle surfactants to cell membranes, and the dilution and dispersal of surfactant as a monomer. The present invention provides a way to encapsulate a drug-laden micelle suspension inside a liposome. The present invention provides a lipid membrane composition that stabilizes the lipid bilayer membranes, so that the membrane remains intact in a suspension of surfactant micelles that would otherwise dissolve the liposome membrane.

The present invention provides compositions and methods of assembly of lipid and surfactant materials such that normally water-insoluble drugs, such as TAXOL®, can be suspended in aqueous solution at concentrations far in excess of their aqueous solubility limit. In one embodiment, liposomes contain the drug in the liposome membrane facilitated by co-inclusion of lysolipid. The drug and lipid components are co-dissolved in a suitable solvent; after evaporation and hydration in aqueous buffer, liposomes are formed that carry the drug in the liposome membrane. The lipid component solubilizes the drug, which is then contained within (or adsorbed onto) the liposome membrane. An exemplary liposome containing TAXOL® as the active agent carried by the liposome membrane is described herein. Amounts of TAXOL® in such liposomes prepared according to the present invention can reach levels of at least about 10 mole %, 11 mol %, 12 mol %, 13 mol %, 14 mol %, 15 mol %, 16 mol %, 17 mol % or more, relative to SOPC in the membrane.

A further embodiment of the present invention provides liposomes that contain the drug within the liposome interior; the drug is solubilized in a micelle suspension of a suitable surfactant. This surfactant-drug suspension is then encapsulated in a lipid formulation by hydrating a pre-equilibrated lipid film (equilibrated with both drug and surfactant) with the micelle suspension and extruding the mixture to form large unilamellar vesicles (LUVETS) by known extrusion techniques. The present invention utilizes a micelle surfactant with sufficiently low critical micelle concentration, and includes cholesterol in the bilayer membranes of the liposomes at sufficient concentration that the micelle suspension does not dissolve the lipid bilayers. The system is stabilized by first equilibrating all phases with surfactant and drug, and by using a particular lipid/cholesterol/surfactant composition that optimizes loading of the target drug by the lipid bilayer membranes. An exemplary liposome loaded with TAXOL® is described in detail herein. Amounts of TAXOL® in such liposomes prepared according to the present invention can reach levels of at least about 5 mole %, 6 mol %, 7 mol %, 8 mol %, 9 mol %, 10 mol % or more, relative to SOPC in the liposome.

The present invention further provides a method for delivering therapeutic compounds of low aqueous solubility to cells in vivo. The method comprises administering to the patient the drug-carrying liposome, or micelle-liposome comprising a mixture of micellized drug encapsulated in a liposome.

The present invention is related to formulations and compositions containing therapeutic agents with poor water-solubility. The concentration of such therapeutic agents in aqueous media can only be increased if solubilized with a co-solvent. The present invention utilizes a vesicle-forming lipid modified by a surfactant lipid, or a combination of both lipid and surfactant, to produce a liposome-encapsulated micellized suspension of a therapeutic agent. The present invention provides a lipid capsule with increased solubilizing characteristics for poorly water soluble agents; the solubilizing characteristics for the agent are increased by creating a lipid membrane composed of phospholipids and other lipid surfactants. The present invention further provides a lipid membrane capsule encapsulating a micellar rug suspension, where the lipid membrane is composed of phospholipids, surfactant lipids, cholesterol, and the drug, in such composition that the micellar suspension does not dissolve the membrane.

Liposomes Containing Micelles

Figure 20:
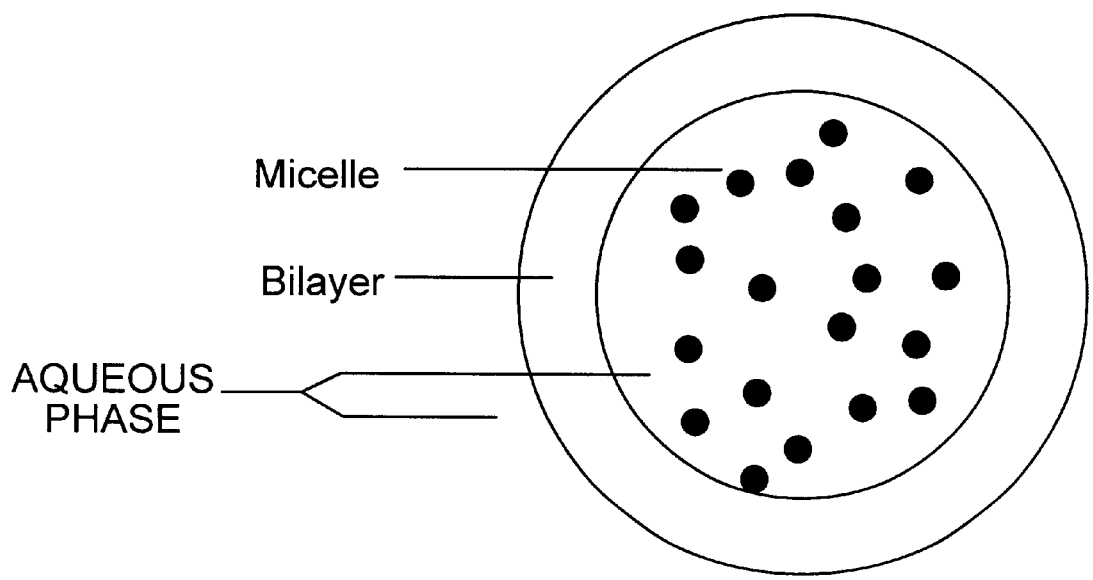
FIG. 20 illustrates the three compartments of a liposome according to the present invention: i.e., the lipid bilayer, the micelle suspension and the solvent aqueous phase.

Liposomes containing micelles essentially consist of 4 components and three compartments into which each component can segregate (FIG. 20). The ability of a component to segregate into a compartment varies, depending on the component's maximum solubility in the compartment and whether equilibrium is or can be established.

The components of liposomes that contain micelles are: (i) membrane bilayer-forming material, usually, but not exclusively, from the class of common membrane phospholipids and cholesterol; (ii) low CMC surfactant, usually but not exclusively a lysolipid, such as monooleoylphosphatidylcholine; (iii) the active agent or drug (an exemplary drug discussed herein is TAXOL®) and (iv) aqueous buffer.

The components are combined to form a liposome having three compartments: (a) a bilayer forming an encapsulating membrane, which can be composed of phospholipid, cholesterol, lysolipid and/or the drug; (b) a micelle dispersion, principally composed of lysolipid and drug, optionally containing some phospholipid and/or cholesterol; (c) aqueous buffer in which liposomes, dissolved components (e.g., free monomer of lysolipid, free drug, and a small amount of phospholipid) and the micelle suspension are contained.

The active agent may be carried by the membrane bilayer in any of several ways: partitioned into or within the membrane bilayer, or adsorbed on the external surface of the bilayer (i.e., attached to the surface of the bilayer that is exposed to the external aqueous environment); or adsorbed on the internal surface of the bilayer (i.e., attached to the surface of the bilayer that is exposed to the internal aqueous content of the liposome).

As used herein, "micellized active agent preparations" refers to a preparation of an active agent associated with micelles. The active agent or drug may be carried within the micelle interior, or associated with the surface of the micelle (see FIG. 23).

Mutual solubilities exist between the various components of the present drug delivery system. The amount to which one component can partition into the phase formed by another component determines the capacity of the micelle-liposome system to carry drug, and determines the stability of the encapsulated micelle system. This amount depends on the solubility limit that a particular component has in the particular phase in question. The solubility limit is commonly known to those skilled in the art as the maximum solute addition into a solvent phase without super saturation. For example, cholesterol will dissolve into a bilayer phase composed of phospholipid up to a solubility limit of about 60 mol % (Needham and Nunn, *Biophys. J.* 58:997 (1990)). Thus the bilayer phase is the solvent for the cholesterol solute, up to the point at which cholesterol precipitates in the aqueous phase as a cholesterol rich crystallite. Similarly, lysolipid can dissolve into phospholipid bilayers up to the point at which the phase change from bilayer to micelle occurs. With regard to drug, a given drug might have limited solubility in the aqueous phase, but when associated with lysolipid micelles or phospholipid bilayers, can be co-dissolved into an aqueous phase to much higher concentration, increasing the solubility limit of the drug in aqueous media by orders of magnitude. This is the case for TAXOL®, where its solubility limit in aqueous media is in the micromolar range but, as demonstrated in the following examples, in the presence of 20 mM LPC the solubility limit can be increased to 4mM (an increase of about 4000 times).

The following examples are provided to illustrate the present invention, and should not be construed as limiting thereof. In these examples, CMC means Critical Micelle Concentration, MOPC means mono-oleoyl-phosphatidylcholine; SOPC means 1-stearoyl-2-oleoyl-sn-gycero-3-phosphocholine; DMPE means dimyristoyl phosphatidylethanolamine; DMPC means dimyristoyl phosphatidylcholine); and $L_p$ means the projection length of a test vesicle into a holding pipet.

EXAMPLE 1

Materials and Methods

Vesicle and Lysolipid Solution Preparation

Lipid vesicles were made from 1-Stearoyl-2-Oleoyl-sn-Glycero-3-Phosphocholine (SOPC) and 1,2-Dimyristoyl-sn-Glycero-3-Phosphoethanolamine -N-PEG-750 (DMPE-PEG(750)-lipid) (Avanti Polar Lipids Inc., Alabaster, Ala., USA) using the procedure described by Needham and Zhelev In *Vesicles* Rosoff (Ed.), Marcel Dekker, New York and Basel (1996). Briefly, chloroform solutions of the particular lipids were mixed to obtain the desired molar ratios. Thirty (30) microliters of a lipid solution were spread onto a roughened TEFLON® (E. I. du Pont de Nemours and Co.) disc and the chloroform evaporated under nitrogen. Final traces of solvent were removed by placing the disc in an evacuated desiccator for 2 hours (Needham and Nunn, *Biophys. J.* 58:997 (1990)). The so-formed dried lipid layers were prehydrated with water vapor in a nitrogen carrier gas and then fully hydrated overnight in a sucrose solution at 40° C. The osmolarity of the solution was 200 mOsm. Both the pure SOPC and SOPC/PEG(750)-lipid vesicles were re-suspended in a glucose solution of 205 mOsm for use in micromanipulation experiments as described below.

The exchanged molecule utilized in the lysolipid exchange experiments as described below was monooleoylphosphatidylcholine (MOPC) (Avanti Polar Lipids, Alabaster, Ala., USA). To prepare the lysolipid exchange solution, a chloroform solution of the lysolipid (0.05 mg/ml) was dried under nitrogen from a roughened TEFLON® disc. Then, the dried lysolipid was hydrated overnight in a glucose solution to give the final desired concentration of MOPC. The osmolarity of the hydrating solution was 205 mOsm, the same as the glucose solution used for resuspending the vesicles as described above.

Micromaninulation: An experimental chamber 3 mm thick and open at both sides was utilized for micromanipulation of vesicles. Experiments were performed at room temperature (23° C.) using an inverted NIKON® microscope with 60× oil immersion objective. The microscope images were recorded using a COHU CCD camera. The micropipets were made of 0.75 capillary glass tubing pulled to a fine point with a vertical pipette puller and cut to the desired diameter with a microforge. The pipettes were connected to a manometer system that allowed the applied pressures to be changed and measured to an accuracy of 2 microatmospheres. The micropipet suction pressures were measured by differential transducer (Validyne DP15-24). The measured pressures together with real time were multiplexed on the recorded images with a multiplexer (Model 401, Vista Electronics, La Mesa, Calif., USA). The recorded images were used to measure the change of the vesicle projection length inside the holding pipet during uptake and desorption of lysolecithin, and to calculate the membrane tension. This was done using calibrated video calipers (Model 305, Vista Electronics).

Figure 1B:
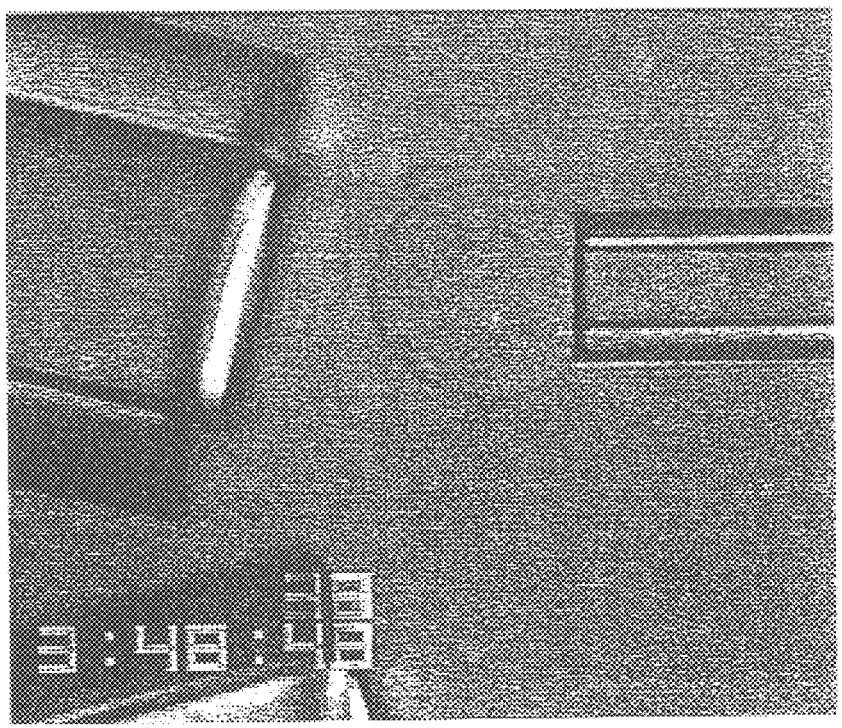
FIG. 1B is a videomicrograph of a holding pipet and test vesicle as shown in FIG. 1A, after the flow pipet delivering MOPC-free solution has been exchanged for a flow pipet delivering MOPC-containing solution to the exterior of the test vesicle. The vesicle projection length ($L_p$) inside the holding pipet is increased compared to the initial $L_p$ obtained in the MOPC-free environment.

Lysolipid Exchange Experimental Set-up: The experimental set-up for lysolipid exchange was similar to that used by Needham and Zhelev, *Ann. Biomed. Egr.* 23:287 (1995); see also Needham and Zhelev, IN: *Vesicles,* Rosoff M (Ed.), Marcel Dekker Inc., New York (1996). The micropipet assay for studying the exchange of MOPC with SOPC vesicles with and without grafted PEG(750) is illustrated in FIGS. 1A and 1B. A holding micropipet is used to hold a test vesicle; flow pipets are used to direct solutions over the exterior of the test vesicle. The vesicle projection length ($L_p$) inside the holding pipet is measured and the effects of various solutions on the $L_p$ of the test vesicle are compared.

The microchamber and holding pipet were preincubated, in a solution of 1 wt %; bovine serum albumin (Sigma Chemical Co., Mo., USA) prior to each experiment. This treatment minimized vesicle adhesion to the pipet wall and glass microchamber; after 10 minutes preincubation, the albumin solution was removed and replaced by a glucose (MOPC-free) bathing solution. A single vesicle was held by the holding pipet with a suction pressure of 200 N/m2 (2,000 dyn/cm2) in a bathing, MOPC-free glucose solution (FIG. 1A). This suction pressure was sufficient to hold a test vesicle by the pipet, and induced only low levels of tension (about 0.2 mN/m) in the vesicle membrane compared to the tensile strength of the membrane (about 6 mN/m) (Needham and Nunn, *Biophys. J.* 58:997 (1990)).

(In these exchange experiments where the molecular composition of the membrane is changed by the incorporation of lytic surfactants, the tensile strength of the membrane is dramatically reduced by MOPC (see McIntosh et al., *Biochemistry* 34:8520 (1995)) and, for high CMC surfactants, can eventually go to zero at the CMC of the surfactant (Evans et al., In Bile Acids in Gasteroenterology Basic and Clinical Advances, Hoffman et al. (Eds.) Kluwer Academic Publishers, Doderecht, Boston and London, pp. 59–68 (1994)); it is therefore important to keep as low a tension on the vesicle as possible to achieve equilibrium uptake without premature failure of the vesicle.)

Glucose bathing solution (MOPC-free) was then delivered to the exterior of the test vesicle (in FIG. 1A, from the lower flow pipet) to establish initial starting conditions. A MOPC solution was then delivered over the exterior of the test vesicle (in FIG. 1B, from the upper pipet) using an osmotically matched test solution of the desired concentration of MOPC. After exposure to MOPC-containing solution, any uptake of MOPC by the lipid vesicle can be detected by measuring the projection length (Lp) of the vesicle in the micropipet, as compared to the $L_p$ under MOPC-free conditions; uptake of MOPC into the test vesicle membrane is shown by an increase in the $L_p$ (compare FIG. 1A and FIG. 1B). For a constant volume of the vesicle, an increase in projection length represents an increase in vesicle membrane area. As discussed below (Equation 1), this area change can then be used to determine the mol % of MOPC in the membrane (Needham and Zhelev, *Ann. Biomed. Egr.* 23:287 (1995)).

In the above-described experimental set-up, over time the test vesicle area either reached a maximum or the vesicle broke down. To desorb MOPC from an intact test vesicle, the vesicle was once more exposed to a MOPC-free bathing solution (not shown). Exposure of a MOPC-containing vesicle to lysolipid-free solution resulted in a rapid decrease of membrane area until a minimum area is attained. This minimum final area is similar to, if not the same as, the vesicle area before MOPC uptake, demonstrating (a) essentially complete desorption of lysolipid and (b) reversible lysolipid exchange. The measured projection lengths ($L_p$), together with the measured pipet radius and the outside vesicle radius, can be used to calculate the original vesicle area (Ao) and the area change due to MOPC uptake ($\Delta A$). As initially the MOPC would only be expected to enter the outer monolayer, the relative fractional area change $\Delta A/Ao$ was converted to a mol % for exchanged MOPC molecules relative to the total number of lipids in the outer monolayer of the bilayer by using the approximation developed by Zhelev:

$$\Delta A \frac{A_{SOPC}}{A_{MOPC}} \quad \text{(Equation 1)}$$

where $\Delta A$ is the change in vesicle area due to MOPC uptake relative to the starting area, $A_{SOPC}$ is the area per lipid molecule of 67Å$^2$, $A_{MOPC}$ is the area per MOPC molecule of 35Å$^2$ (Zhelev, *Biophys J.* 71:257 (1996)).

Three basic experimental tests were performed using the above-described technique (Example 4):

(1) Upon exposure to 100 $\mu$M MOPC, bilayer uptake and desorption of MOPC were measured as a function of PEG(750)-lipid concentration in the membrane, from 0 to 20 mol % PEG(750)-lipid.

(2) MOPC uptake was measured for 4 mol % PEG(750)-lipid bilayers as a function of MOPC concentration in the bathing solution from 0.025 $\mu$M to 500 $\mu$M; checks for uptake by unmodified bilayers and bilayers containing 20 mol % PEG-lipid were also made at the CMC of 3 $\mu$M.

(3) Mechanical tests of bilayer tensile strength were carried out on vesicles that contained 0–20 mol % PEG(750)-lipid as a function of MOPC uptake.

The critical micelle concentration (CMC) of the lysolipid was measured independently by DPH fluorescence following the method in Chattopadhyay and London, *Analytical Biochem.* 139:408 (1984). Briefly, a series of solutions containing increasing concentrations of MOPC in the range $10^{-7}$M to $10^{-4}$ M were prepared. Diphenyl hexatriene (DPH), a lipid soluble fluorescent dye, was added to these samples and the intensity of fluorescence was measured by spectrofluorimeter at absorption and emission wavelengths of 358 nm and 430 nm, respectively. The CMC was determined by plotting the fluorescence intensity (in arbitrary units) verses concentration of MOPC solutions, made up by diluting a 100 mM stock solution of MOPC (solubilized initially by Tetrahydrofuran) in water (Chattopadhyay and London, *Analytical Biochem.* 139:408 (1984)).

EXAMPLE 2

Geometric Characteristics of Grafted PEG Polymer

PEG has been shown to be a "non-adsorbing" polymer, i.e., when lipid vesicles are placed in a bulk polymer solution there is a depletion zone extending from the surface of the lipid vesicles in which the polymer concentration is less than in the bulk solution. Arnold et al., In Molecular Mechanisms of Membrane Fusion (Ohki et al., Eds.) Plennum Press, New York and London, pp. 255–272 (1987); Evans and Needham, *Macromolecules* 21:1822 (1988). When PEG(750) is covalently attached to a lipid molecule in the vesicle membrane the attached polymer remains in the region next to the membrane surface, and, because of its non-adsorbing property, the polymer chain extends away from the vesicle surface in either a "mushroom" or "brush" conformation, depending on the surface density of polymer. For low polymer densities the conformation of an individual PEG(750) chain is essentially unaffected by the presence of the other PEG(750) chains, and the polymer conformation is similar to that of a single chain in solution (deGennes, *Macromolecules* 13:1069 (1980)). In this case the polymer occupies a region next to the membrane surface which has an apparent size given by the Flory radius, RF (deGennes, 1980):

$$R_F = aN^{3/5}$$

where a is the apparent monomer size and N is the number of monomers in the chain.

The apparent size of the PEG(750) monomer is on the order of 3.5 Å (Kenworthy et al., *Biophys. J.* 68:1921 (1995)) and the number of monomers for PEG(750) is 17, giving a value of approximately 19Å for the Flory radius. The projected area of the region corresponding to this Flory radius is 288 Å$^2$, and gives the area of membrane surface covered by a single PEG(750) "mushroom". A comparison of the mushroom area to the area of a single lipid molecule (approximately 65 Å$^2$ (McIntosh and Simon, *Biochemistry* 25:4058 (1986)) shows that the grafted PEG(750) is in a mushroom conformation until PEG(750)-lipid concentrations in the membrane reach approximately 22 mol %, at which point the mushrooms begin to overlap and the so called "brush" regime forms (deGennes, *Macromolecules* 13:1069 (1980)). Therefore, in experiments where PEG (750)-lipid concentrations range from 0.5 mole to 20 mol %, PEG(750) grafted to the vesicle surface will be in the mushroom conformation, and will essentially completely cover the lipid bilayer surface at 20 mol % PEG(750).

EXAMPLE 3

Geometric Characteristics of MOPC Micelle

The geometric characteristics of MOPC micelles were calculated using simple molecular shape considerations; these considerations were checked against surfactants for which micelle size and shape have been measured. Israelachvili et al., *Quar. Rev. Biophys.* 13:121 (1980), have shown that the size and shape of lipid aggregates depend on the area of the surfactant headgroup, the length of its hydrocarbon chain, and the chain volume. These molecular characteristics are used to 'construct' an MOPC micelle with minimum exposed hydrophobic area. It is assumed that the micelle hydrophobic region is incompressible, does not have void space at the center, and one of the dimensions of the micelle hydrophobic core does not exceed twice the length of a lysolipid hydrocarbon chain. Because the lysolipid making up MOPC micelles is a single chain molecule, it is expected that its micelle will be axisymmetric (Bendedouch et al., *J. Phys.. Chem.* 87:153–159 (1983)). As the cross-sectional area of a single hydrocarbon chain (approximately 34 Å$^2$; McIntosh et al., *Biochemistry* 34:8520 (1995)) is smaller than the area per headgroup (approximately 44 Å$^2$; Mattai and Shipley, *Biochim. Biophys. Acta* 859:257 (1986)), the relevant molecular area for the packing of single chain phosphatidylcholines in micelles is the headgroup area.

Before using these assumptions to calculate the size of the MOPC micelle, the approach can be tested by predicting the size and shape of dicaproylphosphatidylcholine and diheptanoylphosphatidylcholine micelles that have been measured experimentally (Lin et al., *J. Am. Chem. Soc.* 109:2321 (1987)). Thus, the micelle hydrophobic core is expected to have a spheroidal shape with minor axes equal to the maximum length $l_{max}$ of the lipid hydrocarbon chain. The lipid hydrocarbon length is calculated from the number of hydrocarbons $N_h$ in the chain, by using Tanford's formula (Tanford, *The hydrophobic effect: Formation of micelles and biological membranes,* Wiley & Sons, New York (1980)):

$$l_{max} = (1.5 + 1.265 \, (N_n - 1)) \text{ Å}$$

Similarly, the volume of the hydrocarbon region $V_h$, is calculated by (Tanford, 1980):

$$V_h = (27.4 + 26.9 \, (N_h - 1)) \text{ Å}^3$$

Using the above characteristics for dicaproylphosphatidylcholine and diheptanoylphosphatidylcholine, the minimum exposed hydrophobic area for their micelles is found when the micelles are made of 19 monomers and 26 monomers, respectively. The number of monomers per micelle (or the micelle aggregation number) for these two short chain lipids, determined from small angle neutron scattering experiments, is 19 and 27, respectively (Lin et al., *J. Am. Chem. Soc.* 109:2321 (1987)). Thus, the aggregation numbers calculated from the geometric approach correspond to the ones measured experimentally, and validate the present approach to calculating geometric characteristics of MOPC micelles.

The aggregation number of MOPC micelles determined by the above geometric approach is 161, giving a micelle weight of 84,000 g/mol which is similar to the micelle weight for egg lysophosphatidylcholine (95,000 g/mol, determined from diffusion and viscosity measurements; Perrin and Saunders, *Biochim. Biophys. Acta* 84:216 (1963)). The shape of the hydrophobic core of the MOPC micelle, calculated from the model, is that of a spheroid with a minor axis equal to 23 Å and a major axis equal to 33 Å. The hydrophobic core is covered with lipid headgroups that extend about 10 Å from the core (McIntosh and Simon, *Biochemistry* 25:4058 (1986)), giving final micelle dimensions of 66Å×86Å, as shown in FIG. 10.

EXAMPLE 4

Experimental Results

1. Critical Micelle Concentration

Measurement of the CMC for MOPC was made using the DPH fluorescence technique of Chattopadhyay and London, *Analytical Biochem.* 139:408 (1984), as described in Example 1. The cross-over in fluorescence intensity between two distinct regions of the DPH Fluorescence intensity versus MOPC concentration gave an estimated CMC of about 3 μM.

2. MOPC Uptake

Figure 2:
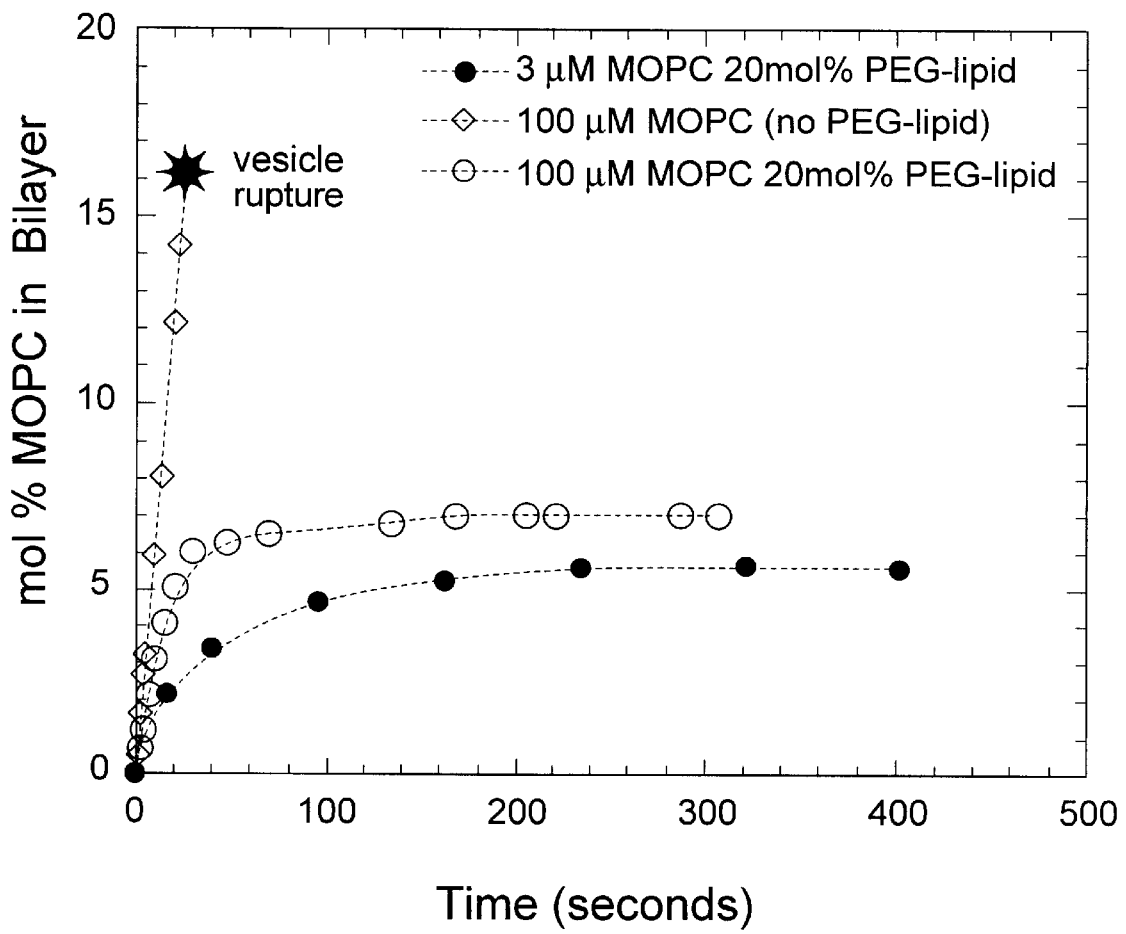
FIG. 2 graphs the exposure of single SOPC vesicles to a flow of MOPC solution. Filled circles=vesicles with 20 mol % PEG-lipid exposed to 3 $\mu$M MOPC; open circles=vesicles with 20 mol % PEG-lipid exposed to 100 $\mu$M MOPC; open diamonds=SOPC (vesicles without any PEG-lipid) exposed to 100 $\mu$M MOPC; and a filled asterisk indicates vesicle rupture. Without PEG-lipid in the bilayer, as shown by the open diamonds, 100 $\mu$M MOPC causes rapid expansion and rupture of the vesicle. With 20 mol % PEG-lipid in the vesicle bilayer, uptake in 100 $\mu$M MOPC (open circles) is essentially the same as that observed at the CMC.

The basic effect of low and high concentrations of MOPC on vesicle uptake and rupture is shown in FIG. 2. Also shown in FIG. 2 is the inhibition of the MOPC-induced rupture when PEG-lipid is included in the bilayer. When an unmodified vesicle was exposed to a solution of 100 μM MOPC, MOPC rapidly partitioned into the bilayer, resulting in rupture at about 15–16 mol %. These results were consistent with previous studies in which MOPC was exchanged with egg PC vesicles (Needham and Zhelev, *Ann. Biomed. Egr.* 23:287 (1995); Zhelev, *Biophys J.* 71:257 (1996)).

In contrast to the unmodified SOPC vesicles, the presence of 20 mol % PEG(750)-lipid completely prevented rupture when the vesicle was exposed to 100 μM MOPC. The amount of MOPC taken up in the membrane increased exponentially and eventually reached a plateau at 5–6 mol % MOPC, representing equilibrium uptake of MOPC into the outer monolayer of the bilayer (Needham and Zhelev, *Ann. Biomed. Egr.* 23:287 (1995); Zhelev, *Biophys J.* 71:257 (1996)). This level of uptake was found to be the same as that for the same PEG-lipid vesicle exposed to the CMC of MOPC, 3 μM.

FIG. 2 graphs the exposure of single SOPC vesicles to a flow of MOPC solution, where filled circles =vesicles with 20 mol % PEG-lipid exposed to 3 μM MOPC; open circles= vesicles with 20 mol % PEG-lipid exposed to 100 μM MOPC; open diamonds=SOPC (vesicles without any PEG-lipid) exposed to 100 μM MOPC; and a filled asterisk indicates vesicle rupture. Without PEG-lipid in the bilayer, as shown by the open diamonds, 100 μM MOPC causes rapid expansion and rupture of the vesicle. With 20 mol % PEG-lipid in the vesicle bilayer, uptake in 100 μM MOPC (open circles) is essentially the same as that observed at the CMC of 3 μM. The data are fitted with an exponential that represents uptake into the outer monolayer of the bilayer (Zhelev, *Biophys J.* 71:257 (1996)).

These results show that the presence of a saturating amount of PEG(750)-lipid eliminates the partitioning of MOPC micelles into the vesicle membrane and inhibits micelle-membrane fusion at elevated concentrations that would otherwise completely dissolve the vesicle. These results further indicate that only monomeric species of MOPC can pass through the thin polymer layer even when there is an excess concentration of micelles in the bathing medium.

3. MOPC Untake as a Function of PEG(750)-Lipid

Figure 3:
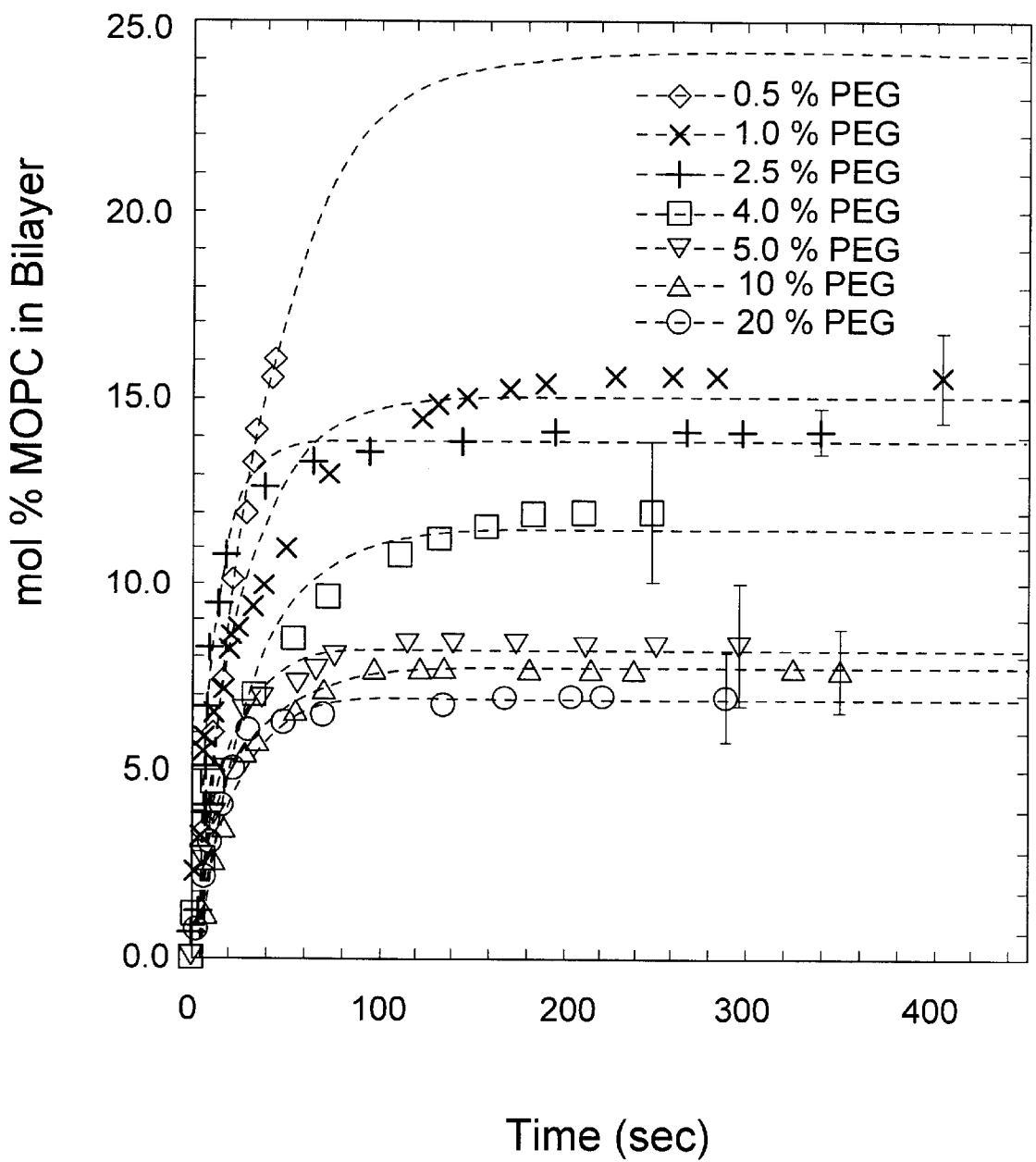
FIG. 3 graphs the exposure of SOPC vesicles containing different concentrations (mole) of PEG(750)-lipid in the vesicle bilayer to a flow of 100 $\mu$M MOPC solution; where open diamonds=0.5% PEG; X=1.0% PEG; crosses=2.5% PEG; open boxes=4.0% PEG; inverted triangles ($\nabla$)=5.0% PEG; triangles ($\Delta$)=10% PEG; and open circles=20% PEG. Standard deviation shown on the last data point for each concentration are averages of 10 test vesicles.

Experiments were then carried out to determine the rate and magnitude of uptake of MOPC from 100 μM solutions as the concentration of PEG(750)-lipid in the membrane was increased from 0.5 mol % to 20 mol %. FIG. 3 plots typical uptake time courses obtained for single vesicles at each PEG-lipid concentration. The uptake experiments were performed several times at each concentration and the standard deviation for these runs is shown on the last time point for each of the uptake experiments. The data are fitted with exponential curves that represent uptake of MOPC into the outer monolayer of the bilayer as described by Zhelev, *Biophys J.* 71:257 (1996).

FIG. 3 graphs the exposure of the SOPC vesicles containing different concentrations (mol %) of PEG(750)-lipid to a flow of 100 μM MOPC solution; open diamonds=0.5% PEG; X=1.0% PEG; crosses=2.5% PEG; open boxes=4.0% PEG; inverted triangles (∇)=5.0% PEG; triangles (Δ)=10% PEG; and open circles=20% PEG. The standard deviation shown on the last data point for each concentration are averages of 10 test vesicles. The data are fitted with an exponential that represents uptake into the outer monolayer of the bilayer Zhelev, *Biophys J.* 71:257 (1996).

For zero (FIG. 2) and 0.5 mol % (FIG. 3) PEG-lipid concentrations, the membranes broke before they could even approach any stationary equilibrium. However, with increasing membrane concentration of PEG-lipid (starting at only 1 mol %), the amount of lysolipid partitioning into the membrane at stationary equilibrium was reduced and bilayers remained stable, while the apparent rate of lysolipid uptake was not significantly affected. Initial slopes of uptake versus time ranged from 0.125 $s^{-1}$ to 0.025 $s^{-1}$. The apparent rate of MOPC uptake was more sensitive to the rate of flow of the bathing solution than to the PEG-lipid concentration in the vesicle membrane (data not shown). (This dependence of the apparent rate of uptake on the hydrodynamic conditions is a result of the significant contribution of the rate of molecular transport across the stagnant layer to the measured rate of uptake. For the flow rates used in these experiments this contribution can be 20% or more (Zhelev, *Biophys J.* 71:257 (1996)).

4. MOPC Desorption from Loaded Bilayers

Figure 4:
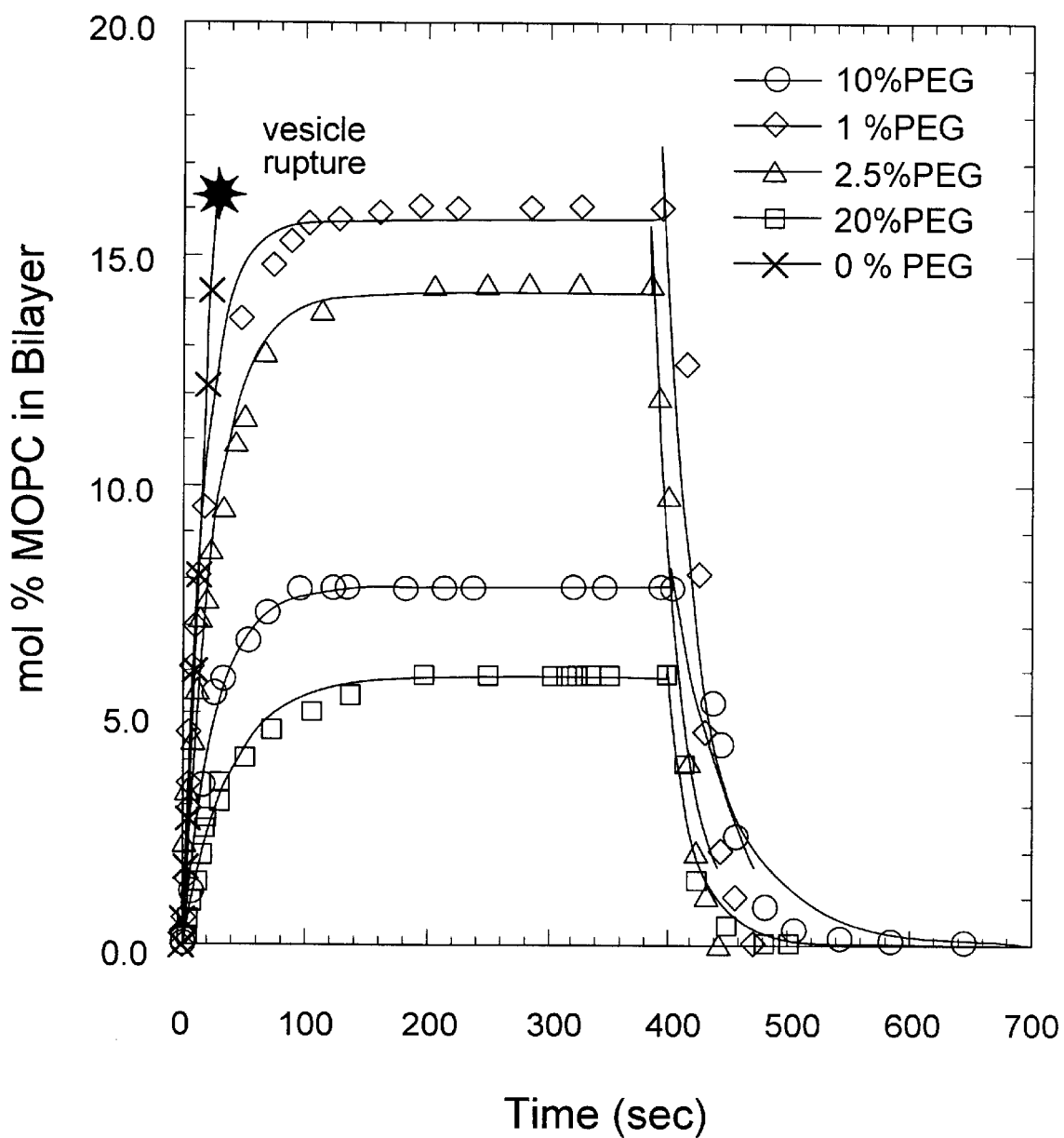
FIG. 4 graphs the uptake and desorption of lysolecithin (100 $\mu$M MOPC) by SOPC vesicles containing varied concentrations (mol %) of PEG(750)-lipid, after more than five minutes' exposure (X=0% PEG; open diamond=1.0% PEG; open triangle=2.5% PEG; open circle=10% PEG; and open square=20% PEG. At 0 mol % PEG(750)-lipid, test vesicles broke after only 50 seconds, and so desorption experiments could not be carried out. Solid lines are theoretical fits to the data.

With regard to the desorption of MOPC from the loaded bilayers, as Needham and Zhelev, *Ann. Biomed. Egr.* 23:287 (1995) and Zhelev, *Biophys J.* 71:257 (1996) have shown, the desorption of the lysolipid from MOPC rich membranes involves only monomers. In this case, because of the small size of the MOPC monomer, it is expected that the kinetics of exchange will not be affected by the presence of PEG (750)-lipid. FIG. 4 shows the time dependence for MOPC uptake followed by its desorption for individual vesicle experiments with different concentration of PEG(750)-lipid.

FIG. 4 graphs the uptake and-desorption of lysolecithin (100 μM MOPC) by SOPC vesicles containing varied concentrations (mol %) of PEG(750)-lipid, after more than five minutes' exposure (X=0% PEG; open diamond=1.0% PEG; open triangle=2.5% PEG; open circle =10% PEG; and open square=20% PEG)). Solid lines are theoretical fits according to the analysis of Zhelev, *Biophys J.* 71:257 (1996). At 0 mol % PEG(750)-lipid, test vesicles broke after only 50 seconds, and so desorption experiments could not be carried out. At other PEG(750) -lipid concentrations, test vesicles remained intact and the uptake of lysolecithin into the bilayer reached a constant value. Desorption of MOPC from the bilayer was measured by bathing the vesicles with a MOPC-free solution and measuring the reduction in the projection length ($L_p$) of the vesicle membrane inside a holding pipet. Solid lines are theoretical fits to the data.

The present data establish that the kinetics of MOPC desorption are not affected by the presence of grafted lipid. For a flow rate of bathing solution of 400 μm/s, the measured overall rates of desorption from these data are similar for all PEG(750)-lipid concentrations and have an average value of 0.4±0.2 $s^{-1}$ (measured from 5 vesicles). This value is similar to the one measured in the experiment of Needham and Zhelev, *Ann. Biomed. Egr.* 23:287 (1995) of 0.2 $s^{-1}$ (at the slightly slower flow rate of 300 μm/s) for desorption of MOPC from unmodified egg PC membranes. Again, desorption rates are very sensitive to flow rates of solutions over the vesicle surface.

Figure 5A:
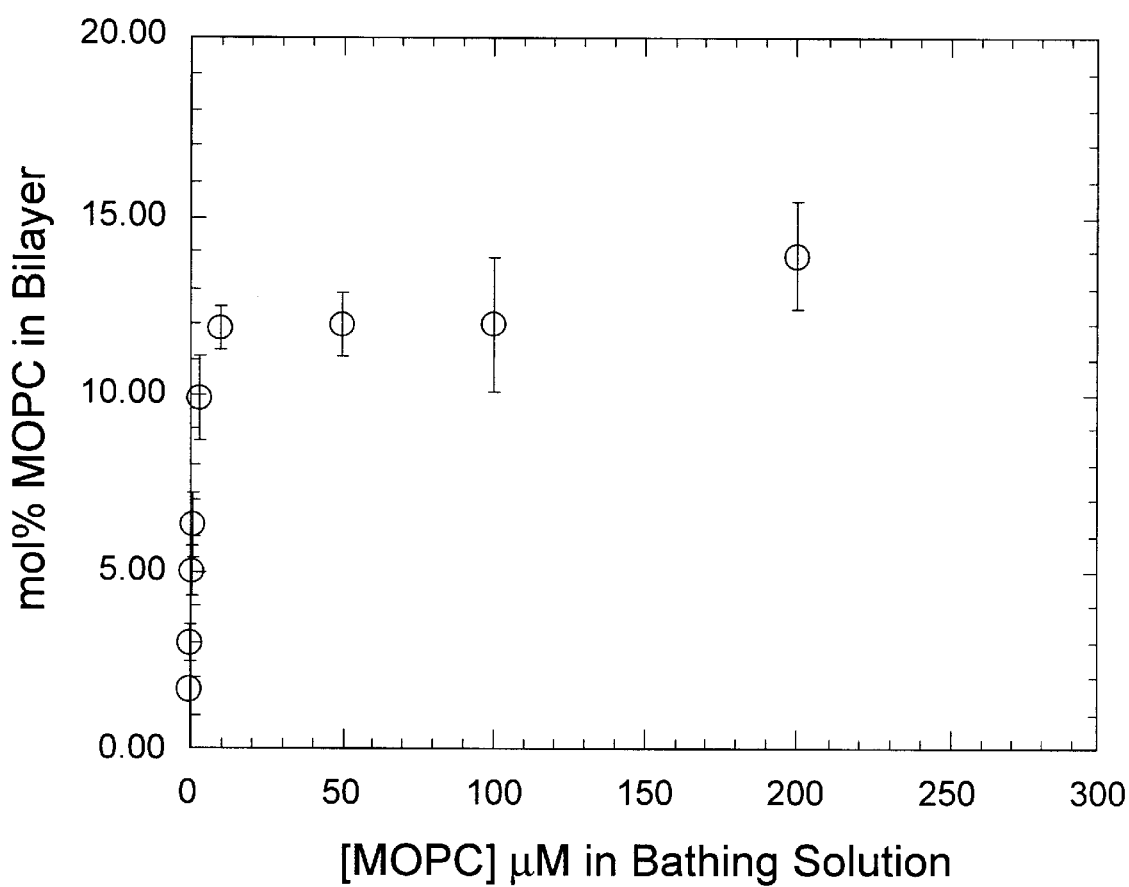
FIG. 5A graphs the dependence of MOPC uptake into 4 mol % PEG-lipid vesicles as a function of the bathing MOPC concentration, for the concentration range of 0 $\mu$M MOPC to 300 $\mu$M MOPC in the bathing solution.
Figure 5B:
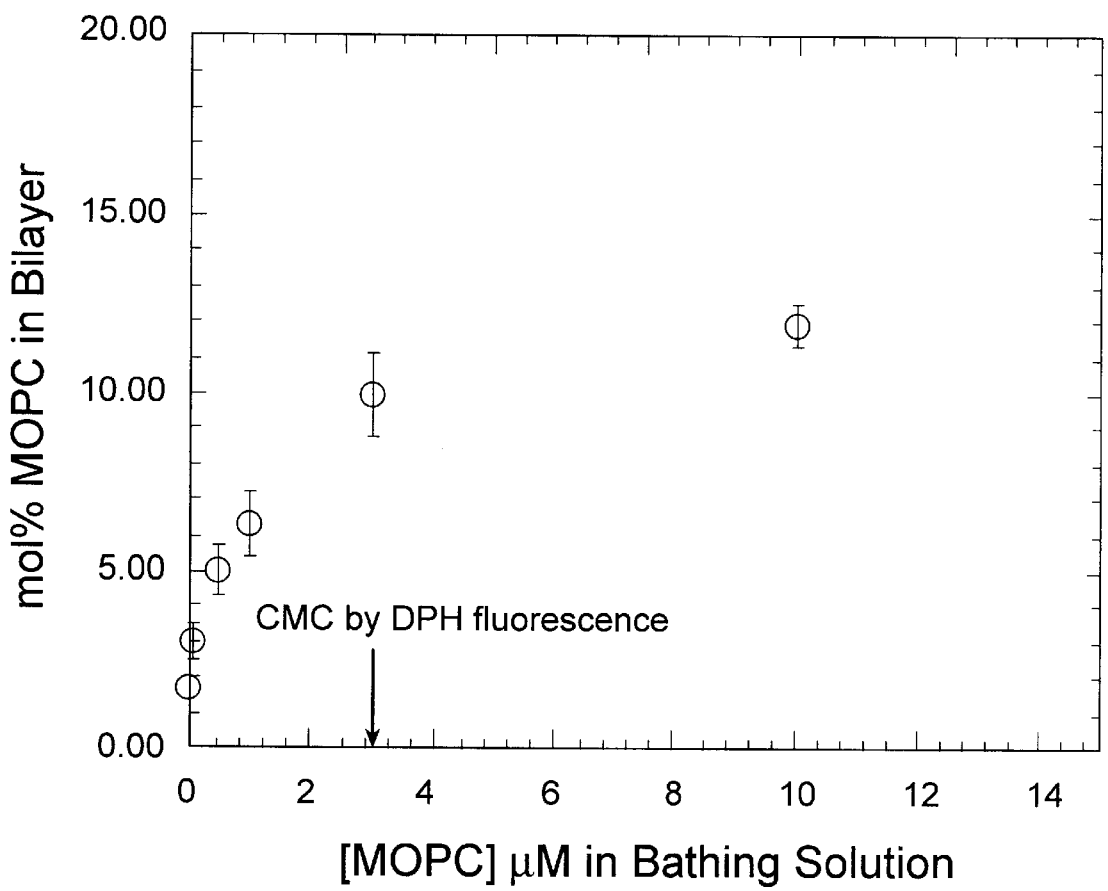
FIG. 5B graphs the dependence of MOPC uptake into 4 mol % PEG-lipid vesicles as a function of the bathing MOPC concentration, for the concentration range of 0 $\mu$M MOPC to 14 $\mu$M MOPC in the bathing solution. As indicated by an arrow, the cross-over of concentration regimes occurs close to 3 $\mu$M (the CMC of MOPC measured by DPH fluorescence).

5. MOPC Uptake by PEG-lipid Vesicles as a Function of Bathing MOPC Concentration In assessing the thermodynamics of the lysolipid exchange process, it is important to measure the stationary uptake of MOPC by the bilayer as a function of bathing MOPC concentration for a fixed PEG-lipid concentration in the bilayer. To do this using 4 mol % PEG-lipid, the amount of MOPC uptake was measured for concentrations below the CMC (0.025, 0.05, 0.1, 0.5, 1 μM), at the CMC (3 μM), and above the CMC (10 μM, 50 μM, 100 μM, 200 μM, 350 μM, and 500 μM). FIG. 5A shows how the amount of MOPC taken up by the 4 mol % PEG-lipid bilayer increases rapidly for MOPC concentrations of 0.025 μM to 3 μM, but then shows a weaker dependence on bathing concentration even up to 500 μM. FIG. 5B shows the lower concentration region of FIG. 5A, where the cross over in slope from monomer to monomer-plus-micelle occurs at approximately the CMC of about 3 μM, measured independently by the DPH fluorescence technique.

Figure 12:
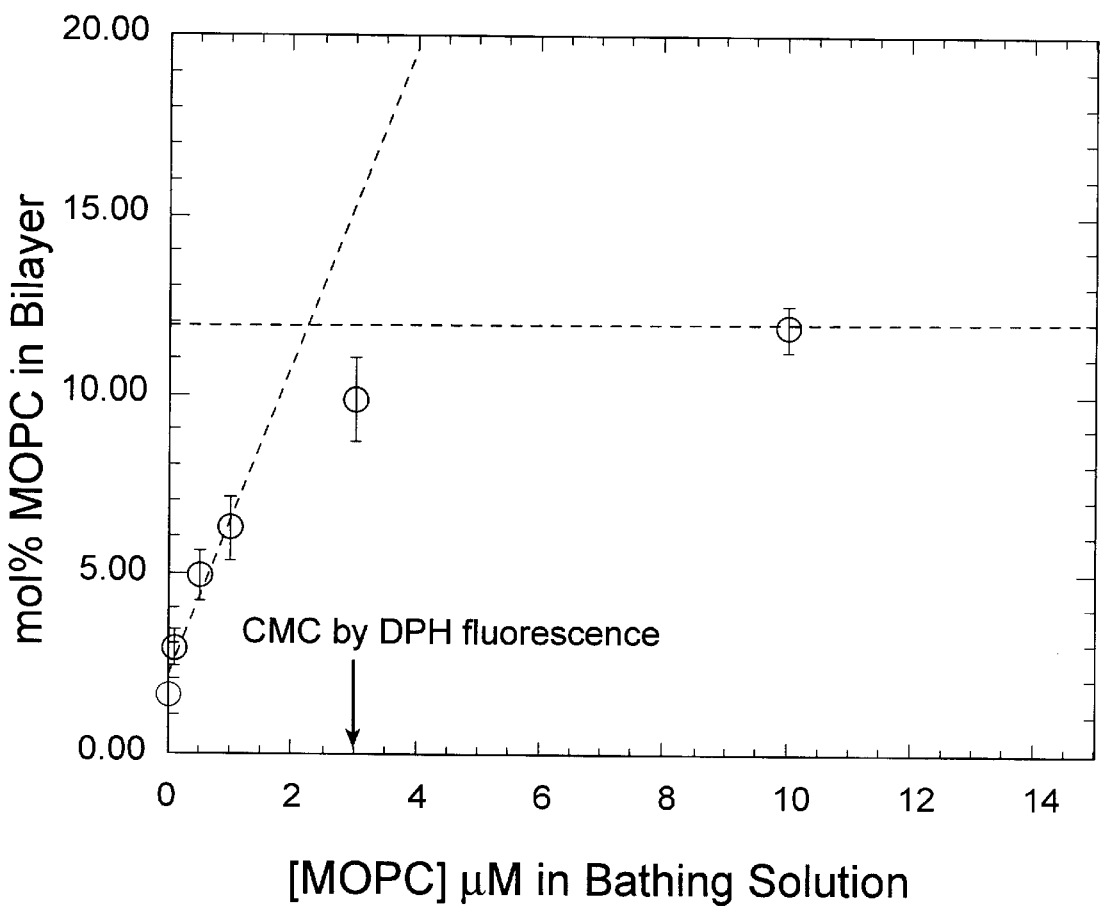
FIG. 12 is the theoretical model for the data provided in FIGS. 5A and 5B.

As discussed further below, the stationary concentrations of MOPC in the membrane are determined by the balance between the rates of uptake and desorption of monomers below the CMC and by uptake of monomers and micelles, and desorption of monomer above the CMC. The prediction, based on this simple two species model, for the membrane concentration of MOPC in the two regions of bathing MOPC concentration is shown in FIG. 12, where the slopes of the lines represent the ratios of the on and off rates for monomer, and for micelle and monomer, respectively.

6. Mechanical Tests of Bilayer Tensile Strength

Figure 6:
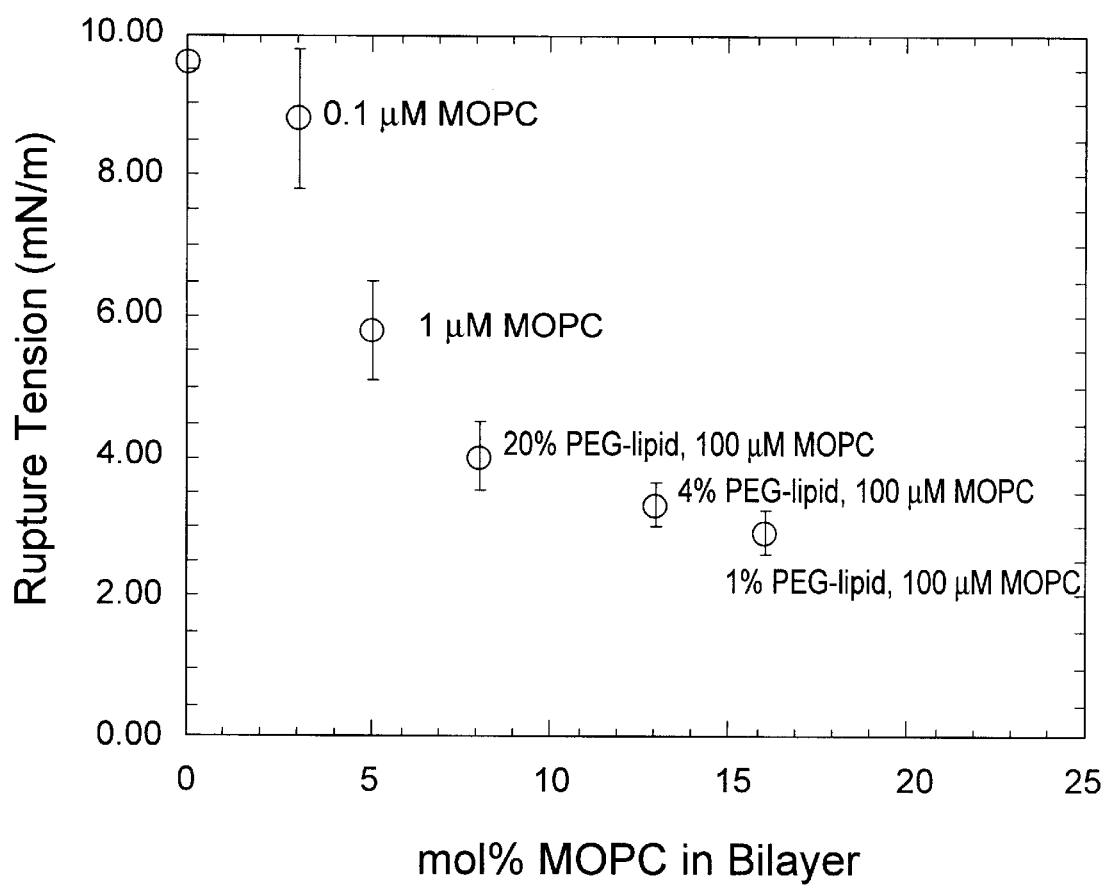
FIG. 6 graphs the rupture tension of vesicle membranes as a function of mol % MOPC in the vesicle bilayer. Different amounts of MOPC in the bilayers were achieved by combinations of bathing solution MOPC concentration and PEG-lipid concentration in the vesicle membranes, as indicated next to each data point on the plot.

As the bilayer takes up more and more of a water-soluble second component (e.g., bile acid or MOPC) it is expected that it will become weaker and softer (Evans et al., In Bile Acids in Gasteroenterology Basic and Clinical Advances, Hoffman et al. (Eds.) Kluwer Academic Publishers, Doderecht, Boston and London, pp. 59–68 (1994); Needham and Zhelev, *Ann. Biomed. Egr.* 23:287 (1995); Zhelev, *Biophys J.* 71:257 (1996)). To test this model, the tensile rupture strength of vesicles containing various amounts of MOPC at stationary equilibrium was measured. FIG. 6 shows how the rupture strength of the vesicle membrane does in fact decrease with increasing MOPC concentration. To obtain the wide range of MOPC bilayer concentrations, several different lipid, PEG-lipid and MOPC solution concentrations were used (0.1 μM MOPC; 1.0 μM MOPC; 20% PEG-lipid and 100 μM MOPC; 4% PEG-lipid and 100 μM MOPC; and 1% PEG-lipid and 100 μM MOPC) as indicated on the plot next to each data point in FIG. 6.

Figure 7:
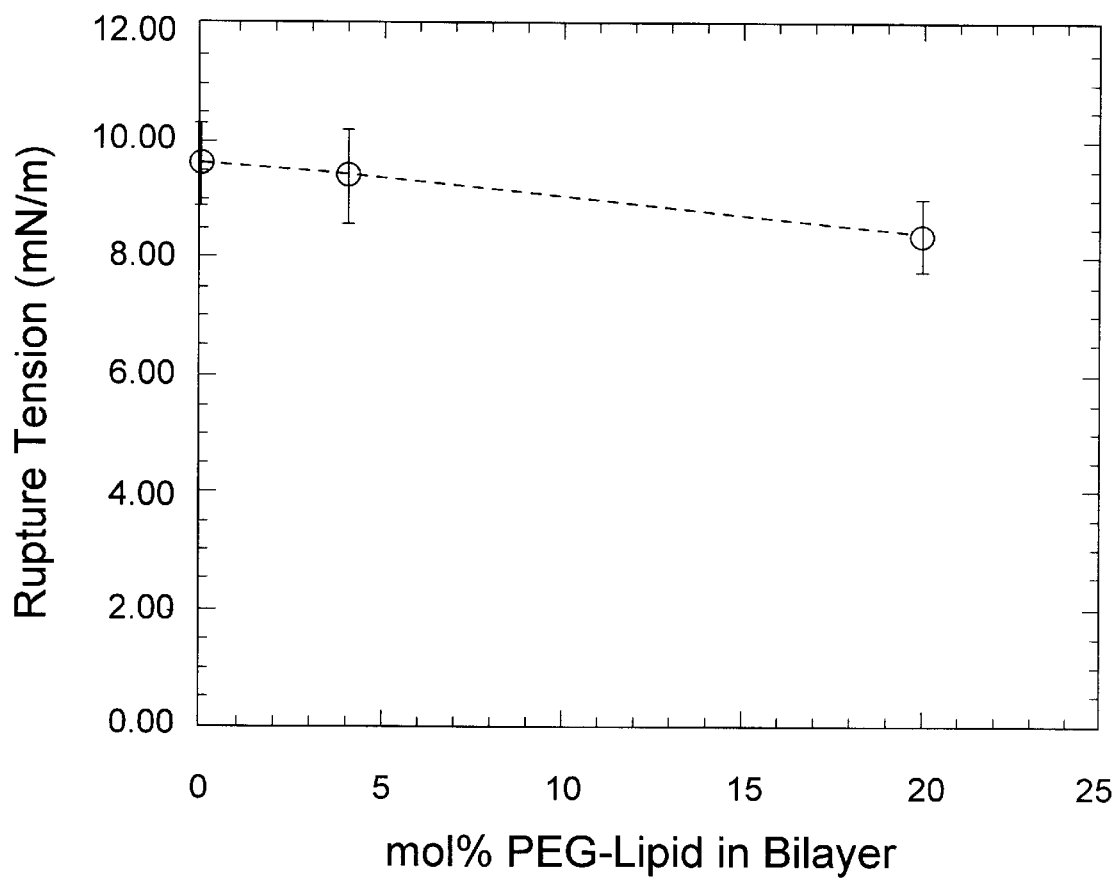
FIG. 7 graphs the rupture tension of vesicle membranes as a function of mol % PEG-lipid in the vesicle bilayer.

PEG-lipids were used in some but not all of these vesicle tests. Whether the incorporation of the PEG-lipids (DMPE-(PEG)750) themselves had any effect on the tensile strength of the bilayer vesicles was also investigated. It might be expected that either the slightly shorter acyl chain of the DMPE-PEG lipid would reduce the tensile strength, since DMPC (dimyristoyl phosphatidylcholine) lipid vesicles have a lower tensile strength than SOPC (Needham and Evans, *Biochemistry* 27:8261 (1988)), and/or that the PEG-lipid chain may exert a lateral expanding pressure that pre-stresses the bilayer, so reducing the amount of applied stress needed to cause failure in tension (Hristova and Needham, *J. Coll. Int. Sci.* 168:302 (1994)). FIG. 7 shows that this particular PEG(750)-lipid did not reduce the tensile strength significantly, up to 20 mol % PEG-lipid.

EXAMPLE 5

Analysis and Description of Model

1. Dependence of MOPC Uptake on Bulk MOPC Concentration

For a given PEG-lipid concentration, the amount of MOPC taken up by a membrane depends on the bulk concentration of MOPC. This allows the determination of the ideality of mixing of MOPC in the bulk solution and in the membrane, i.e., a first approximation would treat the MOPC solution as monomer below the CMC level, and monomer plus micelles above the CMC. Any self association or "micro" aggregation of MOPC in either the bulk solution and/or bilayer phases would produce deviations from this approximation. Below the CMC, bilayers are stable. However, above the CMC, they are extremely unstable, unless protected by PEG-lipid. Thus, the presence of PEG lipid allows one to extend the thermodynamic treatment to MOPC concentrations well in excess of the point at which the membrane should break down.

The simplest thermodynamic approach is to assume that there is only one chemical potential in the system, that of the MOPC monomer, i.e., the phospholipid is virtually insoluble and so is not exchanged, at least not initially, although phospholipid exchange with micelles appears to be involved in the ultimate dissolution of the membrane (Evans et al., In Bile Acids in Gasteroenterology Basic and Clinical Advances, Hoffman et al. (Eds.) Kluwer Academic Publishers, Doderecht, Boston and London, pp. 59–68 (1994)). Evans et al. (1994) found that the uptake of bile salts into lipid bilayers followed an ideal mixing relation at thermodynamic equilibrium. The balance of chemical potentials for the monomer in the bulk solution and the membrane (Evans et al., 1994) can be written in a simplified form:

$$\ln(X_m) = \frac{n_m}{n_s} \cdot \ln[X_s] + \text{constants} \quad \text{(equation 2)}$$

where, $X_m$ is the mole fraction of MOPC in the membrane, $X_s$ is the mole fraction of MOPC in the bulk solution, and the "constants" term contains the reference chemical potentials, and excess energy due to applied membrane tension. The prefactor in this relationship:

$$\frac{n_m}{n_s}$$

is the ratio of monomer aggregate number in the bilayer to the number in aqueous solution so that any value different than 1:1 indicates non-ideality of the system.

As previously discussed, the mole fraction of MOPC in the membrane is found from the relative vesicle area change produced by exposure to MOPC. Since the mole fraction of MOPC in solution is proportional to the solution concentration, a log vs. log plot of mole fraction in the membrane versus MOPC bulk concentration gives the ratio of aggregation states of monomer in the bilayer versus the membrane from the slopes.

Figure 8:
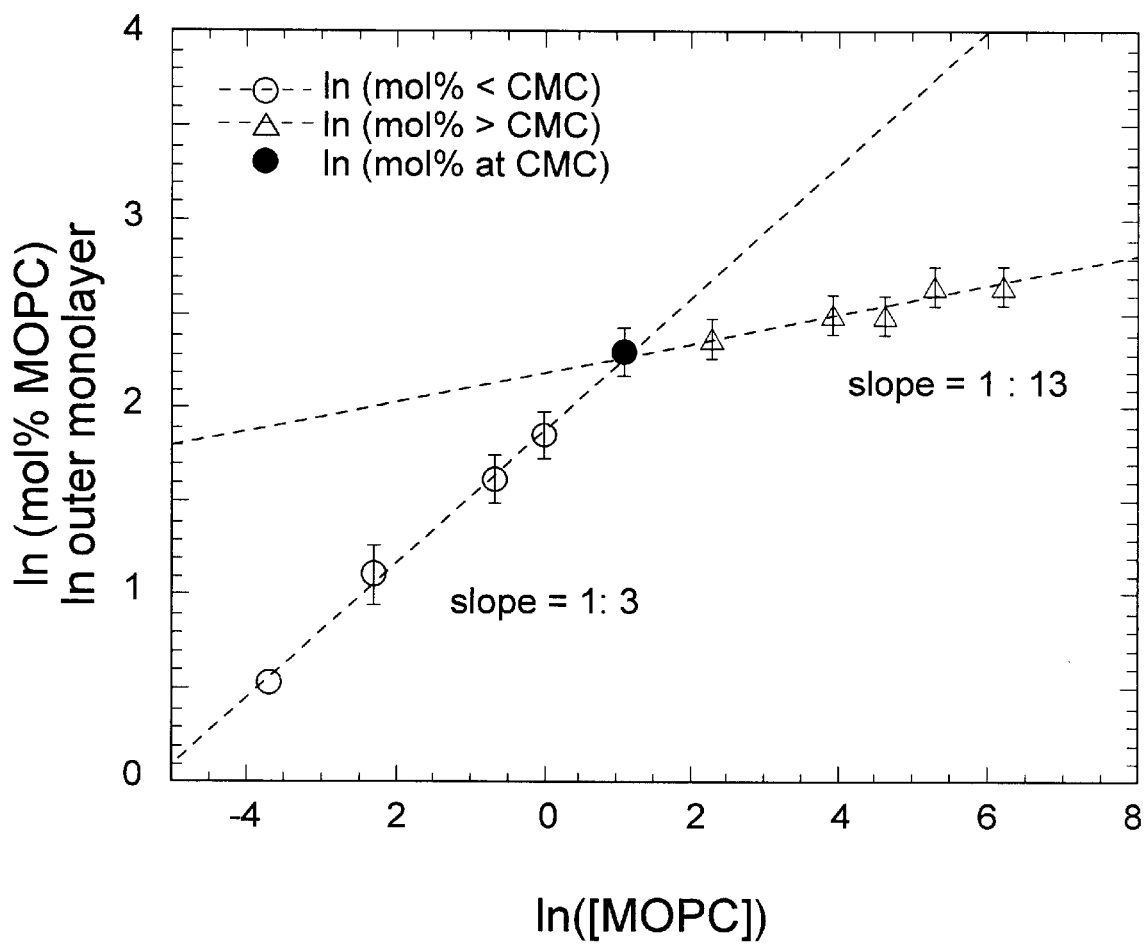
FIG. 8 is a log vs. log plot for mol % MOPC in the outer monolayer of a vesicle bilayer at stationary equilibrium uptake vs. the concentration of MOPC in a bathing medium. Open circles=ln(mol %<CMC); open triangles=ln(mol %>CMC); closed circle=ln(mol % at CMC). Below the CMC, the slope is 1:3 and above the CMC the slope is 1:13; these deviations from 1:1 indicate non-ideality of mixing of MOPC in the bathing solution.

As shown in the log vs log plot in FIG. 8, the $$\frac{n_m}{n_s}$$

ratio below the CMC (from a least squares best fit to the plot) is 1:3, indicating that there is some slight association of monomers in the aqueous solution that is reduced in the bilayer phase. Assuming MOPC in the membrane is monomeric and ideally dissolved in the "lipid solution" of the membrane, then, in aqueous solution, the MOPC monomers are aggregated, on average, as trimers. In corroboration of this result, Evans et al., found previously that, depending on the source of the acid, Bile Acids were also aggregated below the CMC as dimers or tetramers (Evans et al., In Bile Acids in Gasteroenterology Basic and Clinical Advances, Hoffman et al. (Eds.) Kluwer Academic Publishers, Doderecht, Boston and London, pp. 59–68 (1994)).

At MOPC concentrations above the CMC, the ratio is approximately 1:13 which indicates, as expected, that there is a higher level of aggregation in the aqueous phase. Our calculations for aggregate number (see Example 3, above) indicate that there are about 161 monomers per micelle and so the experimentally measured ratio appears smaller than expected. However, some increase in the slope of the plot could arise due to a progressive increase in the concentration of free monomers with increasing bulk concentration. Also, this ratio may reflect monomer aggregation in the membrane, i.e., if the average bulk aggregation number above the CMC is 161, then this ratio of 1:13 would indicate that MOPC has an aggregation number in the membrane of about 12. In total, the present results indicate that MOPC has some tendency to form multimers, even at concentrations below the CMC and the onset of full micellization.

EXAMPLE 6

Stationary Equilibrium Model for MOPC Uptake: Inhibition by PEG-lipid

At stationary (kinetic) equilibrium, the amount of MOPC partitioning into a lipid membrane is determined by the balance between MOPC taken up as both monomer and micelle, and the desorption of MOPC monomers (Needham and Zhelev, Ann. Biomed. Egr. 23:287 (1995); Zhelev, Biophys J. 71:257 (1996)). The data presented herein establish that the presence of only a few mol % of PEG(750)-lipid in the vesicle membrane inhibits the partitioning of MOPC micelles (up to 500 $\mu$M solution concentration) into the membrane while, even up to 20 mol % PEG-lipid does not affect the exchange of MOPC monomers both into and out of the membrane. The PEG-graft acts to selectively sample the aggregate distribution of the surfactant solution itself and thus the data, even below and at the CMC, cannot be fit with a single "on" rate constant as the PEG concentration in the membrane is changed.

Figure 9:
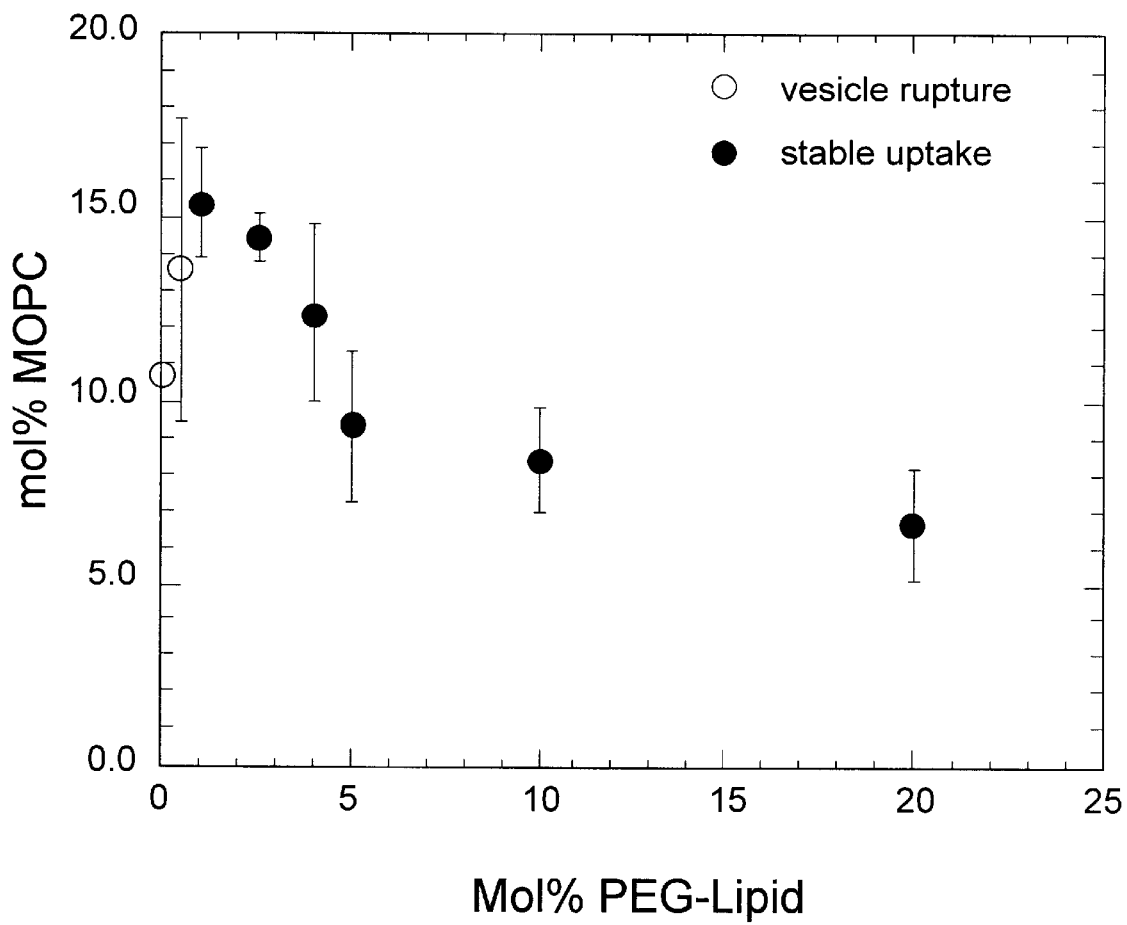
FIG. 9 is a graph indicating stationary equilibrium uptake of MOPC into SOPC vesicles, for different concentrations or PEG-lipid in the vesicle membrane; the concentration of MOPC in the bulk solution is 100 $\mu$M. Standard Deviations are averages of 10 vesicles at each concentration. Open circles=vesicles broke before reaching equilibrium; closed circles=vesicles stable in MOPC solutions and reached equilibrium uptake.

The reduction in the amount of MOPC in the membrane at stationary equilibrium is summarized in FIG. 9, where open circles indicate that the vesicles broke before reaching equilibrium; closed circles indicate that the vesicles were stable in MOPC solutions and reached equilibrium uptake. Standard deviations are averages of ten vesicles at each concentration.

In FIG. 9, the average equilibrium uptake values were collected for MOPC determined from FIG. 3 for each PEG-lipid concentration. It is shown that the amount of MOPC partitioning into the membrane at stationary equilibrium strongly depends on the presence of PEG(750)-lipid. With increasing PEG(750)-lipid concentration in the vesicle membranes, the amount of MOPC that can partition into the Vesicles decreased and was eventually reduced to uptake values that were equivalent to exposing the vesicle to concentrations of MOPC at the CMC (see FIG. 2). Thus, for membranes without PEG and membranes with only 0.5 mol % PEG, membranes broke before attaining equilibrium uptake, (data points in FIG. 9 are distinguished from equilibrium and are shown as open circles). Micelles can readily gain access to the surface and produce rapid uptake of MOPC via micelle fusion, resulting in vesicle breakage. For PEG(750)-lipid concentrations between 1 mol % and 10 mol %, the partitioning decreases rapidly with increasing PEG (750) -lipid concentration. For higher PEG(750)-lipid concentrations (10 mol % to 20 mol %), the partitioning has a weaker dependence on the PEG(750)-lipid concentration, and at 20 mol %; PEG(750)-lipid, MOPC uptake is similar to that measured for MOPC exchange at the CMC, i.e., uptake has been reduced to just monomer exchange (see FIG. 2).

These results demonstrate that at surface concentrations of grafted PEG(750) above 1 mol %, micelle-membrane fusion begins to be reduced and at 20 mol % PEG(750)-lipid this process is completely inhibited. However, the dense 20 mol % PEG layer does not retard the "on rate" of monomer from solution to the membrane, as shown in FIG. 2, or the desorption of monomer from the membrane into solution, as shown in FIG. 4. This demonstrates that there is a molecular size cut-off somewhere between the dimensions of the monomer and the 6.6 nm×8.6 nm micelle.

While not wishing to be held to a single theory, the present inventors note that the simplest interpretation of this reduced uptake as a function of PEG-lipid density is to treat the uptake as an activation step, i.e., the polymer layer presents an activation energy barrier to close approach of the micelle to the bilayer surface. The presence of grafted PEG(750) creates an apparent "surface pressure" in the region next to the membrane surface. This apparent "surface pressure" restricts the access of MOPC micelles to the membrane surface. As mentioned herein, for MOPC exchange, micelle-membrane fusion is coupled with monomer uptake and desorption. This coupling results in a stationary MOPC concentration in the membrane which is set by the magnitude of the rates of the transport processes. Therefore, for MOPC concentrations below the CMC, or above the CMC, the equilibrium amount of MOPC in the membrane is calculated from the adsorption and desorption rates and appropriate bulk concentrations of the monomer and micelle species (Zhelev, *Biophys J.* 71:257 (1996)):

$$C_m = \frac{k'_{bm}}{k_{mb}} C'_{b\infty} + \frac{k''_{bm}}{k_{mb}} C''_{b\infty} \qquad \text{(Equation 3)}$$

where $C_m$ is the membrane concentration of MOPC (calculated as a number of molecules per unit membrane area); $C'_{b\infty}$ is the bulk concentration of MOPC for concentrations up to the CMC, i.e., the concentration of monomer; $C''_{b\infty}$ is the bulk MOPC concentration above the CMC, i.e., corresponding to the amount of MOPC in micelles; $k'_{bm}$ is the rate of MOPC monomer uptake; $k''_{bm}$ is the rate MOPC micelle-membrane fusion; and $k_{mb}$ is the rate of MOPC monomer desorption from the bilayer.

The first term in Equation 3 gives the amount of MOPC taken up as monomer, and the second term gives the amount of MOPC taken up through micelle-membrane fusion. This equation shows that when the product of the rate of micelle-membrane fusion and the micelle concentration is small compared to the product of the rate of monomer uptake and the CMC, the amount of MOPC transported through micelle-membrane fusion is negligible. Thus, by changing the micelle concentration in the bathing solution, or, as in the case of the PEG-"protected" bilayers, the rate of micelle-membrane fusion itself, the total amount of MOPC in the membrane can be manipulated.

To predict the dependence of the rate of micelle-membrane fusion and therefore the MOPC uptake due to micelle fusion on the surface density of grafted PEG(750), the geometric characteristics (size and shape) of both the grafted PEG(750) and MOPC micelle are determined (see Examples 2 and 3).

The geometric characteristics for the micelle and the size of the region occupied by the grafted PEG(750) polymer allow both the MOPC micelle and the region occupied by PEG(750) at the lipid bilayer surface to be drawn to scale (FIG. 10). FIG. 10 shows the relative sizes of the MOPC micelle (spheroid, 66Å×86Å) and the PEG-lipids as "mushrooms" ($R_F$=19Å) at the vesicle surface for a surface density equivalent to about 5 mol % PEG-lipid. Knowing these dimensions allows a discussion of how the position of the MOPC micelle at the polymer-grafted interface varies as a function of PEG-lipid concentration, and how this determines the extent to which micelle-membrane fusion can occur, i.e., these geometric features determine the contribution of the excluded area of PEG(750) "mushrooms" to the process of micelle-membrane fusion through an activation energy for fusion.

The process of micelle-membrane fusion is not well understood, even for unmodified bilayers. In the model used herein, micelle-membrane fusion is considered to be a first order reaction (Glasstone et al., *The Theory of Rate Processes* McGraw-Hill Co., New York (1941)). It is assumed that MOPC molecules have two quasistationary states: micelle state and bilayer state. The transition from the micelle state into the bilayer state occurs through an apparent "activation state", which is characterized by an apparent barrier energy. When there is grafted PEG(750) on the membrane surface, the barrier energy increases because MOPC micelles must cross the region occupied by the PEG(750) mushrooms. The increase of the barrier energy due to the presence of PEG therefore represents the additional work required to transport the micelles through the mushroom region. This work is calculated by multiplying the area in the mushroom region occupied by the micelles, and the apparent "surface pressure" of the mushrooms for a given surface density. The increase of the barrier energy, due to the work required for micelle transport through the mushroom region gives the correction factor for the apparent decrease of the rate of micelle membrane fusion as compared to membranes without PEG(750). In this case, the rate of micelle-membrane fusion in the presence of PEG(750) $k''_{bm(PEG)}$ is equal to the product of the same rate for membranes without PEG(750) $k''_{bm0}$ and the exponential correction factor:

$$k''_{bm(PEG)} = k''_{bm0} \exp\left(-n_{PEG}\left(\frac{a_m}{a_1}\right)\right) \qquad \text{(Eq. 4)}$$

where $n_{PEG}$ is the PEG(750) molar concentration in the membrane; $a_1$ is the area per molecule of the bilayer lipid; and $a_m$ is the cross sectional area of the micelle projected at the surface that corresponds to the point of micelle-membrane fusion (see FIG. 11A).

FIG. 11A schematically shows a MOPC micelle at a lipid bilayer interface, where the lipid bilayer contains a low surface concentration of grafted PEG which just allows the micelle to come into intimate contact with the bilayer interface (i.e., allows intermixing of lipid headgroups from the micelle and the vesicle. The micelle plane of contact with the PEG "mushrooms" is indicated by an arrow on FIG. 11A; the cross-sectional area of the micelle at the plane of contact is 1400Å$^2$. This is the excess area that gives rise to additional activation energy for passage of the micelle to the lipid surface.

Substitution of Equation 4 into Equation 3 gives the amount of MOPC at equilibrium, for membranes with different concentrations of grafted PEG(750):

$$C_m = \frac{k'_{bm}}{k_{mb}} CMC + \frac{k''_{bmo}}{k_{mb}} C''_{b\infty} \cdot \exp\left(-n_{PEG}\left(\frac{a_m}{a_1}\right)\right) \quad \text{(Equation 5)}$$

This activation energy model predicts both the dependence of MOPC uptake in the membrane as a function of MOPC concentration in the bulk phase for a given PEG-lipid mol % in the membrane, and the dependence of MOPC uptake as a function of PEG-lipid mol % for a fired bulk concentration of MOPC. Equation 5 can be used to approximate the experimental data in FIGS. 5 and 9, and these model fits are presented in FIGS. 12 and 13.

Fixed mol % PEG-Lipid (4 mol %); Variable MOPC Bulk Concentration (0.025 µM–500 µM)

Where only monomer and micelle are the exchanging species, the data should be fit with straight lines both below and above the CMC. FIG. 12 is the theoretical model for the data provided in FIGS. 5A and 5B. The slopes in the low and high concentration regions of FIG. 12 provide the ratios of the "on" and "off" rate constants. The off rate is the same in both cases; it is the off rate of monomers. The on rate reflects the size of the exchanging species.

The conclusion from this data and theory comparison is that there must be oligomers or "microaggregates" of MOPC monomer present in solution below the CMC which take part in the MOPC exchange and which also contribute to the uptake above the CMC, i.e., the PEG layer samples the size distribution of these aggregates.

Fixed MOPC Bulk Concentration (100 µM); Variable mol % PEG-Lipid (0–20 mol %)

Figure 13:
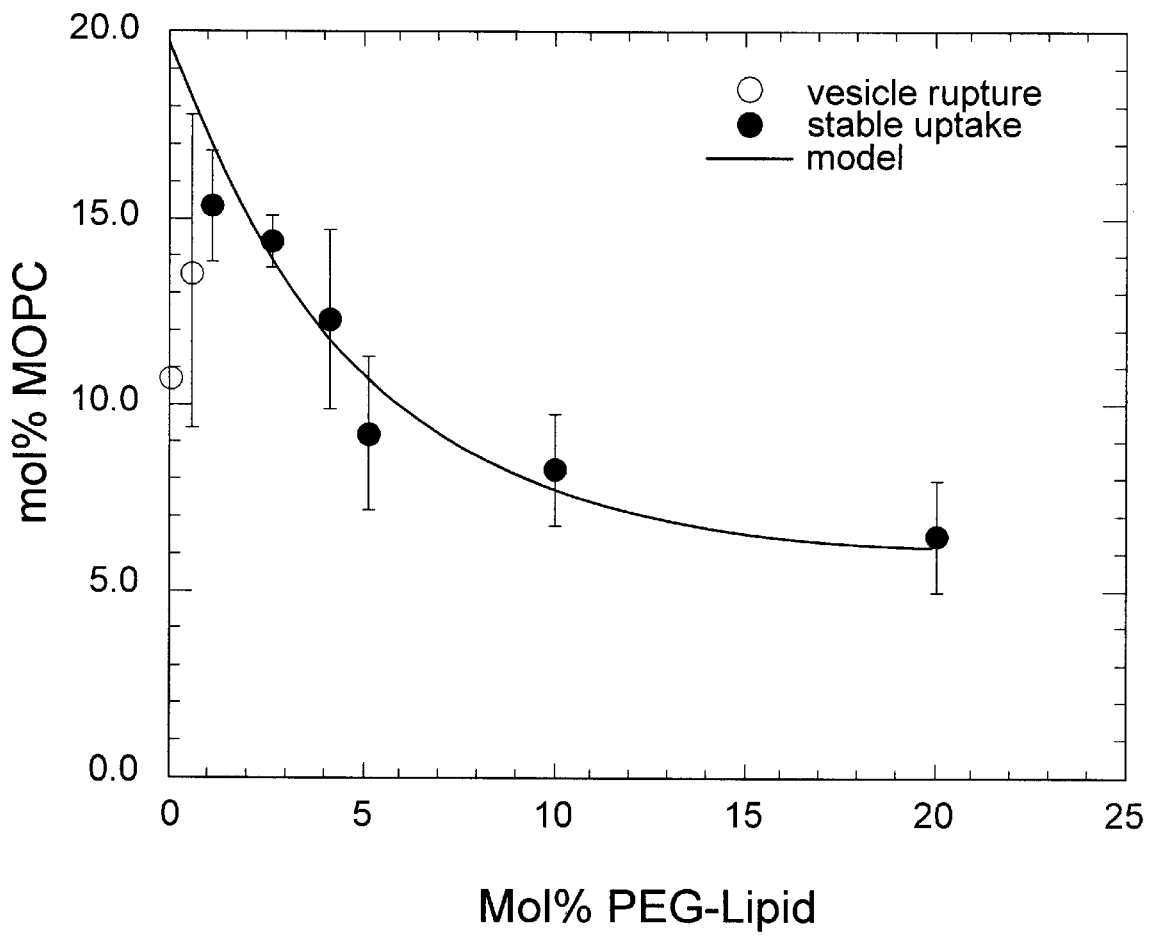
FIG. 13 is the theoretical model for the data provided in FIG. 9, in which the additional work to create a denuded area in a polymer "mushroom"-covered lipid bilayer surface reduces the rate of micelle adsorption.

FIG. 13 provides the theoretical model for the data of FIG. 9, in which the additional work to create a denuded area in a polymer "mushroom"-covered lipid bilayer surface reduces the rate of micelle adsorption. The dependence of uptake on mol % PEG-lipid in the membrane (shown in FIG. 13) is found when the apparent projected area occupied by the micelle in the region of PEG(750) mushrooms is equal to 1400 Å$^2$. This area has a corresponding radius of 21 Å, which is slightly less than the maximum radius at the mid plane of the micelle core (33 Å). Such a radius is obtained when a micelle is just touching mushrooms on either side and the headgroups of its lipids penetrate the headgroup region of the membrane lipids by a few Angstroms as shown in FIG. 11A. This result suggests that micelle-membrane fusion requires intimate contact between the micelle and membrane, i.e., transfer of MOPC from micelles to bilayer can only occur if the micelle "physically" touches the lipid surface and even enters the head group region of the bilayer. For a 20 mol % PEG-lipid bilayer, the micelle is completely excluded from the lipid surface, intimate contact cannot be made and micelle-membrane fusion is inhibited, as shown in FIG. 11B.

EXAMPLE 7

Stabilization of Membranes by Incorporation of Cholesterol

An experiment was conducted as outlined in Example 1, above, however the vesicle membranes contained various amounts of cholesterol (a bilayer-compatible sterol) and no vesicle membranes contained grafted PEG.

Figure 14:
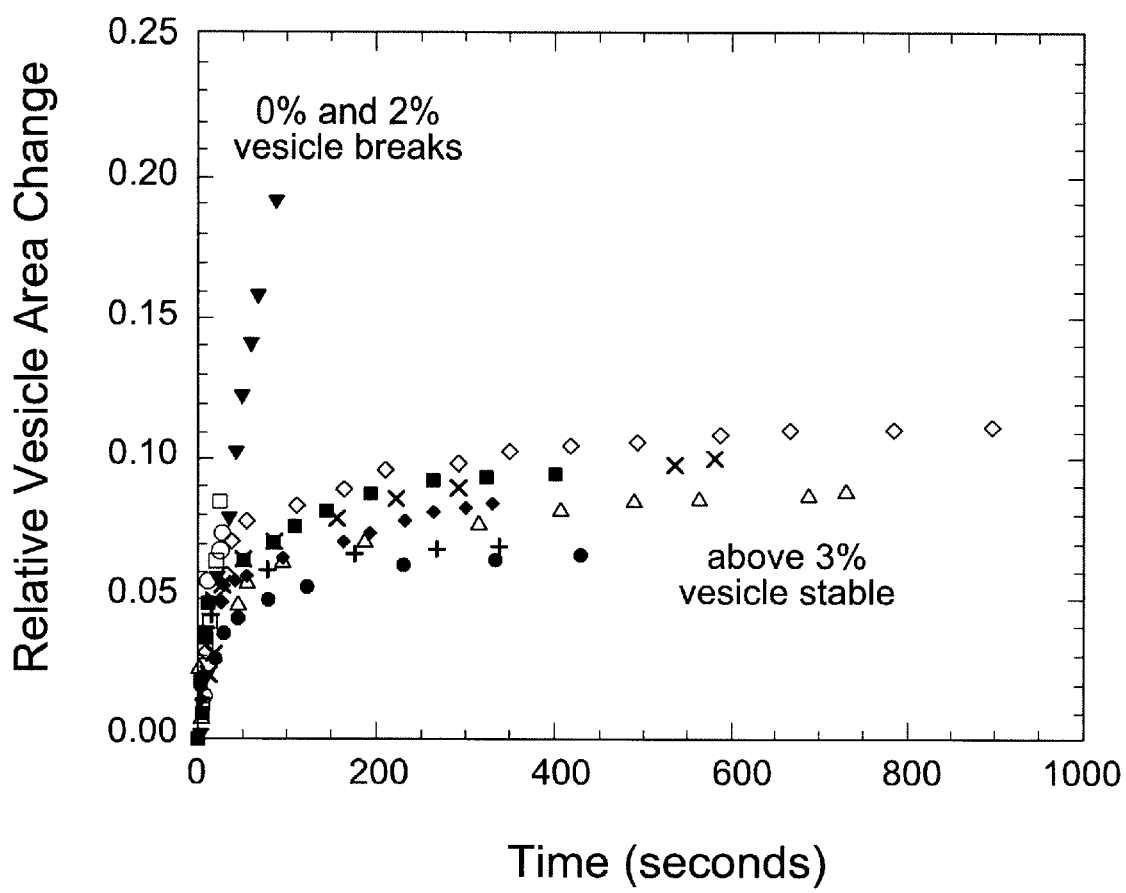
FIG. 14 is a graph of relative vesicle area change due to exposure of SOPC vesicles containing different concentrations (mol %) of cholesterol in the vesicle bilayer to a flow of 100 micromolar MOPC solution. Note that for 0 and 2% cholesterol the vesicles broke when exposed to 100 micromolar MOPC, whereas at all cholesterol concentrations above 3% the vesicles were stable. Open squares=0% cholesterol; inverted filled triangles 2% cholesterol; filled diamonds=3% cholesterol; filled squares 5% cholesterol; filled circles=10% cholesterol; plus signs =20% cholesterol; open triangle=30% cholesterol; "x"=40% cholesterol; open circle=50% cholesterol; open diamond=60% cholesterol.

Experimental results are shown in FIG. 14. In unmodified vesicles (no cholesterol) and vesicles containing 2 mol % cholesterol, exposure to 100 micromolar MOPC caused rupture of the vesicle. In contrast, bilayer vesicles containing from 3 mol % up to saturating bilayer concentrations of about 60 mol % cholesterol, were stable in 100 micromolar MOPC. The effect of cholesterol in the membrane bilayer unexpectedly appeared as a threshold effect in that there was no observable difference among membranes with increasing concentrations of cholesterol above 3 mol %; membranes with 3 mol % of cholesterol provided the same results as those with 60 mol % and were equally able to prevent membrane rupture.

The above results demonstrate that the inclusion of small amounts of cholesterol (from 3 mol % up to saturation at approximately 60 mol %) in lipid bilayers confers a "protective" effect against concentrations of MOPC at least as high as 1 mM. The concentrations of detergent against which cholesterol provides protection are thus even higher than those for which PEG provides protection; PEG coatings failed to protect lipid bilayers against dissolution in 500 micromolar MOPC (data not shown). This unexpected result likely occurs through a different mechanism than that for a PEG graft, since cholesterol does not exert any steric barrier at the surface of the bilayer.

EXAMPLE 8

Encapsulation of Fluorescent Micelles in Lipid Vesicles

The following experiment demonstrated that that concentrations of micelles at 100 microMolar or more could be stably encapsulated inside lipid vesicles, and that the vesicles are in fact stable until acted upon by a force that breaks the vesicle and releases the micellar contents.

Giant lipid vesicles were prepared as described above in Example 1, except that the dried lipid layers were rehydrated with micellar solutions of MOPC (in 206 mOsm sucrose). A fluorescently labelled lipid dye was included in the micellar suspension; this dye became associated in the micelles and so labelled them. Vesicles formed by rehydration in the micelle suspension were placed in an osmotically matched glucose solution (206 mOsm) microchamber on a microscope stage, and individual vesicles were aspirated with a micropipet (as described in the examples above). Using epi-fluorescence illumination, the vesicle was viewed and a high tension was applied to the vesicle to disrupt it. Upon breakage, the fluorescence intensity decayed as the internal content of the vesicle dispersed into the bathing medium.

The present experiment shows that (1) vesicles can be formed in high concentrations of micelle surfactants; (2) such vesicles are stable until acted on by a disrupting force, and (3) the micelles are encapsulated inside the vesicles.

As shown in Examples 1–6, the inclusion of PEG-lipids in a lipid bilayer acts to prevent otherwise bilayer-disrupting micelles from dissolving the lipid bilayer. As shown in Example 7, the inclusion of cholesterol in a lipid bilayer membrane also prevents micelles from dissolving the bilayer. Thus, both PEG-lipid-containing and cholesterol-containing lipid bilayers were investigated as described below.

Two different dyes were used: 2-(4,4-difluoro-5-(4-phenyl-1.3-butadienyl)-4-bora-3a,4 a-diaza-s-indacene-3-pentanoyl)-1-hexadecanoyl-sn-glyce ro-3-phosphocholine (abbreviated to β BODIPY-lipid); and 2-(6-(7-nitrobenz-2-oxa-1,3-diazol-4-yl)amino)hexanoyl-1-hexadecanoyl-sn-glycero-3-phosphocholine) (abbreviated to (NBD-PC(16)).

The following combinations of dye, membrane lipids, PEG-lipids and lysolipids were evaluated for the ability of lipid vesicles to encapsulate a micellar suspension. Vesicles were examined to determine if (1) dye was uniformly fluorescent inside the lipid vesicle and, (2) whether upon tensile failure (induced by high micropipet suction) the internal dye dispersed.

1. Vesicles of SOPC+PEG-lipids; MOPC in Bulk Solution: This trial used SOPC+20 mol % PEG(2000)-lipid (0.2 mg/ml, $2 \times 10^{-4}$ M total lipid) with 100 micromolar LPC. This combination did not form giant lipid vesicles but formed small 1 micrometer sized vesicles; the vesicles were stabilized against LPC disruption (results not shown) but the micropipet disruption test could not be carried out because the vesicles were too small. Although a fluorescence test was not carried out on this preparation, one would not expect to have been able to distinguish fluorescence in the membrane (edge fluorescence) versus the internal bulk volume (homogeneous bulk fluorescence) because the size of the liposomes approached the wavelength of light. Nevertheless, liposomes were prepared with this formulation, and the natural tendency of this formulation to favor small vesicles may be useful where vesicles of small diameter and containing micellar preparations are desired, for example for intravenous drug delivery. Such formulations can be used to provide extruded unilamellar vesicles of 200 nm diameter containing micelles.

2. Vesicles of SOPC+PEG-lipids; PEG-lipids in Bulk Solution: In this trial, PEG-lipids were used as the micellized solubilizing agent as well as in the lipid vesicle membranes.

The concentration at which PEG-lipid (DSPE-PEG2000) forms micellar structures was assessed by a simple fluorescence assay using DPH spectroscopy as described earlier (Example 1), and was found to be approximately 1 micromolar. This second trial used SOPC +20 mol % PEG2000 DSPE (0.2 mg/ml, $2 \times 10^{-4}$ M total lipid) for the lipid vesicles and 1 mM PEG2000 DSPE as micellar suspension. Using 0.04 mol % of NBD-PC as the dye, bulk fluorescence was observed in the lipid vesicles but the vesicles were very rigid and could not be broken simply with micropipet suction. It was as though the PEG-lipids at this high concentration had formed a gel inside the vesicles. Negative stain electron micrograph pictures (not shown) of PEG-lipid micelles show that they are highly filamentous, suggesting that this gel is some sort of an entangled micellar phase. However, fluorescent micelles of PEG-lipids were shown to be encapsulated inside the giant lipid vesicles and we would expect them to also be encapsulated inside extruded unilamellar vesicles.

Figure 16:
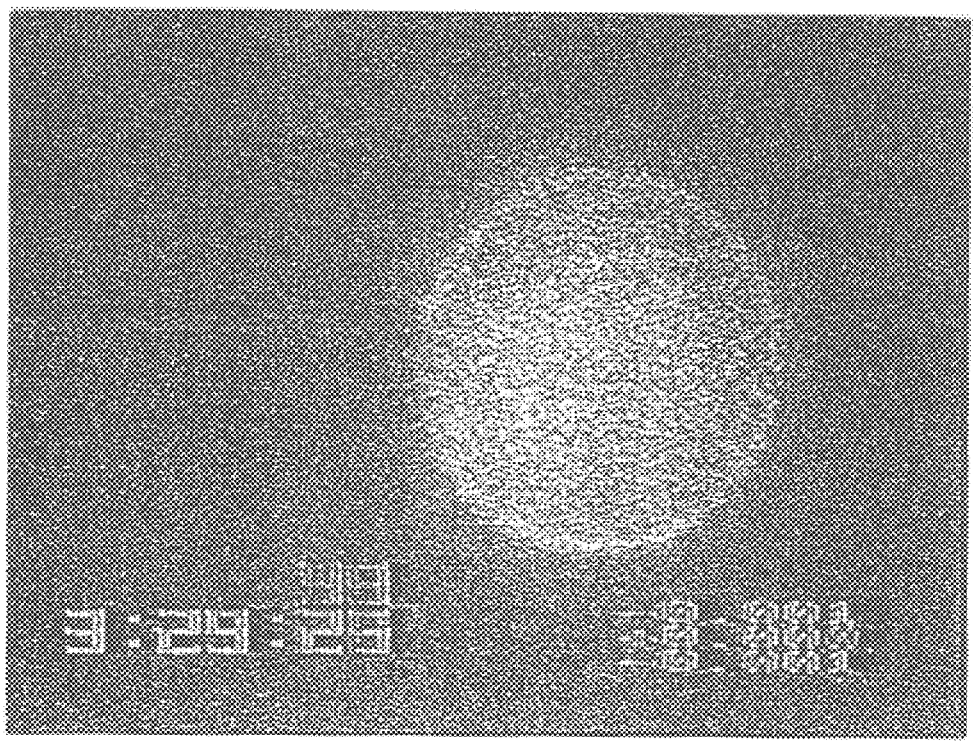
FIG. 16 is a videomicrograph of an SOPC:cholesterol vesicle (at a mole ratio of 1:1) that was rehydrated in 500 micromolar MOPC containing 3 mol % NBD-PC, viewed in epifluorescence illumination. The bright interior of the vesicle indicates that a fluorescently labelled micelle suspension was captured inside the vesicle upon formation in the concentrated micelle suspension.

3. Vesicles of SOPC+Cholesterol; MOPC in Bulk Solution: This trial used cholesterol as a stabilizing component in the lipid vesicle membranes; MOPC was the micelle-forming surfactant. No PEG-lipid was utilized in this trial. Vesicles were made from SOPC:cholesterol at a mole ratio of 1:1 and were rehydrated in 500 micromolar and 1 millimolar MOPC containing 0.3 mol % NBD-PC. Vesicles were large enough to be manipulated with the micropipet and contained a bulk fluorescence as shown in FIG. 16, indicating that the vesicle contained the fluorescent micelles. The edge fluorescence also shows that the lipid dye partitioned into the bilayer, (consistent with our observations that single molecules can cross the PEG layer). The bulk fluorescence rapidly dissipated when the was vesicle broken under applied membrane tension, indicating that the micelles were indeed stably encapsulated in the cholesterol-rich membrane.

The results of the above trials showed that (1) vesicles can be formed in high concentrations of micelle surfactants; (2) such vesicles are stable until acted upon by a disrupting force, and (3) micelles are stably encapsulated inside such vesicles.

The present invention comprises three components: vesicles formed of lipid bilayers, micelles contained therein, and active agents associated with the vesicle and/or micelle. These components each can possess a variety of chemical features, and can be assembled in various combinations in the rational design of a given active agent delivery system, depending on the solubility of the active agent and its intended target. The present invention represents a portfolio of constructs available to dissolve, encapsulate and deliver drugs to a given site in the body. Various embodiments of the present invention are depicted in FIGS. 17a and 17b.

EXAMPLE 9

Quantification and Preparation of Drug-Associated Micelles

When formulating a drug into a micelle-liposome preparation according to the present invention, the solubility limit of the drug in the micelle phase must be determined. The present example utilized TAXOL®, a drug with poor water solubility (about 1 micromolar).

Figure 21:
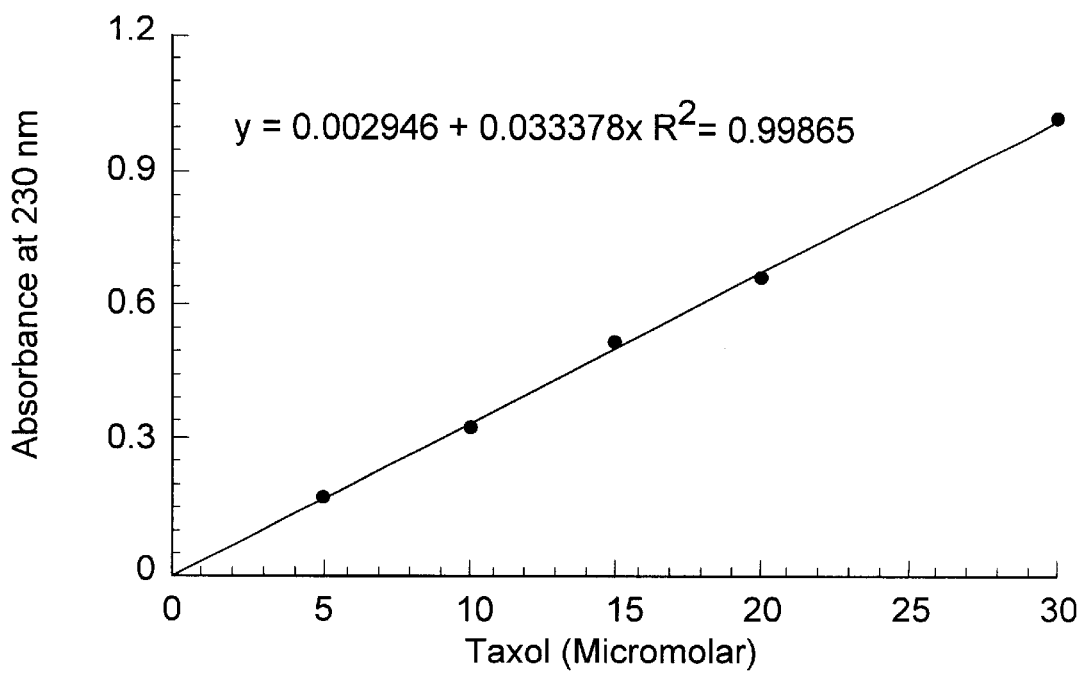
FIG. 21 shows the calibration curve of TAXOL® in methanol which was used for the quantification of TAXOL®. TAXOL® was dissolved in methanol at a concentration ranging from 5 $\mu$M to 30 $\mu$M and the absorbance of each solution was measured at 230 nm on a UV/VIS spectrophotometer. Unknown samples containing TAXOL® were quantified against this calibration curve. y=0.002946+ 0.033378x $R^2$=0.99865.

The concentration of TAXOL® in aqueous solution or aqueous micelle suspension was detected and measured using spectrophotometric absorbance at a wavelength of 230 nm (FIG. 21). The concentration of TAXOL® in a solution or suspension could be measured in the range of 5–50 micromolar. For concentrations higher than 50 micromolar, samples were diluted in methanol and the original concentrations were back-calculated.

Samples were prepared containing the required aliquot of TAXOL® in methanol and MOPC (a micelle forming surfactant) in chloroform. These components were mixed together in glass culture tubes, and the mixture was dried and kept under vacuum for approximately 15 hours to evaporate the solvent. MOPC was chosen because it has an acyl chain composition that matches the di-chain phospholipid, stearoyloleoylphosphatidylcholine, that was used to form the lipid bilayers of encapsulating liposomes, as discussed below. Additionally, MOPC has a Critical Micelle Concentration (CMC) in the micromolar range; we have found that for bilayers to be stable in the presence of micelles, the micelle-forming surfactant must have a low CMC. Surfactants with high CMCs (e.g., in the mM range) readily dissolve lipid membranes, even when the membranes contain cholesterol.

The dried MOPC/TAXOL® film was then hydrated with buffer (10 mM phosphate buffer in 0.8% saline at pH 7.4), centrifuged at 2000 rpm for ten minutes to spin down any undissolved TAXOL® (depending on the ratio of MOPC to TAXOL®, the drug can precipitate out as small crystals detectable with an optical light microscope). The remaining supernatant is then dissolved in methanol and assayed for TAXOL® content. TAXOL® was quantified against the calibration curve of TAXOL® in methanol (FIG. 21). The graph of FIG. 22 represents the maximum amount of TAXOL® in aqueous micelle suspension as a function of time after preparation.

Figure 22:
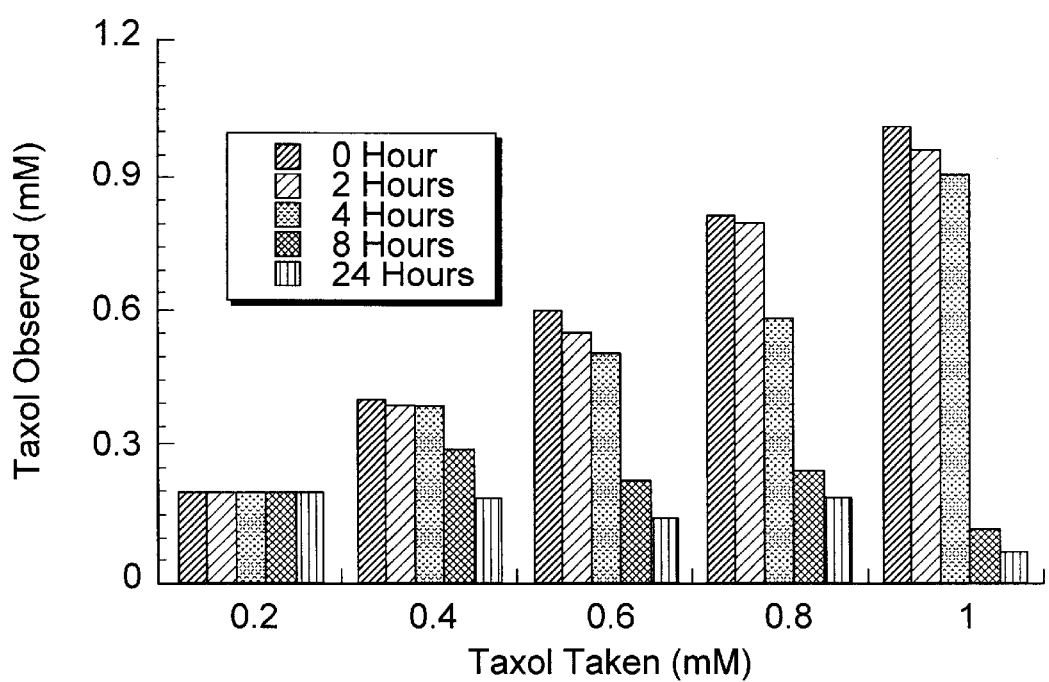
FIG. 22 graphs the loading of TAXOL® in 5 mM MOPC in PBS at a concentration range of TAXOL® varying from 0.2 mM to 1.0 mM. Amounts of TAXOL® were quantified against the calibration curve of TAXOL® in methanol (FIG. 21). The graph represents the maximum amount of TAXOL® in aqueous micelle suspension as a function of time after preparation, where the solid bar is 0 hours after preparation, diagonal slashed bar is 2 hours after preparation, gray bar is 4 hours after preparation, cross-hatched bar is 8 hours after preparation, and vertically lined bar is 24 hours after preparation.

Data for uptake of TAXOL® into MOPC micelle suspensions is shown in FIG. 22. It was found that TAXOL® can be solubilized up to 1 mM in 5 mM MOPC, compared to its natural solubility in water of about 1 micromolar. For 0.2 mM TAXOL®, the TAXOL® is stable in the micelle suspension for at least 24 hours. With increasing amounts of TAXOL® in the suspension, the TAXOL® has a tendency to precipitate from the micelles and form crystals in the aqueous phase. This precipitation, however, does not occur significantly for the first four hours, but then proceeds rapidly as higher amounts of TAXOL® are solubilized. At 1 mM in micelle suspension, the TAXOL® is 1000 times its natural solubility limit, and thus is extremely oversaturated. When TAXOL® crystals are separated from the micelle suspension, our analysis shows that they do not contain any MOPC, suggesting that TAXOL® precipitates alone and partitions from the micelle suspension into its own crystallites. TAXOL® thus has a stronger interaction with itself than with the solubilizing micelle. Therefore, in preparing TAXOL® formulations (and possibly other drug formulations) it is necessary to monitor the amount of drug associated with the micelles as a function of time after rehydration. In the present case, TAXOL® should be formulated into its final encapsulated form within four hours. Once encapsulated, any precipitation of drug into the aqueous phase would remain trapped inside the lipid capsule, and thus retained in the drug delivery system.

Figure 23:
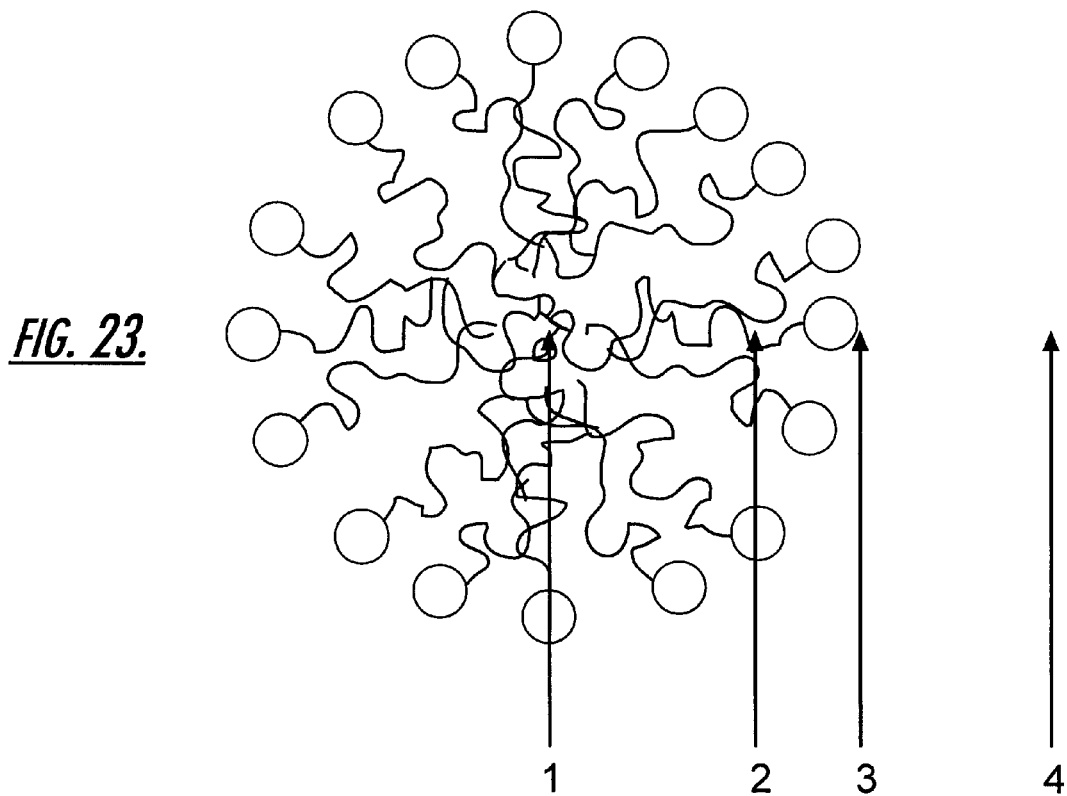
FIG. 23 schematically shows the four regions of a micelle that can solubilize or associate drug molecules. The four regions are (1) central core; (2) outer hydrocarbon chains; (3) headgroup; (4) hydration layer.

TAXOL® was found to be largely insoluble in hexane. The absorbance spectrum of TAXOL® in water, ethanol, and the LPC micelle suspension were similar to each other and all were different than that in hexane. From these experiments, we determined that TAXOL® is not dissolved in the largely hydrophobic (oily) micelle interior, but rather is associated with the surface of the micelle, probably intercalating into the headgroup and outer chain regions. Those skilled in the art will appreciate that each drug will have its own specific interaction with micelles and may be solubilized by the micelle in any one, or combination, of the four regions of the micelle as depicted in FIG. 23.

Figure 24:
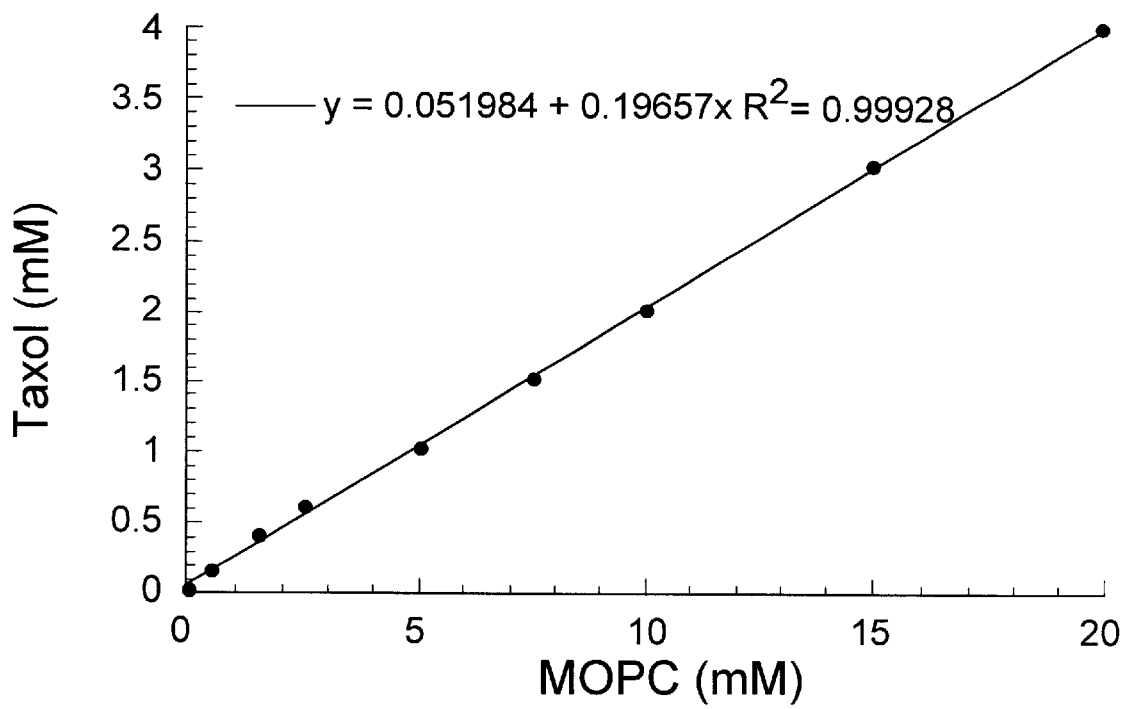
FIG. 24 shows the maximum loading capacity of TAXOL® in micelles as MOPC concentration is increased from 0 mM to 20 mM. y=0.051984+0.19657x $R^2$=0.99928.

To evaluate how much TAXOL® can be solubilized by MOPC micelles as a function of MOPC concentration, we measured the amount of TAXOL® solubilized by MOPC micelles as the concentration of MOPC was increased from 0 to 20 mM. FIG. 24 shows that the amount of TAXOL® solubilized increases linearly with MOPC concentration at a rate of 1 mole of TAXOL® per 5 moles MOPC. It is expected that TAXOL® will keep pace with MOPC concentration, possibly up to the solubility limit of MOPC which is in the molar range.

Sample preparation of TAXOL® solubilized by MOPC micelles can be summarized as follows: place required aliquots from stocks of TAXOL® and MOPC in a culture tube; evaporate solvents by sparging nitrogen; keep culture tubes overnight under vacuum in a desiccator; hydrate TAXOL® MOPC films with PBS and vortex for five minutes; centrifuge at 2000 rpm for 10 minutes; measure TAXOL® in the supernatant against calibration curve.

EXAMPLE 10

Quantification of Drug Loading into Bilayer

Drug may also partition into or be adsorbed at the interface of a bilayer membrane. The present Example quantified the amount of drug partitioning into an otherwise empty liposome (i.e., that partitions into the liposome membrane and internal aqueous space). Experiments were carried out where MOPC and cholesterol were systematically varied in 16 mM SOPC with one component variation at a time.

The desired components were dissolved in chloroform and the solvent was dried off in a round bottom flask using rotavapor by heating the flask at about 50 degree C., under vacuum. Flasks were then evacuated for 15 hours to remove the last traces of solvent. The lipid/drug mixture was then hydrated with PBS buffer by gently etching the dried lipid films with a TEFLON® bead, and a liposome suspension was made and processed within two hours according to the method developed by Hope et al., 812:55 *Biochem Biophys Acta* (1985). This preparation method produces Large Unilamellar Vesicles by Extrusion Technique (LUVETs) of a desired size, in this case 200 nm.

The liposomes were then separated from the unencapsulated TAXOL® by size exclusion chromatography (SEC). SEPHAROSE® CL-4B gel was used to make 5 cm long and 1 cm wide SEC mini columns. The gel was added to the columns and the columns were centrifuged at 2800 rpm for ten minutes. These minicolumns were pre-equilibrated with empty liposomes of the same concentration to avoid the loss of any lipids on to the columns when samples having TAXOL® are passed through the columns. An aliquot of liposome sample is added carefully and gently in the center of the column. The sample containing columns were further centrifuged at 2900 rpm for ten minutes. The cleaned liposome fraction eluted out of the column was assayed for TAXOL® content in all cases by dissolving an aliquot of lipid/TAXOL® mixture in methanol and using the spectrophotometric assay (as described above; at 230 nm). In some cases, the cleaned liposomes were also evaluated for lipid content using Bartlett's phosphate assay. There was very little loss of lipid onto the SEC column when the columns were pre-conditioned with empty liposomes.

SOPC/MOPC

Using a fixed SOPC/MOPC mole ratio of 16/4 (as mM aqueous concentration), we measured the amount of TAXOL® associated with liposomes as made, and during processing, and compared these numbers to the initial amount of TAXOL® mixed with the lipid. Samples were formed by mixing all the components together in chloroform and evaporating the solvent. The lipid films were hydrated with PBS and liposomes produced. At this lipid concentration (16 mM) the liposomes held about 1.7 mM of TAXOL® after being processed through extrusion and cleaned through SEC columns.

Figure 25:
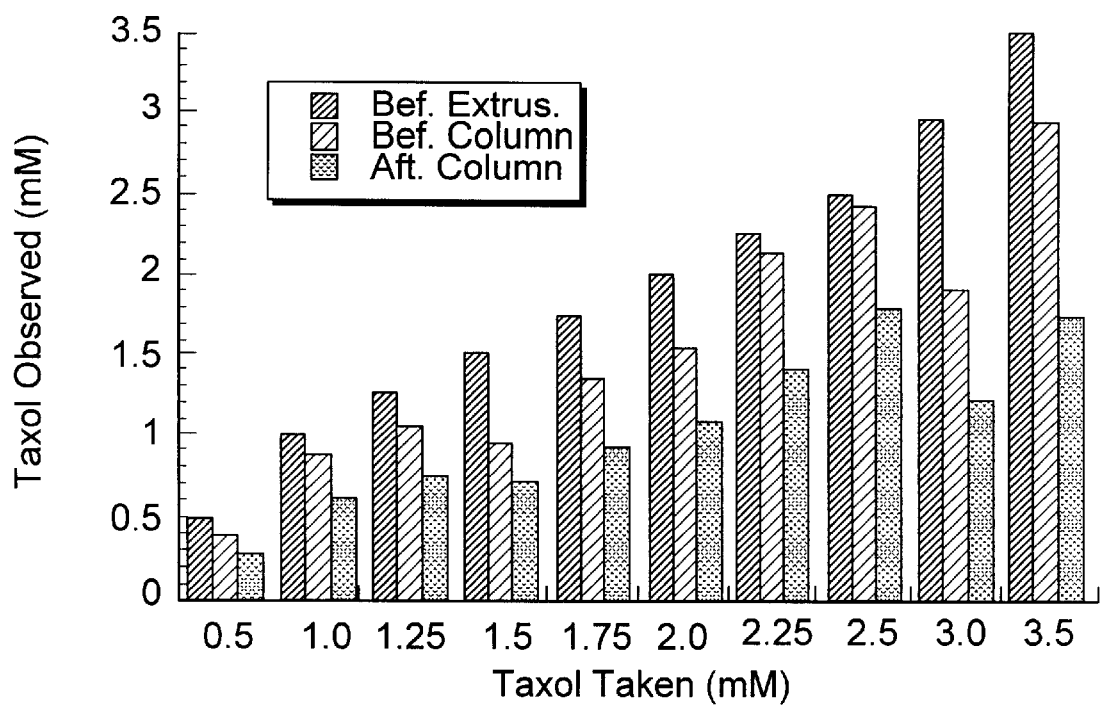
FIG. 25 illustrates the loading of TAXOL® into SOPC/ MOPC (16/4 mM) liposomes, and shows that at this lipid concentration (16 mM), the liposomes can hold about 1.7 mM of TAXOL® once processed through extrusion and cleaned through SEC columns. Solid bars represent TAXOL® content before extrusion; diagonally slashed bars represent TAXOL® before cleaning of liposomes through SEC columns, and gray bars represent TAXOL® after cleaning.

FIG. 25 shows that the initial measured amount of TAXOL® solubilized in the liposome decreases due to losses during processing. It was found that TAXOL® could be solubilized in the liposome preparation before extrusion up to 3.5 mM. Beyond this point the suspension was not homogeneous and insoluble material existed. The maximum amount of TAXOL® taken up in this preparation (which must be largely taken up by the membrane, since water solubility of TAXOL® is about 1 micromolar) was about 1.7 mM. This was observed after cleaning liposomes using SEC columns, and for a phospholipid concentration of 16 mM, i.e., a mole ratio of about 0.11 TAXOL®/phospholipid, which represents one TAXOL® molecule per eleven lipid molecules.

This experiment demonstrates that the liposome bilayer is a significant sink for, and therefor potential transporter of, TAXOL®. This recognition that there is a tendency for TAXOL® to partition into the bilayer phase allows the preparation of a liposome system that carries additional amounts of TAXOL®, by pre-loading the bilayers with TAXOL® at the maximum mole ratio prior to the encapsulation of a drug/micelle phase. The experiment also demonstrates that TAXOL® can be lost from the liposome preparation onto filters and columns. However, clinical formulations of such drug delivery liposomes may not require cleaning, and thus may retain more TAXOL® than cleaned liposomes.

Figure 26:
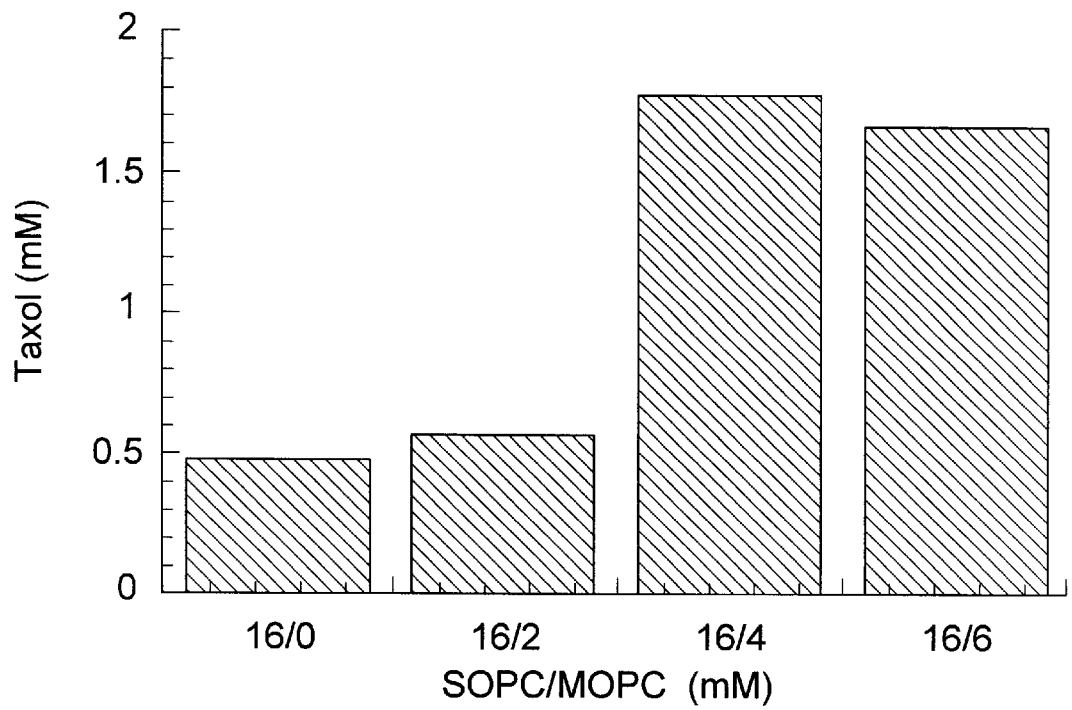
FIG. 26 shows how TAXOL® loading is affected when the mole ratio of MOPC is changed in SOPC liposomes. The size of liposomes was approximately 150–200 nm depending upon the lipid composition used.

This same experiment was carried out for several compositions: 16/0, 16/2, 16/4, and 16/6 SOPC/MOPC. The maximum uptake values after processing (extrusion and cleaning via SEC column) are summarized in FIG. 26. The data show that for pure phospholipid (that is, in the absence of MOPC), only 0.5 mM TAXOL® is retained in the liposome (3 mol % TAXOL® in the phospholipid bilayers). However, by adding MOPC in the bilayer, much more TAXOL® is solubilized in the bilayer phase. At a composition of 16/4 (SOPC/MOPC), 1.7 mM TAXOL® (i.e., 11 mol %) can be solubilized. This amount exceeds previous reported values in the literature that used pure phospholipid liposomes. While not wishing to be held to a particular theory of the present invention, we suspect that MOPC softens the bilayer interface and allows greater partitioning of TAXOL® into the headgroup region of the bilayer.

SOPC/CHOL

Figure 27:
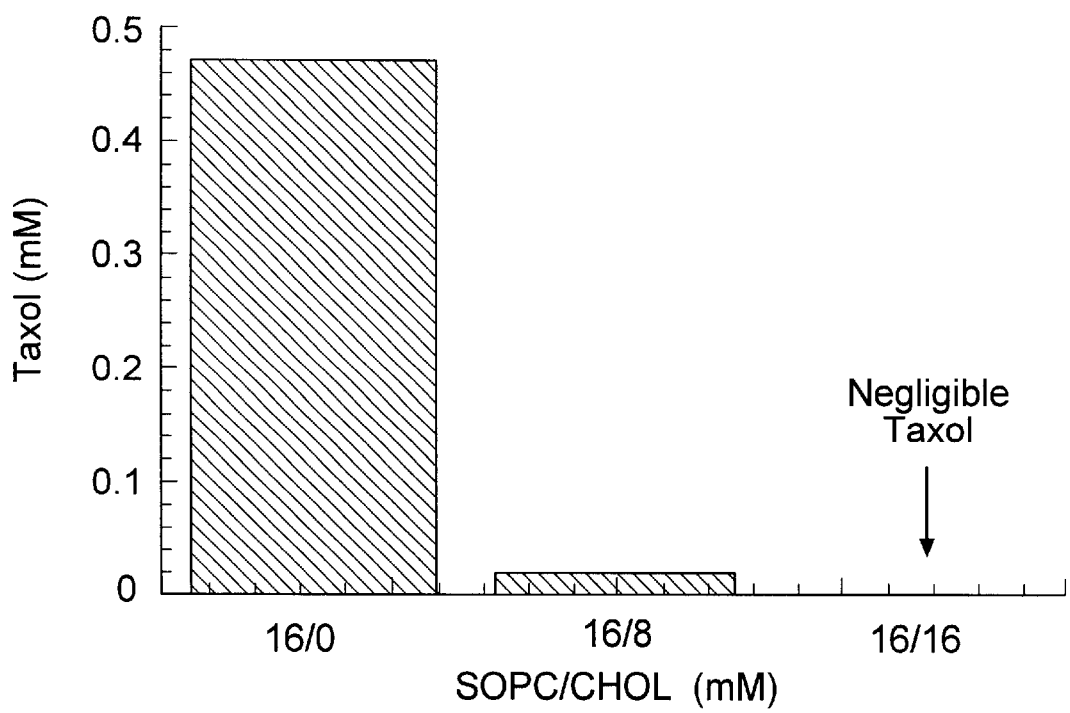
FIG. 27 shows TAXOL® solubilization as a function of cholesterol content for SOPC liposomes. Inclusion of cholesterol at concentrations of 33 mol % and above greatly reduces the capacity of the bilayers to bind TAXOL®.

The effect of varying the cholesterol content of the liposome was studied. As shown in FIG. 27, the inclusion of 33 mol % cholesterol into SOPC membranes reduced the maximum amount of TAXOL® that could be solubilized by the liposome preparation to 15 micromolar. With 50 mol % cholesterol in the bilayers, only 1 micromolar TAXOL® could be solubilized after processing and cleaning by SEC column.

The experiment indicates that a liposome system composed of cholesterol-rich membranes, by itself, will not be an effective delivery system for a poorly water soluble drug such as TAXOL®. While not wishing to be held to a single theory, the mechanism seems to be associated with the state of condensation of the bilayer interface, i.e., cholesterol-rich membranes become increasingly less compressible with increased cholesterol content in the membranes. The highly condensed and stiff cholesterol-rich membrane does not appear to allow the TAXOL® molecules to penetrate and be solubilized by the membrane.

SOPC/CHOL/MOPC

Figure 28:
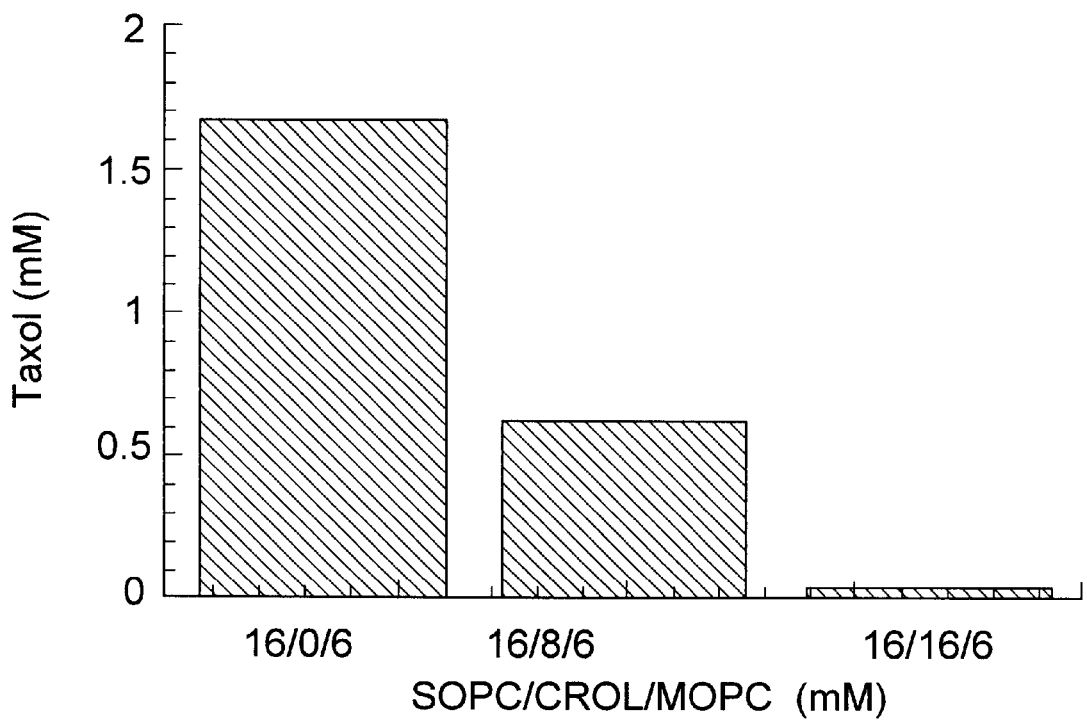
FIG. 28 graphically shows TAXOL® solubilization as a function of cholesterol content for SOPC/MOPC (16/6) liposomes. Inclusion of cholesterol at concentrations of 50 mol % essentially eliminated the capacity of the bilayers to bind TAXOL®. At 33 mol % cholesterol, 0.6 mM TAXOL® was solubilized as shown in FIG. 28.

These experiments measured TAXOL® solubilized by liposome membranes as cholesterol content was varied in liposomes made from fixed SOPC/MOPC 16/6. Data are presented in FIG. 28, and show that for 16 mM of SOPC with 6 mM MOPC, 1.7 mM TAXOL® can be solubilized. But with the addition of 33 mol % cholesterol and 50 mol % cholesterol, the amount of solubilized TAXOL® decreased to 0.6 mM and 0.015 mM, respectively. SOPC alone loads about 0.5 mM TAXOL® (as discussed before in relation to FIG. 27). Thus, interestingly, even though the addition of cholesterol to SOPC membranes dramatically reduced their ability to solubilize TAXOL® (apparently due to the condensation of the membrane surface), the addition of MOPC restored this capacity from 15 micromolar to 0.6 mM for the 33 mol % cholesterol membranes.

In many clinically approved treatments using liposomes, the administered dose is about 100 mM to about 200 mM lipid. The formulation (SOPC/CHOL/MOPC 16/8/16) can be scaled up, e.g., to 100 mM SOPC, which allows 6.4 mM of TAXOL® to be solubilized. This lipid formulation is used in the micelle-liposome construct described below, but it is interesting to note that even in liposomes that do not contain micelles, the present liposome formulation has the capacity to solubilize even greater amounts of TAXOL® if the cholesterol is left out and only SOPC/MOPC composition is used. A similar scale up from the 16/6 formulation, which solubilized 1.7 mM TAXOL®, is expected to therefore solubilize 11 mM TAXOL® (i.e., 11 mol % relative to SOPC).

These present experiments demonstrate that a poorly water-soluble drug such as TAXOL® can be lost from the liposome preparation onto filters and in columns during cleaning of the liposomes. If such cleaning is not required for clinical formulations, it will be apparent that such formulations may carry even greater amounts of drug, e.g., greater amounts of TAXOL® than described herein. Based on the data presented herein, the amount of TAXOL® solubilized could reach 37.5 mM for a 200 mM lipid sample, if the sample is not cleaned through columns as described above.

The following summarizes one protocol for preparing and assessing liposome-solubilized TAXOL®: make stocks of lipids and drug in chloroform; mix aliquots of lipids, cholesterol and/or drug in a 100 mL round bottom flask; evaporate solvents on rotavapor under vacuum by heating at 50 degrees C. and keep flasks under vacuum overnight; hydrate the lipid films with PBS solution and make. MLVs by gently etching the lipid films with a TEFLON® bead and letting equilibrate for one hour; extrude using lipex extruder through a stack of two 0.2 micron polycarbonate fibers eight times to produce LUVETs; make minicolumns from SEPHAROSE® CL-4B in 5 cm syringes, drain out ethanol by constantly flushing with about 20 mL of water and centrifuge at 2800 rpm to remove water in a centrifuge tube; precondition the minicolumns with blank liposomes by gently adding liposomes in the center of SEPHAROSE® column and centrifuge again; similarly add TAXOL® samples in the column and centrifuge, and collect sample at the bottom of culture tubes; take required aliquots in methanol and measure absorbance at 230 nm.

EXAMPLE 11

Partitioning of MOPC into the Bilayer Phase for Micelle Hydration

As noted above, each component of a liposome system has the ability to partition into each compartment of the system.

In liposomes containing a drug/micelle suspension, partitioning of MOPC into the SOPC or SOPC/CHOL liposome bilayer can lead to a depletion of MOPC from the (equilibrated) drug/micelle suspension. In liposomes containing TAXOL®/micelle suspensions, this redistribution of micelle-forming MOPC into the bilayer phase was found to also release TAXOL® from its solubilized state at the surface of the micelle into the aqueous solution. The TAXOL® rapidly exceeded its solubility limit and readily precipitated.

SOPC lipid films were made as described above, in the concentration range of 2 mM to 24 mM, having 50 mol % cholesterol in the membranes. Hydration of cholesterol-rich films was done using 1.5 mM micellized MOPC having 0.25 mM TAXOL® in PBS. The rest of the sample processing is the same as described above in Example 10.

Figure 30:
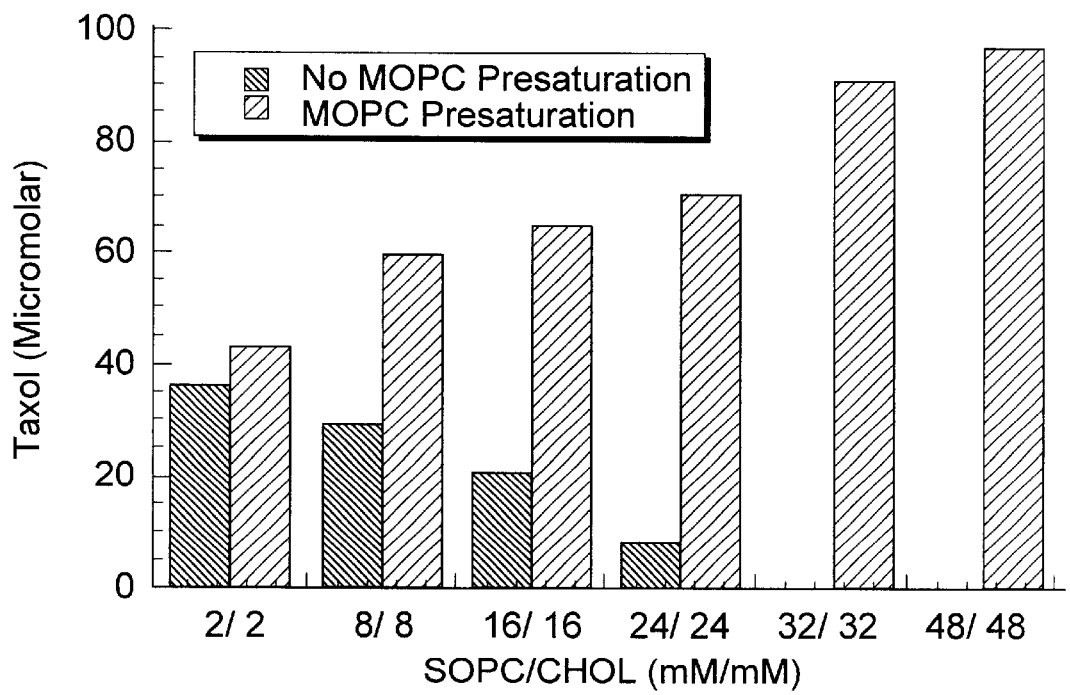
FIG. 30 graphically demonstrates the decrease in TAXOL® encapsulation efficiency with increased lipid concentration, for lipids without 20 mol % presaturation by MOPC; and demonstrates the increase in TAXOL® encapsulation efficiency with increased lipid concentration for lipids with 20 mol % presaturation by MOPC. Lipid films of SOPC/CHOL 1/1 mol ratio with and without the 20 mol % MOPC were made up at increasing lipid concentration from 2 mM to 48 mM as described herein. The lipid films were hydrated with 1.5 mM MOPC micelles having 0.25 mM TAXOL® in PBS. Solid bars represent liposomes without MOPC presaturation; slashed bars represent liposomes with MOPC presaturation.

As shown in FIG. 30, paradoxically, an increase in the total lipid concentration (i.e., greater number of liposomes per ml and therefore greater encapsulated volume) resulted in a decreased amount of TAXOL® being associated with the liposomes. This effect was due to the partitioning of MOPC into the bilayer phase leaving the TAXOL® to precipitate. In other words, TAXOL® that was previously solubilized at 250 times its natural solubility limit, readily precipitated as the micelle population was depleted by MOPC uptake into the bilayer phase. The methods of the present invention overcome this problem by presaturating the bilayer phase with MOPC such that the micelle phase is not depleted. Based on the experiments shown in Example 5 herein, we made an initial estimate and presaturated the lipid film with 20 mol % MOPC. Note that MOPC was chosen as the lysolipid for this system because it matches the acyl chain composition of the bilayer lipid SOPC and so has a large solubility in the membrane without destroying it.

When presaturation of the bilayer phase with 20 mol % MOPC (in relation to SOPC) is carried out prior to the addition of micellized TAXOL®, the amount of TAXOL® associated with the liposome fraction increases to about 100 micromolar measured with lipid concentration over the range shown in FIG. 30, i.e. from 2 to 48 mM lipid. This trend demonstrates the need to presaturate the bilayers with MOPC to maximize the drug carrying ability of liposomes according to the present invention.

Figure 31:
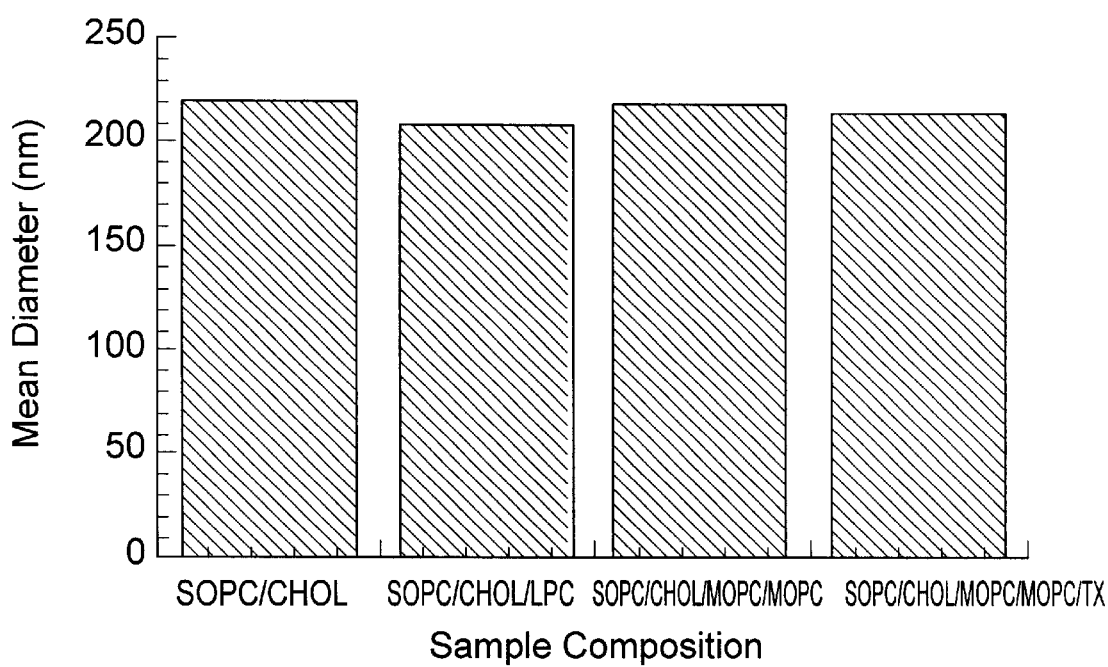
FIG. 31 graphs the mean diameter of liposomes formed from: SOPC/CHOL membranes hydrated with PBS (SOPC/CHOL); SOPC/CHOL/MOPC membranes hydrated with PBS (SOPC/CHOL/MOPC); SOPC/CHOL/MOPC membranes hydrated with MOPC (SOPC/CHOL/MOPC/MOPC); and SOPC/CHOL/MOPC hydrated with MOPC micelles containing TAXOL® (SOPC/CHOL/MOPC/MOPC/TX). Lipids were 40 mM, MOPC was 20 mol % with respect to SOPC; MOPC concentration in micellar form was 2.5 mM, and TAXOL® was 0.25 mM in 2.5 mM MOPC micelles.

The size of liposomes made using various combinations of components was measured, as shown in FIG. 31. The combinations were: SOPC/CHOL membranes hydrated with PBS (SOPC/CHOL); SOPC/CHOL/MOPC membranes hydrated with PBS (SOPC/CHOL/MOPC); SOPC/CHOL/MOPC membranes hydrated with MOPC (SOPC/CHOL/MOPC/MOPC); and SOPC/CHOL/MOPC hydrated with MOPC micelles containing TAXOL® (SOPC/CHOL/MOPC/MOPC/TX). Lipids were 40 mM, MOPC was 20 mol % with respect to SOPC; MOPC concentration in micellar form was 2.5 mM, and TAXOL® was 0.25 mM in 2.5 mM MOPC micelles.

Liposome size was measured using quasi-elastic light scattering. The size of the liposomes did not vary depending on the Liposome composition. The inclusion of MOPC in the lipid, or rehydration with MOPC micelles or micelles that contain TAXOL®, did not destabilize or dissolve the liposomes.

EXAMPLE 12

Optimization of MOPC Presaturation with Respect to TAXOL® Loading in Liposomes for Micelle Hydration The examples provided above indicated that, to develop a liposome formulation with optimized loading of a poorly water-soluble drug (such as TAXOL®), one must allow for the partitioning of micelle MOPC into the bilayer phase, in order to stabilize the micellized drug suspension that is placed within the liposome.

We investigated the amount of MOPC needed to optimize TAXOL® loading in liposomes, using SOPC/CHOL bilayers (16/16) with MOPC concentrations in the bilayers ranging from 2 mM to 8 mM. Hydration of the lipid films was done using 1.5 mM MOPC in micellized form having 0.25 mM TAXOL® in PBS.

Figure 32:
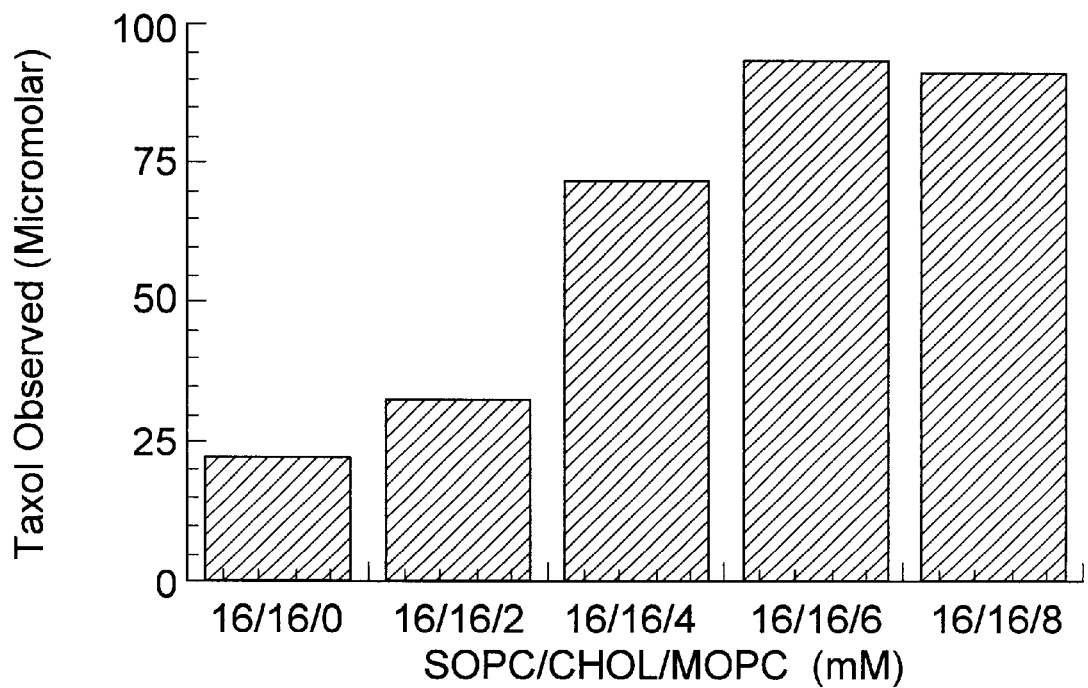
FIG. 32 illustrates the effect, on TAXOL® loading in liposomes, of increased MOPC concentration during presaturation of cholesterol rich bilayers. An increase in TAXOL® encapsulation was observed when MOPC concentration in the bilayer was increased from 2 mM to 8 mM saturating at about 6 mM.

FIG. 32 shows that, for a 1/1 SOPC/CHOL bilayer at 16 mM SOPC, the amount of TAXOL® loaded into the liposome preparation increases with increasing amounts of MOPC presaturation. A maximum of almost 100 micromolar TAXOL® loading is achieved for MOPC presaturation of from about 6 mM to about 8 mM final concentration. It is therefore desirable to presaturate the bilayers with both TAXOL® and MOPC to preserve the micellized drug suspension intact and to fully exploit the capacity of the liposome bilayer to also adsorb TAXOL®.

EXAMPLE 13

Optimization of the Amount of Cholesterol in the Bilayer Phase for Micelle Hydration As described above in Example 7, a certain amount of cholesterol is required to stabilize the liposome bilayer phase in the presence of a micellized drug preparation. Previously, for micelle hydration, we have simply used an amount of cholesterol close to the maximum saturation of approximately 50 mol % cholesterol. However, this amount may not be optimal, especially in the presence of MOPC. We therefore investigated the relationship between the amount of TAXOL® that could be loaded into a liposome (in the bilayer phase and encapsulated in a micellar preparation) as a function of the amount of cholesterol present in a bilayer having a fixed SOPC/MOPC ratio of 16/6, at a lipid concentration of 16 mM. Hydration of lipid films was done with 1.5 mM micellized MOPC having 0.25 mM TAXOL® in PBS.

Figure 33:
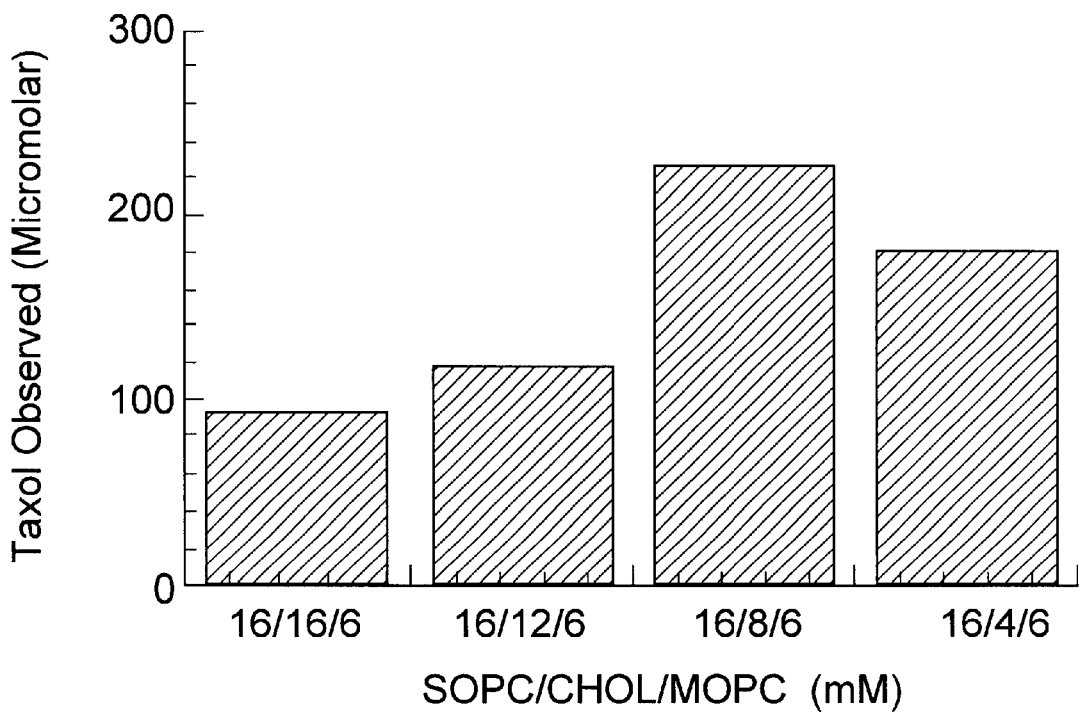
FIG. 33 illustrates that by decreasing the cholesterol content in a bilayer having SOPC and MOPC at 16/6 molar ratio, TAXOL® encapsulation can be almost doubled. Lipid films in which the SOPC/MOPC 16/6 molar ratios were kept constant, and the cholesterol content was decreased from 16 mM to 4 mM, were prepared.

FIG. 33 shows that TAXOL® loading increased with decreasing cholesterol content of the bilayers, reaching a maximum at 16/8/6 (i.e., SOPC/CHOL mole ratio of 2:1). TAXOL® loading seemed to decrease at lower cholesterol concentrations, which may be due to the instability of the bilayer to micelles and MOPC. As discussed above, bilayers without cholesterol are not stable in the presence of such high concentrations of MOPC micelles.

EXAMPLE 14

Optimization of Concentration of Micellized TAXOL®

Figure 34:
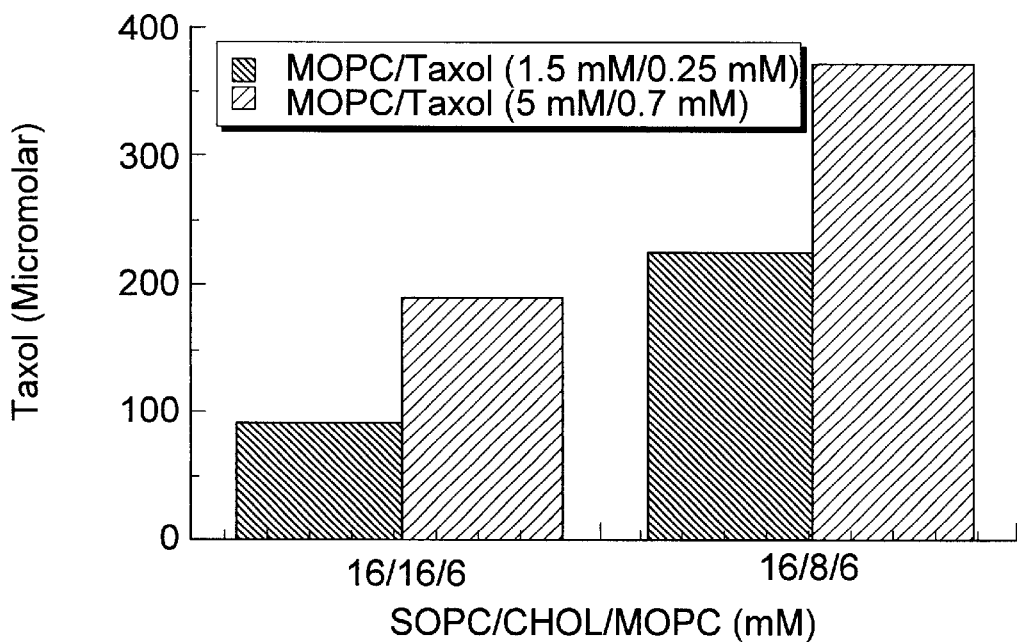
FIG. 34 demonstrates the increase in TAXOL® encapsulation when MOPC micelle concentration is increased to 5 mM, and TAXOL® to 0.7 mM. A comparison is also given for two different formulations having 1:1 and 2:1 SOPC:CHOL with 6 mM MOPC. Solid bars represent MOPC/TAXOL® of 1.5 mM/0.25 mM; hatched bars represent MOPC/TAXOL® of 5 mM/0.7 mM.

We optimized the concentration of micellized TAXOL® used to hydrate a SOPC/CHOL/MOPC/TAXOL® film. Having shown earlier (Example 9) that the limiting amount of TAXOL® that could be solubilized by MOPC micelles was at a mole ratio of 0.2 (i.e., about 5 moles of MOPC per mole TAXOL®), we kept this ratio and increased the overall concentration of each from 1.5 mM MOPC to 5 mL MOPC. FIG. 34 shows the comparison of two formulations having different compositions which were hydrated with 1.5 mM MOPC having 0.25 mM TAXOL®, as well as with 5 mM micellized MOPC loaded with 0.7 mM TAXOL® in PBS.

FIG. 34 clearly shows that for a MOPC/TAXOL® concentration of 5 mM/0.7 mM, the amount of TAXOL® that can be loaded into the liposome system is 400 micromolar when the total lipid concentration is 16 mM, i.e., a final TAXOL®-to-lipid mole ratio of 2.5 mol %.

EXAMPLE 15

Quantification of TAXOL® Associated with Micellized MOPC and with Liposome Bilayer As described in earlier examples, presaturation of a lipid phase with both MOPC and TAXOL®, prior to hydration with micelle-solubilized drug, increases the drug-carrying capacity of the resulting liposome. We found that 6 mM MOPC was needed to presaturate 16 mM SOPC bilayers, and 8 mM of cholesterol was required in these SOPC/MOPC bilayers to give maximum TAXOL® loading. Also, after liposomes are processed by extrusion and SEC columns, the maximum amount of TAXOL® that can be loaded to otherwise empty bilayers (i.e., liposomes without any micelle suspension in the interior) is about 0.6 mM, which is about half of the 1.1 mM TAXOL® in the initial lipid films.

Figure 35:
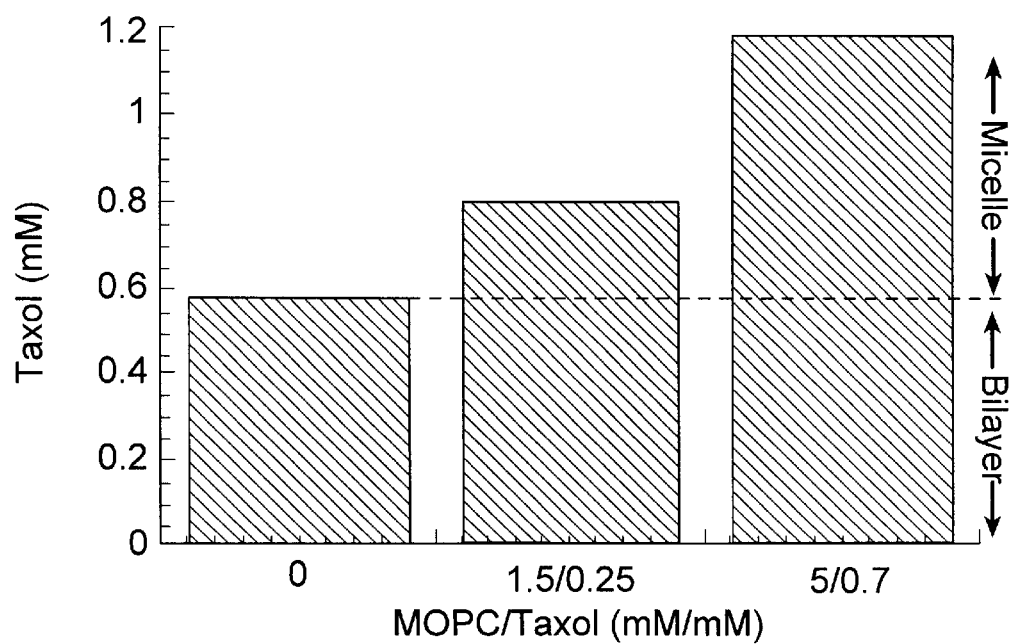
FIG. 35 depicts TAXOL® associated with MOPC micelles encapsulated in SOPC/CHOL/MOPC (16/8/6) liposomes, compared to micelle-free liposomes of the same composition. Lipids were presaturated with 1.1 mM TAXOL® and were hydrated with two different micellar-TAXOL® concentrations: 1.5 mM MOPC micelles/0.25 mM TAXOL® and 5 mM MOPC/0.7 mM TAXOL® in PBS.

Having determined these conditions, we next quantified the amount of TAXOL® associated with micelles that was in fact encapsulated in liposomes. Lipid films were made from 16 mM SOPC and preloaded with 6 mM MOPC, 8 mM cholesterol, and 1.1 mM TAXOL®, by preparing a thin film of all these components together in chloroform. These lipid films were hydrated with either 1.5 mM micellized MOPC loaded with 0.25 mM TAXOL® in PBS, or with 5 mM micellized MOPC loaded with 0.7 mM TAXOL® in PBS. FIG. 35 shows the comparison of these two hydration processes, along with a control (no micelle used for lipid hydration).

Figure 29:
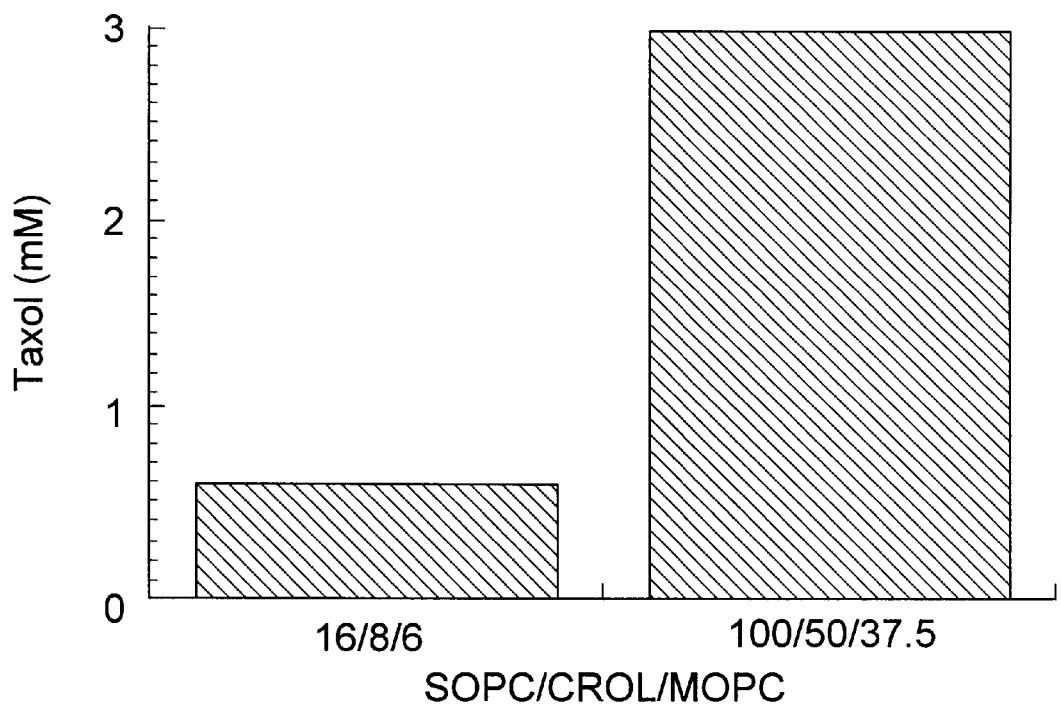
FIG. 29 shows the scale up of the 16/8/6 formulation from 16 to 100 mM SOPC. TAXOL® solubilization increased with increasing lipid concentration to 3.0 mM.

As shown earlier in FIG. 29 and repeated again here for the control, the 16/8/6 composition can solubilize 0.6 mM TAXOL® when hydrated with simple PBS buffer (no micelles). When this composition is hydrated with a MOPC/TAXOL® suspension of 1.5/0.25 (mM), there is an increase in the total solubilized TAXOL® to 0.8 mM.

When the concentration of the micellized TAXOL® suspension is increased to 5/0.7 (mM), the amount of TAXOL® solubilized by the entire system is 1.2 mM.

From these data, we can therefore estimate the amount of TAXOL® that is partitioned into the micelle phase and encapsulated within the liposome interior space, as distinct from TAXOL® solubilized by the bilayer. As shown in FIG. 35, any TAXOL® that is loaded, over and above 0.6 mM, must be in the micelle phase. Thus, for the 1.5/0.25 sample, about 0.2 mM of TAXOL® is contained in the micelle phase, and for the 5/0.7 sample, about 0.6 mM is entrapped with the micelles. This data indicates that TAXOL® can be solubilized in both the bilayer and micelle phases in approximately equal amounts at these bilayer lipid concentrations (16/8/6 mM).

EXAMPLE 16

Optimization of Total Concentration of TAXOL® in Micelle Loaded Liposomes

The present examples demonstrate that the total loading capacity of liposomes for poorly water-soluble drugs can be increased when SOPC bilayers are preloaded with MOPC. Using TAXOL®, loading capacity of liposomes is increased up to 22 mM when SOPC bilayers (200 mM) are preloaded with MOPC. As described in Example 10 and shown in FIGS. 25 and 26, SOPC/MOPC bilayers can solubilize even larger amounts of TAXOL® that, if not columned (i.e., cleaned), could approach 37.5 mM TAXOL® (i.e., 19 mol % with respect to lipid).

The present examples further demonstrate that liposomes containing micellized drug preparations require cholesterol in the lipid bilayers, to stabilize the liposome membrane against the deleterious effects of the micelles contained within. However, cholesterol reduces the amount of TAXOL® that can be solubilized by the bilayer phase of the liposome. Although TAXOL® solubilization is decreased in the lipid bilayer, the micellized TAXOL® in the liposome interior acts to replace the TAXOL®-carrying capacity lost in the bilayer. Scaling up the liposome-micelle formulation described herein from 16 mM to 200 mM SOPC, one could expect about 10–15 mM TAXOL® (i.e., 5 to 7.5 mol % TAXOL®) based on SOPC concentration). As described above, if these preparations are not cleaned using SEC columns, one could expect to achieve up to 15 to 18 mM TAXOL® (7.5–9 mol %).

EXAMPLE 17

Addition of Polyethylene Glycol to Liposomes

The addition of polymers to the exterior surface of lipsomes produced according to the present invention provides additional desirable characteristics.

Liposomes are prepared as described in any of Examples 10–16, above. Polyethyleneglycol (PEG) is grafted to the exterior surface of the liposomes by incubating the preformed liposomes with PEG-containing micelles, as described by Uster et al., *FEBS Letters* 386:243 (1996).

The foregoing is illustrative of the present invention and is not to be construed as limiting thereof. the invention is defined by the following claims, with equivalents of the claims to be included therein.

That which is claimed is:

1. A liposome containing an active agent, wherein the lipid bilayer of the liposome comprises:
   a) phospholipid;
   b) an active agent associated with the lipid bilayer;
   c) surfactant with a Critical Micelle Concentration (CMC) of about 1 millimolar or less, said surfactant contained in the lipid bilayer in an amount sufficient to increase the amount of active agent associated with the lipid bilayer, compared to that amount of active agent that would associate with the lipid bilayer in the absence of surfactant, wherein the active agent is aggregated with said surfactant to form micelles; and
   d) from 3 mole percent to 60 mole percent of cholesterol present in the lipid bilayer in an amount sufficient to protect against the disruptive effects of the surfactant contained in the lipid bilayer,
wherein the lipid bilayer is unilaminar.

2. A liposome according to claim 1, wherein said phospholipid is stearoyloleoylphosphatidylcholine(SOPC).

3. A liposome according to claim 1, wherein said surfactant is a lysolipid.

4. A liposome according to claim 1, wherein said surfactant is a lysophosphatidylcholine.

5. A liposome according to claim 1, wherein said surfactant is monooleyolphosphatidylcholine(MOPC).

6. A liposome according to claim 1, wherein said active agent is paclitaxel.

7. A liposome according to claim 6, where paclitaxel is contained in the lipid bilayer in an amount of at least 10 mol % relative to SOPC.

8. A liposome according to claim 1, said lipid bilayer further comprising polymer-derivatized lipids.

9. A liposome according to claim 7, wherein said polymer is polyethylene glycol.

10. A liposome according to claim 1, wherein said phospholipid is stearoyloleoylphosphatidylcholine(SOPC) and said surfactant is monooleyolphosphatidylcholine(MOPC), and MOPC is present in an amount at least sufficient to provide a mole ratio of 8:1 SOPC:MOPC.

* * * * *